United States Patent
DeVita et al.

(10) Patent No.: US 7,084,156 B2
(45) Date of Patent: Aug. 1, 2006

(54) 2-AMINOQUINOLINE COMPOUNDS

(75) Inventors: Robert J. DeVita, Westfield, NJ (US); Lehua Chang, Ramsey, NJ (US); Danny Chaung, Clark, NJ (US); MyLe Hoang, Colonia, NJ (US); JinLong Jiang, Scotch Plains, NJ (US); Peter Lin, Edison, NJ (US); Andreas W. Sailer, Edison, NJ (US); Jonathan R. Young, Kendall Park, NJ (US)

(73) Assignee: Merck & Co., Inc., Rahway, NJ (US)

( * ) Notice: Subject to any disclaimer, the term of this patent is extended or adjusted under 35 U.S.C. 154(b) by 5 days.

(21) Appl. No.: 10/496,615

(22) PCT Filed: Nov. 22, 2002

(86) PCT No.: PCT/US02/37556

§ 371 (c)(1),
(2), (4) Date: May 25, 2004

(87) PCT Pub. No.: WO03/045313

PCT Pub. Date: Jun. 5, 2003

(65) Prior Publication Data

US 2005/0026915 A1 Feb. 3, 2005

Related U.S. Application Data

(60) Provisional application No. 60/333,581, filed on Nov. 27, 2001.

(51) Int. Cl.
*C07D 215/38* (2006.01)
*C07D 215/16* (2006.01)
*A61K 31/47* (2006.01)

(52) U.S. Cl. ............... 514/312; 514/313; 514/314; 546/159; 546/162; 546/178

(58) Field of Classification Search ............... 546/159, 546/162, 178; 514/312, 314, 313
See application file for complete search history.

(56) References Cited

U.S. PATENT DOCUMENTS

| 4,013,665 | A | 3/1977 | Crenshaw et al. |
| 4,701,459 | A | 10/1987 | Meanwell et al. |
| 5,942,520 | A | 8/1999 | Pamukcu et al. |
| 6,221,613 | B1 | 4/2001 | Salon et al. |
| 6,410,561 | B1 * | 6/2002 | Shinkai et al. ............... 514/313 |
| 6,569,861 | B1 | 5/2003 | Bakthavatchalam et al. |
| 6,720,324 | B1 | 4/2004 | Marzabadie et al. |
| 6,727,264 | B1 | 4/2004 | Marzabadi et al. |
| 2003/0023085 | A1 | 1/2003 | Chen et al. |
| 2003/0105094 | A1 | 6/2003 | Clader et al. |
| 2003/0144261 | A1 | 7/2003 | Palani et al. |
| 2003/0191136 | A1 | 10/2003 | Bakthavatchalam et al. |
| 2003/0229119 | A1 | 12/2003 | Kym et al. |
| 2004/0006370 | A1 | 1/2004 | Cheng et al. |
| 2004/0106645 | A1 | 6/2004 | Blackburn et al. |

FOREIGN PATENT DOCUMENTS

| EP | 0 252 503 | 11/1992 |
| JP | 2001-226269 | 8/2001 |
| JP | 371059 | 12/2002 |
| WO | WO 96/28446 | 9/1996 |
| WO | WO 98/27815 | 7/1998 |
| WO | WO 99/19326 | 4/1999 |
| WO | WO 99/31086 | 6/1999 |
| WO | WO 99/42464 | 8/1999 |
| WO | WO 99/48492 | * 9/1999 |

(Continued)

OTHER PUBLICATIONS

Antelman et al., Chem. Abstract, 91:68543, Current Medical Research and Opinion (1979), vol. 6, pp. 73-82, "The importance of stress in assessing the effects of anorectic drugs".

(Continued)

*Primary Examiner*—D. Margaret Seaman
(74) *Attorney, Agent, or Firm*—Catherine D. Fitch; Melvin Winokur

(57) ABSTRACT

The present invention is concerned with compounds of the general Formula I:

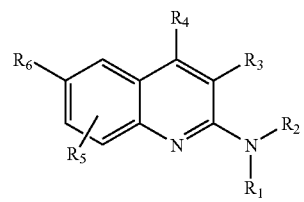

and pharmaceutically acceptable salts thereof, which are useful as melanin concentrating hormone receptor antagonists, particularly MCH-1R antagonists. As such, compounds of the present invention are useful for the treatment or prevention of obesity or eating disorders associated with excessive food intake and complications thereof, osteoarthritis, certain cancers, AIDS wasting, cachexia, frailty (particularly in elderly), mental disorders stress, cognitive disorders, sexual function, reproductive function, kidney function, locomotor disorders, attention deficit disorder (ADD), substance abuse disorders and dyskinesias, Huntington's disease, epilepsy, memory function, and spinal muscular atrophy. Compounds of formula I may therefore be used in the treatment of these conditions, and in the manufacture of a medicament useful in treating these conditions. Pharmaceutical formulations comprising one of the compounds of formula (I) as an active ingredient are disclosed, as are processes for preparing these compounds.

18 Claims, No Drawings

FOREIGN PATENT DOCUMENTS

| | | |
|---|---|---|
| WO | WO 99/53924 | 10/1999 |
| WO | WO 00/18740 | 4/2000 |
| WO | WO 00/35919 | 6/2000 |
| WO | WO 00/64877 | 11/2000 |
| WO | WO 01/21169 | 3/2001 |
| WO | WO 01/21577 | 3/2001 |
| WO | WO 01/32646 | 5/2001 |
| WO | WO 01/40218 | 6/2001 |
| WO | WO 01/47892 | 7/2001 |
| WO | WO 01/68186 | 9/2001 |
| WO | WO 01/72758 | 10/2001 |
| WO | WO 01/82925 | 11/2001 |
| WO | WO 01/87834 | 11/2001 |
| WO | WO 02/00654 | 1/2002 |
| WO | WO 02/04433 | 1/2002 |
| WO | WO 02/06245 | 1/2002 |
| WO | WO 02/042458 | 5/2002 |
| WO | WO 02/051809 | 7/2002 |
| WO | WO 02/070522 | 9/2002 |
| WO | WO 02/076929 | 10/2002 |
| WO | WO 02/076947 | 10/2002 |
| WO | WO 02/083134 | 10/2002 |
| WO | WO 02/089729 | 11/2002 |
| WO | WO 02/094799 | 11/2002 |
| WO | WO 03/004027 | 1/2003 |
| WO | WO 03/013574 | 2/2003 |
| WO | WO 03/015769 | 2/2003 |
| WO | WO 03/027239 | 4/2003 |
| WO | WO 03/027240 | 4/2003 |
| WO | WO 03/028641 | 4/2003 |
| WO | WO 03/033476 | 4/2003 |
| WO | WO 03/033480 | 4/2003 |
| WO | WO 03/035055 | 5/2003 |
| WO | WO 03/035624 | 5/2003 |
| WO | WO 03/045918 | 6/2003 |
| WO | WO 03/045920 | 6/2003 |
| WO | WO 03/059289 | 7/2003 |
| WO | WO 03/070244 | 8/2003 |
| WO | WO 03/087044 | 10/2003 |
| WO | WO 03/087045 | 10/2003 |
| WO | WO 03/087046 | 10/2003 |
| WO | WO 03/097047 | 11/2003 |
| WO | WO 2004/002987 | 1/2004 |

OTHER PUBLICATIONS

Kato et al., Chem. Abstract, 134:266103, "Preparation of N-tetrahydronaphthalenyl carboxamides of melanin concentrating hormone antagonists".

Mueller et al., Chem. Abstract, 138:4532, "Preparation of quinolines as ligands for the neuropeptide Y receptor useful against arthritis, cardiovascular diseases, diabetes, renal failure, eating disorders and obesity".

Shinkai et al., J. Med. Chem., vol. 43 (2000), pp. 4667-4677, "4-Aminoquinolines: Novel nociceptin antagonist with analgesic activity".

Lanza et al., J. Med. Chem., vol. 35 (1992), pp. 252-258, "Substituted 4,6-diaminoquinolines as inhibitors of C5a receptor binding".

Ganoub, Heterocyclic Communications, vol. 7(2) (2001), pp. 143-148, "A facile approach to N-heterocycles. The reactions of ylide phosphoranes with hydrazones".

Kowalski et al., Expert Opin. Investig. Drugs, vol. 13(9) (2004), pp. 1113-1122. "Therapeutic potential of melanin-concentrating hormone- 1 receptor antagonists for the treatment of obesity".

Clark et al., J. Med. Chem., vol. 47 (2004), pp. 3962-3971, "A virtual screening approach to finding novel and potent antagonists at the melanin-concentrating hormone 1 receptor".

Arienzo et al., Bioorg. & Medicinal Chem. Letters, vol. 14 (2004), pp. 4099-4102, "Structure-activity relationships of a novel series of melanin-concentrating hormone (MCH) receptor antagonists".

* cited by examiner

2-AMINOQUINOLINE COMPOUNDS

CROSS-REFERENCE TO RELATED APPLICATIONS

This application is a U.S. National Phase application under 35 U.S.C. § 371 of U.S. Application No. PCT/US02/37556, filed Nov. 22, 2002, which claims priority under 35 U.S.C. § 119 from U.S. Provisional Application No. 60/333,581, filed Nov. 27, 2001.

BACKGROUND OF THE INVENTION

Obesity, defined as excess adiposity for a given body size, results from a chronic imbalance between energy intake and energy expenditure. Body mass index (BMI, kg/m$^2$) is an accepted clinical estimate of being overweight (BMI 25 to 30) and of obesity (BMI>30). A BMI above 30 kg/m$^2$ significantly increases the risk of diabetes, hypertension, dyslipidemias and cardiovascular disease, gallstones, osteoarthritis and certain forms of cancer and reduces life expectancy.

In the vast majority of obese individuals, the cause of the excess adiposity is not immediately apparent. A currently accepted working hypothesis is that obesity is the result of a maladaptation of the innate metabolic response to environmental challenges such as unlimited availability of low cost/energy dense foods and sedentariness (Hill et al., Science 1998; 280:1371). The study of energy intake in free living humans has met with only limited success and definitive experimental evidence that hyperphagia causes most forms of human obesity is lacking. Following the discovery of leptin, the interest in the neurohormnonal regulation of food intake has regained momentum. However, while much knowledge has been gained on the regulation of food intake in rodents and other animal species, the understanding of the neurophysiology of feeding behavior in humans remains extremely limited.

Neuropeptides present in the hypothalamus play a major role in mediating the control of body weight. (Flier, et al., 1998. *Cell*, 92, 437–440.) Melaninoncentrating hormone (MCH) is a cyclic 19-amino acid neuropeptide synthesized as part of a larger pre-prohormone precursor in the hypothalamus which also encodes neuropeptides NEI and NGE. (Nahon, et al., 1990. *Mol. Endocrinol.* 4, 632–637.) MCH was first identified in salmon pituitary, and in fish MCH affects melanin aggregation thus affecting skin pigmentation. In trout and in eels MCH has also been shown to be involved in stress induced or CRF-stimulated ACTH release. (Kawauchi, et al., 1983. *Nature* 305, 321–323.)

In humans two genes encoding MCH have been identified that are expressed in the brain. (Breton, et al., 1993. *Mol. Brain Res.* 18, 297–310.) In mammals MCH has been localized primarily to neuronal cell bodies of the hypothalamus which are implicated in the control of food intake, including perikarya of the lateral hypothalamus and zona inertia. (Knigge, et al., 1996. *Peptides* 17, 1063–1073.)

Pharmacological and genetic evidence suggest that the primary mode of MCH action is to promote feeding (orexigenic). MCH mRNA is up-regulated in fasted mice and rats, in the ob/ob mouse and in mice with targeted disruption in the gene for neuropeptide Y (NPY). (Qu, et al., 1996. *Nature* 380, 243–247, and Erickson, et al., 1996. *Nature* 381, 415–418.) Injection of MCH centrally intracelebroventricular (ICV) stimulates food intake and MCH antagonizes the hypophagic effects seen with α melanocyte stimulating hormone (αMSH). (Qu, et al., 1996. *Nature* 380, 243–247.) MCH deficient mice are lean, hypophagic and have increased metabolic rate. (Shimada, et al., 1998. *Nature* 396, 670–673.)

MCH action is not limited to modulation of food intake as effects on the hypothalamic-pituitary-axis have been reported. (Nahon, 1994. *Critical Rev. in Neurobiol.* 8, 221–262.) MCH may be involved in the body response to stress as MCH can modulate the stress-induced release of CRF from the hypothalamus and ACTH from the pituitary.

In addition, MCH neuronal systems may be involved in reproductive or maternal function. MCH transcripts and MCH peptide were found within germ cells in testes of adult rats, suggesting that MCH may participate in stem cell renewal and/or differentiation of early spermatocytes (Hervieu et al., 1996). MCH injected directly into the medial preoptic area (MPOA) or ventromedial nucleus (V) stimulated sexual activity in female rats (Gonzalez et al., 1996). In ovariectomized rats primed with estradiol, MCH stimulated luteinizing hormone (LH) release while anti-MCH antiserum inhibited LH release (Gonzalez et al., 1997). The zona incerta, which contains a large population of MCH cell bodies, has previously been identified as a regulatory site for the pre-ovulatory LH surge (MacKenzie et al., 1984). Therefore modulators of MCH receptors may be useful in the prevention and treatment of reproductive function. MCH has been reported to influence release of pituitary hormones including ACTH and oxytocin. Therefore, modulators of MCH receptors may be useful in the prevention and treatment of obesity, Cushing's disease, sexual function, appetite and eating disorders, obesity, diabetes, cardiovascular disease, hypertension, dyslipidemia, myocardial infarction, gall stones, osteoarthritis, certain cancers, AIDS wasting, cachexia, frailty (particularly in the elderly), binge eating disorders including bulimia, anorexia, kidney function, diuresis, reproductive function and sexual function.

Two receptor subtypes have been identified in humans, MCH-1R and MCH-2R. Both receptors, as well as the gene for the MCH peptide, have been mapped to regions previously reported to contain a susceptibility gene for psychiatric disorders. In particular, MCH-1R was mapped to chromosome 22q13.2 (Kolakowski et al. 1996). The possibility of linkage for schizophrenia susceptibility locus in this area was suggested by independent studies from 2 groups (Pulver et al. 1994, Coon et al. 1994). In addition, a more recent study (Stoeber et al. 2000) of samples from patients with periodic catatonia, a clinical subtype of unsystematic schizophrenia suggested possible linkage of the region around 22q13. Human genetics implicates these loci not only for schizophrenia but also for bipolar disorder. The second MCH receptor (MCH-2R) has been mapped to chromosome 6q16.2–16.3 (Sailer et al., 2001). Cao et al. (1997) were the first to report evidence of a schizophrenia susceptibility locus in that area. This initial report was confirmed and extended by other reports (Martinez et al. 1999, Kaufmann et al. 1998, Levinson et al. 2000). Schizophrenia has been recognized as a disorder with profound deficits in information-processing and attentional abnormalities. One of the few possible paradigms available to assess these types of deficits in information processing is sensory gating, a filtering process which can be demonstrated by using a paired auditory stimulus. Miller et al. (1993) examined the effects of ICV administered MCH on the decrease in amplitude of the second of two tone-evoked CNS potentials that can be measured when pairs of identical tones are presented 500 ms apart. They found that MCH application decreased sensory gating in this paradigm. Based on pathogenesis and pathophysiology (reviewed in Lewis and Liebermann (2000)) several brain areas have been implicated in schizophrenia, all of which show high expression for MCH receptors: thalamus, midbrain, nucleus accumbens, temporolimbic, and prefrontal cortices. These studies and findings support the use of MCH receptor modulators in the treatment and prevention of schizophrenia.

Kelsoe et al. (2001) recently reported on a genome survey indicating a possible susceptibility locus for bipolar disorder identified on 22q (Kelsoe et al. 2001). The MCH gene which encodes the MCH pro-peptide was mapped to chromosome 12q23.1. This area has been identified by Morissette et al. (1999) in a genome wide scan for susceptibility loci for bipolar disorder in families in the Province of Quebec. In addition, Ewald et al. (1998) showed significant linkage to chromosome 12q23.1 (maximum lod score 3.37) in Danish families suffering from bipolar affective disorder. In addition, Presse et al. (1997) have shown that lithium, the "gold standard" and most appropriate initial treatment for the depressive phase of bipolar disorder, can alter MCH mRNA levels in NGF-treated PC12 cells by increasing mRNA stability. These studies and findings support the use of MCH receptor modulators in the treatment and prevention of bipolar disorder and depression.

Philippe and colleagues (1999) performed a genome-wide screen for a autism susceptibility gene and found suggestive linkage for the region of chromosome 6q16.2–16.3 (maximum lod score 2.23). This finding supports the use of MCH receptor modulators in the treatment of autism.

In all species studied to date, a major portion of the neurons of the MCH cell group occupies a rather constant location in those areas of the lateral hypothalamus and subthalamus where they lie and may be a part of some of the so-called "extrapyramidal" motor circuits. These involve substantial striato- and pallidofugal pathways involving the thalamus and cerebral cortex, hypothalamic areas, and reciprocal connections to subthalamic nucleus, substantia nigra, and mid-brain centers (Bittencourt et al., 1992). In their location, the MCH cell group may offer a bridge or mechanism for expressing hypothalamic visceral activity with appropriate and coordinated motor activity. Thus, modulators of MCH receptor function may be useful in the treatment and prevention of movement disorders, such as Parkinson's disease, Parkinson-like syndromes and Huntingdon's Chorea in which extrapyramidal circuits are known to be involved.

Human genetic linkage studies have located authentic hMCH loci on chromosome 12 (12q23–24) and the variant hMCH loci on chromosome 5 (5q12–13) (Pedeutour et al., 1994). Locus 12q23–24 coincides with a locus to which autosomal dominant cerebellar ataxia type II (SCA2) has been mapped (Auburger et al., 1992; Twells et al., 1992). This disease comprises neurodegenerative disorders, including an olivopontocerebellar atrophy. Furthermnore, the gene for Darier's disease, has been mapped to locus 12q23–24 (Craddock et al., 1993). Dariers' disease is characterized by abnormalities in keratinocyte adhesion and mental illnesses in some families. In view of the functional and neuroanatomical patterns of the MCH neural system in the rat and human brains, the MCH gene may represent a good candidate for SCA2 or Darier's disease. Therefore, modulators of MCH receptors may be useful in the treatment of mental disorders including manic depression, depression, schizophrenia, mood disorders, delirium, dementia, severe mental retardation, anxiety, stress, cognitive disorders, and dyskinesias including Parkinson's disease, Tourette's syndrome, Huntington's disease, cerebellar ataxia, and seizures.

Further, the gene responsible for chronic or acute forms of spinal muscular atrophies has been assigned to chromosome 5q12–13 using genetic linkage analysis (Melki et al., 1990; Westbrook et al., 1992). Therefore, modulators of MCH receptors may be useful in treating muscular dystrophy and dyskinesias, including Parkinson's disease, Tourette's syndrome, Huntington's disease, cerebellar ataxia, seizures, locomotor disorders, attention deficit disorder (ADD) and substance abuse disorders.

Still further, modulators of MCH receptor binding may also be useful in treating epilepsy. In the PTZ seizure model, injection of MCH prior to seizure induction prevented seizure activity in both rats and guinea pigs, suggesting that MCH-containing neurons may participate in the neural circuitry underlying PTZ-induced seizure (Knigge and Wagner, 1997). MCH has also been observed to affect behavioral correlates of cognitive functions. MCH treatment hastened extinction of the passive avoidance response in rats (McBride et al., 1994), raising the possibility that MCH receptor antagonists may be beneficial for memory storage and/or retention.

A role for MCH in the modulation or perception of pain is supported by the dense innervation of the periaqueductal grey (PAG) by MCH-positive fibers. MCH receptor modulators may be useful as antinociceptives or as analgesics, particularly for the treatment of neuropathic pain.

Finally, MCH may participate in the regulation of fluid intake. ICV infusion of MCH in conscious sheep produced diuretic, natriuretic, and kaliuretic changes in response to increased plasma volume (Parkes, 1996). Together with anatomical data reporting the presence of MCH in fluid regulatory areas of the brain, the results indicate that MCH may be an important peptide involved in the central control of fluid homeostasis in mammals. Therefore, modulators of MCH receptors may be useful in kidney function and diuresis.

PCT publication WO 01/21169 to Takeda discloses MCH antagonists of the structural formula shown below:

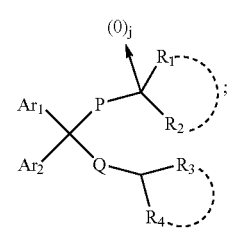

and PCT publication WO 01/21577 discloses MCH antagonists of the structural formula below:

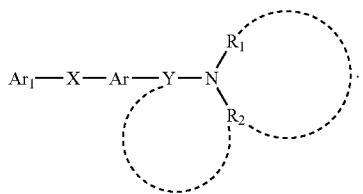

U.S. Pat. No. 4,701,459 and EP 0 252 503 disclose 2,3-dihydro-2-oxo-1H-imidazo[4,5-b]quinolinyl amine derivatives of structural formula:

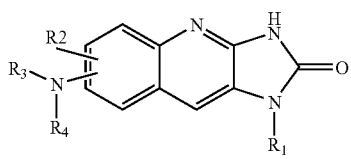

as useful in inhibiting blood platelet aggregation. U.S. Pat. No. 4,013,665 claims antiviral, substituted 1,3-dimethyl-1H-pyrazolo[3,4b]quinolines of structural formula below:

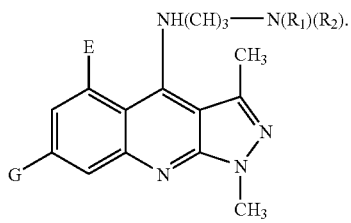

PCT publication WO 99/48492 discloses nociceptin antagonists of the formula below:

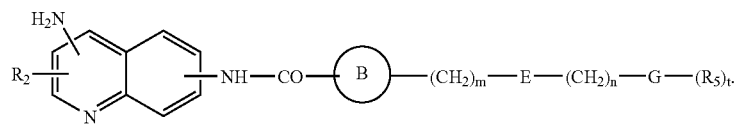

PCT publication WO 99/53924 discloses analgesic agent of the formula below:

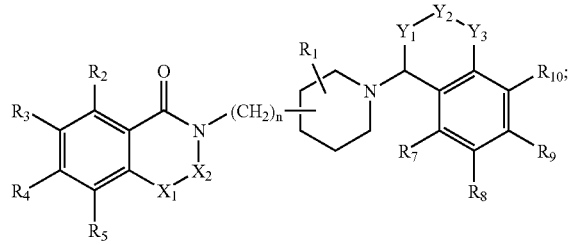

and PCT publication WO 99/19326 discloses compounds of the formula below:

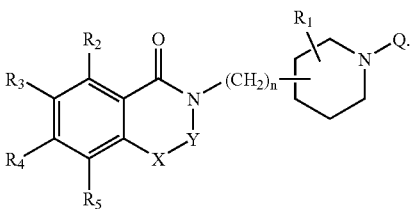

The compounds of the present invention are modulators of the MCH-1R receptor and are useful in the treatment, prevention and suppression of diseases mediated by the MCH-1R receptor. The invention is concerned with the use of these novel compounds to selectively antagonize the MCH-1R receptor. As such, compounds of the present invention are useful for the treatment or prevention of obesity, diabetes, appetite and eating disorders, cardiovascular disease, hypertension, dyslipidemia, myocardial infarction, gall stones, osteoarthritis, certain cancers, AIDS wasting, cachexia, frailty (particularly in elderly), binge eating disorders including bulimina, anorexia, mental disorders including manic depression, depression, schizophrenia, mood disorders, delirium, dementia, severe mental retardation, anxiety, stress, cognitive disorders, sexual function, reproductive function, kidney function, diuresis, locomotor disorders, attention deficit disorder (ADD), substance abuse disorders and dyskinesias including Parkinson's disease, Parkinson-like syndromes, Tourette's syndrome, Huntington's disease, epilepsy, improving memory function, and spinal muscular atrophy.

SUMMARY OF THE INVENTION

The present invention is concerned with compounds of the general Formula I:

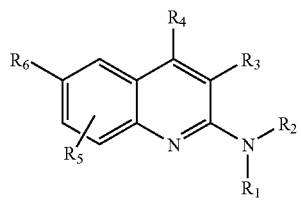

and pharmaceutically acceptable salts thereof, which are useful as melanin concentrating hormone (MCH) receptor antagonists.

As melanin concentrating hormone receptor antagonists, the compounds of the present invention are useful in the treatment, prevention and suppression of diseases mediated by the MCH receptor. In particular, certain compounds of the present invention are selective antagonists of the MCH-1R subtype receptor. As such, compounds of the present invention are useful for the treatment or prevention of obesity, diabetes, appetite and eating disorders, cardiovascular disease, hypertension, dyslipidemia, myocardial infarction, gall stones, osteoarthritis, certain cancers, AIDS wasting, cachexia, frailty (particularly in elderly), binge eating disorders including bulimina, anorexia, mental disorders including manic depression, depression, schizophrenia, mood disorders, delirium, dementia, severe mental retardation, anxiety, stress, cognitive disorders, sexual function, reproductive function, kidney function, diuresis, locomotor disorders, attention deficit disorder (ADD), substance abuse disorders and dyskinesias including Parkinson's disease, Parkinson-like syndromes, Tourette's syndrome, Huntington's disease, epilepsy, improving memory function, and spinal muscular atrophy.

In one embodiment of the present invention, $R^1$ is selected from:
(1) hydrogen,
(2) $C_{1-6}$ alkyl,
(3) $C_{2-6}$ alkenyl,
(4) $C_{2-6}$ alkynyl,
(5) cycloalkyl-$C_{0-6}$ alkyl,
(6) heterocycloalkyl-$C_{0-10}$ alkyl,
(7) aryl-$C_{1-10}$ alkyl, and
(8) heteroaryl-$C_{0-10}$ alkyl;

wherein alkyl, alkenyl, and alkynyl, moieties above are optionally substituted with one to four substituents independently selected from $R^a$, and cycloalkyl, heterocycloalkyl aryl and heteroaryl moieties above are optionally substituted with one to four substituents independently selected from $R^b$; and wherein sulfur-containing heterocyclic rings may be mono- or di-oxidized on the sulfur atom.

In one class of this embodiment of the present invention, $R^1$ is selected from:
(1) hydrogen,
(2) $C_{1-6}$ alkyl,
(3) $C_{2-6}$ alkenyl,
(4) cycloalkyl-$C_{0-6}$ alkyl,
(5) heterocycloalkyl-$C_{0-6}$ alkyl,
(6) aryl-$C_{0-6}$ alkyl, and
(7) heteroaryl-$C_{0-10}$ alkyl;

wherein alkyl and alkenyl moieties above are optionally substituted with one to three substituents independently selected from $R^a$, and cycloalkyl, heterocycloalkyl, aryl and heteroaryl moieties above are optionally substituted with one to three substituents independently selected from $R^b$.

In one subclass of this class of the invention, $R^1$ is hydrogen, or $C_{1-6}$ alkyl, optionally substituted with one to three substituents independently selected from $R^a$.

In another subclass of this class, $R^1$ is selected from:
(1) hydrogen,
(2) methyl,
(3) ethyl, and
(4) propyl, optionally substituted with one to three substituents independently selected from $R^a$.

In another subclass of this invention, $R^1$ is selected from:
(1) hydrogen, and
(2) methyl;

optionally substituted with one to three substituents independently selected from $R^a$.

In yet another subclass of this invention, $R^1$ is selected from:
(1) hydrogen, and
(2) methyl.

In one embodiment of the present invention, $R^2$ is selected from:
(1) hydrogen,
(2) $C_{1-6}$ alkyl,
(3) $C_{2-6}$ alkenyl,
(4) $C_{2-6}$ alkynyl,
(5) cycloalkyl-$C_{0-6}$ alkyl,
(6) heterocycloalkyl-$C_{0-10}$ alkyl,
(7) aryl-$C_{0-10}$ alkyl, and
(8) heteroaryl-$C_{0-10}$ alkyl;

wherein alkyl, alkenyl, and alkynyl, moieties above are optionally substituted with one to four substituents independently selected from $R^a$, and cycloalkyl, heterocycloalkyl aryl and heteroaryl moieties above are optionally substituted with one to four substituents independently selected from $R^b$; and wherein sulfur-containing heterocyclic rings may be mono- or di-oxidized on the sulfur atom.

In one class of this embodiment of the present invention, $R^2$ is selected from:
(1) hydrogen,
(2) $C_{1-6}$ alkyl,
(3) $C_{2-6}$ alkenyl,
(4) cycloalkyl-$C_{0-6}$ alkyl,
(5) heterocycloalkyl-$C_{0-6}$ alkyl,
(6) aryl-$C_{0-6}$ alkyl, and
(7) heteroaryl-$C_{0-10}$ alkyl;

wherein alkyl and alkenyl moieties above are optionally substituted with one to three substituents independently selected from $R^a$, and cycloalkyl, heterocycloalkyl, aryl and heteroaryl moieties above are optionally substituted with one to three substituents independently selected from $R^b$.

In one subclass of this class, $R^2$ is selected from:
(1) hydrogen,
(2) $C_{1-6}$ alkyl,
(3) cycloalkyl-$C_{0-6}$ alkyl,
(4) heterocycloalkyl-$C_{0-6}$ alkyl,
(5) aryl-$C_{0-6}$ alkyl, and
(6) heteroaryl-$C_{0-10}$ alkyl;

wherein alkyl moieties above are optionally substituted with one to three substituents independently selected from $R^a$, and cycloalkyl, heterocycloalkyl, aryl and heteroaryl moieties above are optionally substituted with one to three substituents independently selected from $R^b$.

In another subclass of this class, $R^2$ is selected from:
(1) hydrogen,
(2) $C_{1-6}$ alkyl,
(3) cycloalkyl-$C_{0-6}$ alkyl,
(4) heterocycloalkyl-$C_{0-6}$ alkyl, and
(5) aryl-$C_{0-6}$ alkyl, wherein alkyl moieties above are optionally substituted with one to three substituents independently selected from $R^a$, and cycloalkyl, heterocycloalkyl, aryl and heteroaryl moieties above are optionally substituted with one to three substituents independently selected from $R^b$.

In yet another subclass of this class, $R^2$ is selected from:
(1) methyl,
(2) ethyl,
(3) n-propyl,
(4) isopropyl,
(5) t-butyl,
(6) n-butyl, (7) cyclopropyl,
(8) cyclobutyl,
(9) cyclopentyl,
(10) cyclohexyl,
(11) heterocycloalkyl-$C_{0-6}$ alkyl, wherein the heterocycloalkyl moiety is selected from azetidinyl, pyrrolidinyl, and pyridyl and
(12) phenyl-$C_{0-6}$ alkyl, wherein alkyl moieties above are optionally substituted with one to three substituents independently selected from $R^a$, and cycloalkyl, heterocycloalkyl, and aryl moieties above are optionally substituted with one to three substituents independently selected from $R^b$.

In another embodiment of the present invention, when $R^1$ is hydrogen or 2-hydroxyethyl, $R^2$ is other than 4-methansulfonamidophenethyl.

In another embodiment of the present invention, $R^1$ and $R^2$ together with the nitrogen atom to which they are attached, form a 4- to 11-membered bridged or unbridged or spirocyclic heterocyclic ring, optionally containing one or two additional heteroatoms selected from N, S, and O, optionally having one or more degrees of unsaturation, optionally fused to a 6-membered heteroaromatic or aromatic ring, either unsubstituted or substituted with one to four substituents independently selected from $R^b$; and wherein sulfur-containing heterocyclic rings may be mono- or di-oxidized on the sulfur atom. In one class of this embodiment of the invention, $R^1$ and $R^2$ together with the nitrogen atom to which they are attached, form a 4- to 11-membered bridged or unbridged or spirocyclic heterocyclic ring, optionally containing one additional heteroatom selected from N, S, and O, optionally having one or more degrees of unsaturation, optionally fused to a 6-membered heteroaromatic or aromatic ring, either unsubstituted or substituted with an $R^b$ substituent. In one subclass of this class, $R^1$ and $R^2$ together with the nitrogen atom to which they are attached, form a 4- to 11-membered bridged or unbridged or spirocyclic heterocyclic ring, optionally containing one additional heteroatom selected from N, S, and 0, either unsubstituted or substituted with an $R^b$ substituent. In another subclass of this class, $R^1$ and $R^2$ together with the nitrogen atom to which they are attached, form a 4- to 11-membered bridged or unbridged or spirocyclic heterocyclic ring, selected from: azetidinyl, pyrrolidinyl, piperidinyl, morpholinyl, 1-thia-4-azacyclohexyl, 2,5-diazabicyclo[2.2.2]octanyl, azacycloheptyl, 2-oxa-5-azabicyclo[2.2.1]heptyl, 2,5-diazabicyclo[2.2.1]heptyl, 2-azabicyclo[2.2.1]heptyl, 7-azabicyclo[2.2.1]heptyl, 2,5-diazabicyclo[2.2.2]octyl, 2-azabicyclo[2.2.2]octyl, and 3-azabicyclo[3.2.2]nonyl, 2,7-diazaspiro[4.4]nonyl, 2,7-diazaspiro[4.5]decyl, 2,7-diazaspiro[4.6]undecyl, 1,7-diazaspiro[4.4]nonyl, 2,6-dizaospiro[4.5]decyl, 2,6-diazaspiro[4.6]-undecyl, either unsubstituted or substituted with an $R^b$ substituent.

In yet another embodiment of the present invention, $R^3$ is selected from:
(1) hydrogen,
(2) halogen,
(3) $C_{1-8}$ alkyl,
(4) perfluoro $C_{1-6}$ alkyl,
(5) $C_{2-6}$ alkenyl,
(6) $C_{2-6}$ alkynyl,
(7) cycloalkyl,
(8) cycloalkyl-$C_{1-6}$ alkyl,
(9) cycloheteroalkyl,
(10) cycloheteroalkyl-$C_{1-6}$ alkyl,
(11) aryl,
(12) aryl-$C_{1-6}$ alkyl,
(13) heteroaryl,
(14) heteroaryl-$C_{1-6}$ alkyl,
(15) —$OR^7$,
(16) —$NR^7R^7$,
(17) —$CO_2R^7$,
(18) cyano, and
(19) —$C(O)NR^7R^7$;

wherein alkyl, alkenyl and alkynyl, moieties above are optionally substituted with one to four substituents independently selected from $R^a$, and cycloalkyl, heterocycloalkyl, aryl and heteroaryl moieties above are optionally substituted with one to four substituents independently selected from $R^b$; and wherein sulfur-containing heterocyclic rings may be mono- or di-oxidized on the sulfur atom.

In one class of this embodiment of the present invention, $R^3$ is selected from:
(1) hydrogen,
(2) halogen,
(3) $C_{1-8}$ alkyl,
(4) trifluoromethyl,
(5) $C_{2-6}$ alkenyl,
(6) cycloalkyl,
(7) cycloalkyl-$C_{1-6}$ alkyl,
(8) cycloheteroalkyl,
(9) cycloheteroalkyl-$C_{1-6}$ alkyl,
(10) aryl,
(11) aryl-$C_{1-6}$ alkyl,
(12) heteroaryl,
(13) heteroaryl-$C_{1-6}$ alkyl,
(14) —$OR^7$,
(15) —$NR^7R^7$,
(16) —$CO_2R^7$, and
(17) —$C(O)NR^7R^7$;

wherein alkyl and alkenyl moieties above are optionally substituted with one to three substituents independently selected from $R^a$, and cycloalkyl, heterocycloalkyl, aryl and heteroaryl moieties above are optionally substituted with an $R^b$ substituent.

In one subclass of this class, $R^3$ is selected from:
(1) hydrogen,
(2) halogen,
(3) $C_{1-8}$ alkyl,
(4) trifluoromethyl,
(5) —OH,
(6) —$OCH_3$,
(7) —$NH_2$,
(8) —$CO_2R^7$, and
(9) —$C(O)NH_2$;

wherein alkyl moieties above are optionally substituted with one to two substituents independently selected from $R^a$.

In another subclass of this class, $R^3$ is selected from:
(1) hydrogen,
(2) halogen,
(3) $C_{1-8}$ alkyl, and
(4) trifluoromethyl, wherein alkyl moieties above are optionally substituted with one to two substituents independently selected from $R^a$.

In yet another subclass of this class, $R^3$ is selected from:
(1) hydrogen,
(2) halogen,
(3) methyl,
(4) ethyl,
(5) propyl, and
(6) trifluoromethyl, wherein alkyl moieties above are optionally substituted with one to two substituents independently selected from $R^a$;

In still another embodiment of the present invention, $R^4$ is selected from:
(1) hydrogen,
(2) halogen,
(3) $C_{1-8}$ alkyl,
(4) perfluoro $C_{1-6}$ alkyl,
(5) $C_{2-6}$ alkenyl,
(6) $C_{2-6}$ alkynyl,
(7) cycloalkyl,
(8) cycloalkyl-$C_{1-6}$ alkyl,
(9) cycloheteroalkyl,
(10) cycloheteroalkyl-$C_{1-6}$ alkyl,
(11) aryl,
(12) aryl-$C_{1-6}$ alkyl,
(13) heteroaryl,
(14) heteroaryl-$C_{1-6}$ alkyl,
(15) —$OR^7$,
(16) —$NR^7R^7$,
(17) —$CO_2R^7$, and
(18) —$C(O)NR^7R^7$;

wherein alkyl, alkenyl and alkynyl, moieties above are optionally substituted with one to four substituents independently selected from $R^a$, and cycloalkyl, heterocycloalkyl, aryl and heteroaryl moieties above are optionally substituted with one to four substituents independently selected from $R^b$; and wherein sulfur-containing heterocyclic rings may be mono- or di-oxidized on the sulfur atom.

In one class of this embodiment of the present invention, $R^4$ is selected from:
(1) hydrogen,
(2) halogen,
(3) $C_{1-8}$ alkyl,
(4) trifluoromethyl,
(5) $C_{2-6}$ alkenyl,
(6) cycloalkyl,
(7) cycloalkyl-$C_{1-6}$ alkyl,
(8) cycloheteroalkyl,
(9) cycloheteroalkyl-$C_{1-6}$ alkyl,
(10) aryl,
(11) aryl-$C_{1-6}$ alkyl,
(12) heteroaryl,
(13) heteroaryl-$C_{1-6}$ alkyl,
(14) —$OR^7$,
(15) —$NR^7R^7$,
(16) —$CO_2R^7$, and
(17) —$C(O)NR^7R^7$;

wherein alkyl and alkenyl moieties above are optionally substituted with one to three substituents independently selected from $R^a$, and cycloalkyl, heterocycloalkyl, aryl and heteroaryl moieties above are optionally substituted with an $R^b$ substituent.

In one subclass of this class of the invention, $R^4$ is selected from:
(1) hydrogen,
(2) halogen,
(3) $C_{1-8}$ alkyl,
(4) trifluoromethyl,
(5) cycloalkyl,
(6) cycloheteroalkyl,
(7) aryl,
(8) aryl-$C_{1-6}$ alkyl,
(9) heteroaryl,
(10) —OH,
(11) —$OCH_3$,
(12) —$NH_2$,
(13) —$CO_2R^7$, and
(14) —$C(O)NH_2$;

wherein alkyl moieties above are optionally substituted with one to four substituents independently selected from $R^a$, and cycloalkyl, heterocycloalkyl, aryl and heteroaryl moieties above are optionally substituted with an $R^b$ substituent.

In another subclass of this class of the invention, $R^4$ is selected from:
(1) hydrogen,
(2) $C_{1-8}$ alkyl,
(3) trifluoromethyl,
(4) cycloalkyl,
(5) cycloheteroalkyl,
(6) aryl,
(7) heteroaryl,
(8) —$NH_2$,
(9) —$CO_2H$,
(10) —$CO_2CH_3$ and
(11) —$CO_2CH_2CH_3$;

wherein alkyl moieties above are optionally substituted with one to two substituents independently selected from $R^a$, and cycloalkyl, heterocycloalkyl, aryl and heteroaryl moieties above are optionally substituted with an $R^b$ substituent.

In yet another subclass of this class of the invention, $R^4$ is selected from:
(1) hydrogen,
(2) methyl,
(3) ethyl,
(4) propyl,
(5) trifluoromethyl,
(6) —$CO_2H$,
(7) —$CO_2CH_3$ and
(8) —$CO_2CH_2CH_3$;

wherein alkyl moieties above are optionally substituted with one to three substituents independently selected from $R^a$.

In still another subclass of this class of the invention, $R^4$ is selected from:
(1) Hydrogen,
(2) methyl,
(3) ethyl,
(4) —$CO_2H$, and
(5) —$CO_2CH_3$.

In another embodiment of the present invention, $R^3$ and $R^4$ together with the ring carbon atoms to which they are attached, form a 5- to 7-membered heterocycloalkyl or cycloalkyl ring, either unsubstituted or substituted with one to four substituents independently selected from $R_b$. In one class of this embodiment of the present invention, $R^3$ and $R^4$ together with the ring carbon atoms to which they are attached, form a 5- to 7-membered heterocycloalkyl or cycloalkyl ring, either unsubstituted or substituted with an $R^b$ substituent. In one subclass of this class, $R^3$ and $R^4$ together with the ring carbon atoms to which they are attached, form cyclohexyl ring, either unsubstituted or substituted with an $R^b$ substituent. In another subclass of this class, $R^3$ and $R^4$ together with the ring carbon atoms to which they are attached, form a cyclohexyl ring, either unsubstituted or substituted with oxo or hydroxy.

In one embodiment of the present invention, $R^5$ is selected from:
(1) hydrogen,
(2) halogen,
(3) $C_{1-6}$ alkyl,
(4) perfluoro $C_{1-6}$ alkyl, (5) —OR$^7$, and
(6) —NR$^7$R$^7$.

In one class of this embodiment of the present invention, R$^5$ is selected from:
(1) hydrogen,
(2) halogen,
(3) methyl,
(4) trifluoromethyl,
(5) hydroxy,
(6) methoxy,
(7) phenoxy,
(8) —NH$_2$,
(9) —NH(CH$_3$), and
(10) —N(CH$_3$)$_2$.

In one class of this embodiment of the invention, R$^5$ is selected from:
(1) hydrogen,
(2) halogen,
(3) methyl,
(4) trifluoromethyl,
(5) hydroxy,
(6) methoxy,
(7) phenoxy,
(8) —NH$_2$,
(9) —NH(CH$_3$), and
(10) —N(CH$_3$)$_2$.

In one subclass of this class, R$^5$ is selected from:
(1) hydrogen,
(2) halogen,
(3) methyl,
(4) trifluoromethyl,
(5) hydroxy, and
(6) methoxy.

In another subclass of this class, R$^5$ is hydrogen.

In another embodiment of the present invention, R$^6$ is selected from:
(1) —(CH$_2$)$_n$—R$^7$,
(2) —(CH$_2$)$_n$-aryl-R$^7$,
(3) —(CH$_2$)$_n$-heteroaryl-R$^7$,
(4) —(CH$_2$)$_n$-heterocycloalkyl-R$^7$,
(5) —(CH$_2$)$_n$C≡N,
(6) —(CH$_2$)$_n$CON(R$^7$)2,
(7) —(CH$_2$)$_n$CO$_2$R$^7$,
(8) —(CH$_2$)$_n$COR$^7$,
(9) —(CH$_2$)$_n$NR$^7$C(O)R$^7$,
(10) —(CH$_2$)$_n$NR$^7$C(O)(CH$_2$)$_n$SR$^7$
(11) —(CH$_2$)$_n$NR$^7$CO$_2$R$^7$,
(12) —(CH$_2$)$_n$NR$^7$C(O)N(R$^7$)$_2$,
(13) —(CH$_2$)$_n$NR$^7$SO$_2$R$^7$,
(14) —(CH$_2$)$_n$S(O)$_2$R$^7$,
(15) —(CH$_2$)$_n$SO$_2$N(R$^7$)$_2$,
(16) —(CH$_2$)$_n$OR$^7$,
(17) —(CH$_2$)$_n$OC(O)R$^7$,
(18) —(CH$_2$)$_n$OC(O)OR$^7$,
(19) —(CH$_2$)$_n$OC(O)N(R$^7$)$_2$,
(20) —(CH$_2$)$_n$N(R$^7$)$_2$, and
(21) —(CH$_2$)$_n$NR$^7$SO$_2$N(R$^7$)$_2$, wherein one or two of the hydrogen atoms in (CH$_2$)$_n$ may be substituted with R$^a$.

In one class of this embodiment of the present invention, R$^6$ is selected from:
(1) —(CH$_2$)$_n$—R$^7$,
(2) —(CH$_2$)$_n$-aryl-R$^7$,
(3) —(CH$_2$)$_n$-heteroaryl-R$^7$,
(4) —(CH$_2$)$_n$-heterocycloalkyl-R$^7$,
(5) —(CH$_2$)$_n$CON(R$^7$)$_2$,
(6) —(CH$_2$)$_n$NR$^7$C(O)R$^7$,
(7) —(CH$_2$)$_n$NR$^7$C(O)(CH$_2$)$_n$SR$^7$
(8) —(CH$_2$)$_n$NR$^7$C(O)N(R$^7$)$_2$,
(9) —(CH$_2$)$_n$NHSO$_2$R$^7$,
(10) —(CH$_2$)$_n$N(R$^7$)$_2$, and
(11) —(CH$_2$)$_n$NR$^7$SO$_2$N(R$^7$)$_2$, wherein one or two of the hydrogen atoms in (CH$_2$)$_n$ may be substituted with R$^a$.

In one subclass of this class, R$^6$ is selected from:
(1) —R$^7$,
(2) -heteroaryl-R$^7$,
(3) —CON(R$^7$)(CH$_3$),
(4) —CH$_2$CONHR$^7$,
(5) —CH$_2$CON(R$^7$)(CH$_3$),
(6) —CH$_2$NHC(O)R$^7$,
(7) —NHC(O)R$^7$,
(8) —(CH$_2$)$_n$NHC(O)(CH$_2$)$_n$SR$^7$,
(9) —(CH$_2$)$_n$NHC(O)N(CH$_3$)(R$^7$),
(10) —(CH$_2$)$_n$NHC(O)NH(R$^7$),
(11) —(CH$_2$)$_n$NHSO$_2$R$^7$,
(12) —NH(R$^7$),
(13) —N(COCH$_3$)(R$^7$),
(14) —(CH$_2$)$_n$NH(R$^7$), and
(15) —(CH$_2$)$_n$N(COCH$_3$)(R$^7$), wherein one or two of the hydrogen atoms in (CH$_2$)$_n$ may be substituted with R$^a$.

In yet another embodiment of the present invention, R$^7$ is independently selected at each occurrence from:
(1) hydrogen,
(2) C$_{1-6}$ alkyl,
(3) aryl,
(4) heteroaryl,
(5) cycloalkyl,
(6) heterocycloalkyl,
(7) aryl C$_{1-3}$ alkyl,
(8) heteroaryl C$_{1-3}$ alkyl,
(9) cycloalkyl C$_{1-3}$ alkyl,
(10) heterocycloalkyl C$_{1-3}$ alkyl,
(11) aryl C$_{2-3}$ alkenyl,
(12) heteroaryl C$_{2-3}$ alkenyl,
(13) cycloalkyl C$_{2-3}$ alkenyl, and
(14) heterocycloalkyl C$_{2-3}$ alkenyl, wherein the alkyl and alkenyl moieties are optionally substituted with one to four substituents selected from R$^a$, and wherein the aryl, heteroaryl, cycloalkyl and heterocycloalkyl moieties are independently substituted with one to four substituents selected from R$^b$; and wherein sulfur-containing heterocyclic rings may be mono- or di-oxidized on the sulfur atom.

In one class of this embodiment of the invention, the alkyl and alkenyl moieties in R$^7$ are optionally substituted with one to three substituents selected from R$^a$, and wherein the aryl, heteroaryl, cycloalkyl and heterocycloalkyl moieties in R$^7$ are independently substituted with one to three substituents selected from R$^b$; and wherein sulfur-containing heterocyclic rings may be mono- or di-oxidized on the sulfur atom.

In another class of this embodiment of the invention, R$^7$ is independently selected at each occurrence from:
(1) hydrogen,
(2) C$_{1-6}$ alkyl,
(3) aryl, selected from: phenyl, naphthyl, indanyl, indenyl, indolyl, quinazolinyl, quinolinyl, benzthiazolyl, benzoxazolyl, dihydroindanyl, benzisodiazolyl, spirocyclohexylindolinyl, spiro-(dihydrobenzothiophenyl)piperidinyl, spiro-indolinylpiperidinyl, indolinyl, tetrahydroisoquinolinyl, isoindolinyl, benzothiadiazolyl, benzotriazolyl, 1,3-dihydro-2-benzofuranyl, benzothiophenyl, benzodioxolyl, tetrahydronaphthyl, 2,3-dihydrobenzofuranyl, dihydrobenzopyranyl, and 1,4-benzodioxanyl, (4) heteroaryl, selected from: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo[2,3-b]pyridyl, quinolyl, indolyl, isoquinolyl, quinazolinyl, benzisodiazolyl, triazolopyrimidinyl, 5,6,7,8-tetrahydroquinolinyl, 2,1,3-benzothiadiazolyl, and thienopyridinyl, (5) cycloalkyl, selected from: cyclopropyl, cyclobutyl, cyclopentyl, cyclohexyl, cycloheptyl, tetrahydronaphthyl, decahydronaphthyl, indanyl, bicyclo[2.2.2]octanyl, tetrahydronaphthyl, and dihydroindanyl, (6) heterocycloalkyl, selected from: azetidinyl, pyridyl, pyrrolidinyl, piperidinyl, piperazinyl, imidazolidinyl, morpholinyl, 1-thia-4-aza-cyclohexane, 2,5-diazabicyclo[2.2.2]octanyl, 2,3-dihydrofuro[2,3-b]pyridyl, benzoxazinyl, tetrahydroquinolinyl, tetrahydroisoquinolinyl, dihydroindolyl, indolyl, indolinyl, isoindolinyl, 1,3-dihydro-2-benzofuranyl, benzodioxolyl, hexahydrothienopyridinyl, thienopyridinyl, azacycloheptyl, 4,4-spiro[2,3-dihydrobenzothiophen-3,3-yl]piperidinyl, and 4,4-spiro[indoli-3,3-yl]piperidinyl, (7) aryl $C_{1-3}$ alkyl, wherein the aryl moiety is selected from: phenyl, naphthyl, indanyl, indenyl, indolyl, quinazolinyl, quinolinyl, benzthiazolyl, benzoxazolyl, dihydroindanyl, benzisodiazolyl, spirocyclohexylindolinyl, spiro-(dihydrobenzothiophenyl)piperidinyl, spiro-indolinylpiperidinyl, indolinyl, tetrahydroisoquinolinyl, isoindolinyl, benzothiadiazolyl, benzotriazolyl, 1,3-dihydro-2-benzofuranyl, benzothiophenyl, benzodioxolyl, tetrahydronaphthyl, 2,3-dihydrobenzofuranyl, dihydrobenzopyranyl, and 1,4-benzodioxanyl, (8) heteroaryl $C_{1-3}$ alkyl, wherein the heteroaryl moiety is selected: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo[2,3-b]pyridyl, quinolyl, indolyl, isoquinolyl, quinazolinyl, benzisodiazolyl, triazolopyrimidinyl, 5,6,7,8-tetrahydroquinolinyl, 2,1,3-benzothiadiazolyl, and thienopyridinyl, (9) cycloalkyl $C_{1-3}$ alkyl, wherein the cycloalkyl moiety is selected from: cyclopropyl, cyclobutyl, cyclopentyl, cyclohexyl, cycloheptyl, tetrahydronaphthyl, decahydronaphthyl, indanyl, bicyclo[2.2.2]octanyl, tetrahydronaphthyl, and dihydroindanyl,

(10) heterocycloalkyl $C_{1-3}$ alkyl, wherein the heterocycloalkyl moiety is selected from: azetidinyl, pyridyl, pyrrolidinyl, piperidinyl, piperazinyl, imidazolidinyl, morpholinyl, 1-thia-4-aza-cyclohexane, 2,5-diazabicyclo[2.2.2]octanyl, 2,3-dihydrofuro[2,3-b]pyridyl, benzoxazinyl, tetrahydroquinolinyl, tetrahydroisoquinolinyl, dihydroindolyl, indolyl, indolinyl, isoindolinyl, 1,3-dihydro-2-benzofuranyl, benzodioxolyl, hexahydrothienopyridinyl, thienopyridinyl, azacycloheptyl, 4,4-spiro[2,3-dihydrobenzothiophen-3,3-yl]piperidinyl, and 4,4-spiro[indoli-3,3-yl]piperidinyl,

(11) aryl $C_{2-3}$ alkenyl, wherein the aryl moiety is selected from: phenyl, naphthyl, indanyl, indenyl, indolyl, quinazolinyl, quinolinyl, benzthiazolyl, benzoxazolyl, dihydroindanyl, benzisodiazolyl, spirocyclohexylindolinyl, spiro-(dihydrobenzothiophenyl)piperidinyl, spiro-indolinylpiperidinyl, indolinyl, tetrahydroisoquinolinyl, isoindolinyl, benzothiadiazolyl, benzotriazolyl, 1,3-dihydro-2-benzofuranyl, benzothiophenyl, benzodioxolyl, tetrahydronaphthyl, 2,3-dihydrobenzofuranyl, dihydrobenzopyranyl, and 1,4-benzodioxanyl,

(12) heteroaryl $C_{2-3}$ alkenyl, wherein the heteroaryl moiety is selected from: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo[2,3-b]pyridyl, quinolyl, indolyl, isoquinolyl, quinazolinyl, benzisodiazolyl, triazolopyrimidinyl, 5,6,7,8-tetrahydroquinolinyl, 2,1,3-benzothiadiazolyl, and thienopyridinyl,

(13) cycloalkyl $C_{2-3}$ alkenyl, wherein the cycloalkyl moiety is selected from: cyclopropyl, cyclobutyl, cyclopentyl, cyclohexyl, cycloheptyl, tetrahydronaphthyl, decahydronaphthyl, indanyl, bicyclo[2.2.2]octanyl, tetrahydronaphthyl, and dihydroindanyl, and

(14) heterocycloalkyl $C_{2-3}$ alkenyl, wherein the heterocycloalkyl moiety is selected from: azetidinyl, pyridyl, pyrrolidinyl, piperidinyl, piperazinyl, imidazolidinyl, morpholinyl, 1-thia-4-aza-cyclohexane, 2,5-diazabicyclo[2.2.2]octanyl, 2,3-dihydrofuro[2,3-b]pyridyl, benzoxazinyl, tetrahydroquinolinyl, tetrahydroisoquinolinyl, dihydroindolyl, indolyl, indolinyl, isoindolinyl, 1,3-dihydro-2-benzofuranyl, benzodioxolyl, hexahydrothienopyridinyl, thienopyridinyl, azacycloheptyl, 4,4-spiro[2,3-dihydrobenzothiophen-3,3-yl]piperidinyl, and 4,4-spiro[indoli-3,3-yl]piperidinyl;

wherein the alkyl moieties are optionally substituted with one to three substituents selected from $R^a$, and wherein the aryl, heteroaryl, cycloalkyl and heterocycloalkyl moieties are independently substituted with one to three substituents selected from $R^b$; and wherein sulfur-containing heterocyclic rings may be mono- or di-oxidized on the sulfur atom.

In another embodiment of the present invention, $R^a$ is independently selected from:

(1) —$OR^d$,
(2) —$NR^d S(O)_m R^d$,
(3) —$NO_2$,
(4) halogen,
(5) —$S(O)_m R^d$,
(6) —$SR^d$,
(7) —$S(O)_2 OR^d$,
(8) —$S(O)_p N(R^d)_2$,
(9) —$N(R^d)_2$,
(10) —$O(CR^d R^d)_n N(R^d)_2$,
(11) —$C(O)R^d$,
(12) —$CO_2 R^d$,
(13) —$CO_2(CR^d R^d)_n CON(R^d)_2$,
(14) —$OC(O)R^d$,
(15) —CN,
(16) —$C(O)N(R^d)_2$,
(17) —$NR^d C(O)R^d$,
(18) —$OC(O)N(R^d)_2$,
(19) —$NR^d C(O)OR^d$,
(20) —$NR^d C(O)N(R^d)_2$,
(21) —$CR^d(N—OR^d)$,
(22) —$CF_3$,
(23) cycloalkyl,

(24) cycloheteroalkyl, and
(25) oxo;
at each occurrence.

In one class of this embodiment of the present invention, each $R^a$ is independently selected from:
(1) —$OR^d$,
(2) —$NHSO_2CH_3$,
(3) —$NO_2$,
(4) halogen,
(5) —$S(O)_mCH_3$,
(6) —$SCH_3$,
(7) —$SCF_3$,
(8) —$S(O)_2OR^d$,
(9) —$S(O)_pN(R^d)_2$,
(10) —$N(CH_3)_2$,
(11) —$NH_2$,
(12) —$O(CR^dR^d)_nN(R^d)_2$,
(13) —$C(O)R^d$,
(14) —$CO_2H$,
(15) —$CO_2CH_3$,
(16) t-butyloxycarbonyl,
(17) —$CO_2(CR^dR^d)_nCON(R^d)_2$,
(18) —$OC(O)R^d$,
(19) —CN,
(20) —$C(O)N(R^d)_2$,
(21) —$NR^dC(O)R^d$,
(22) —$OC(O)N(R^d)_2$,
(23) —$NR^dC(O)OR^d$,
(24) —$NR^dC(O)N(R^d)_2$,
(25) —$CR^d(N-OR^d)$,
(26) —$CF_3$,
(27) cycloalkyl,
(28) cycloheteroalkyl, and
(29) oxo.

In another embodiment of the present invention, each $R^b$ is independently selected from:
(1) $R^a$,
(2) —$Sn(CH_3)_3$,
(3) $C_{1-10}$ alkyl,
(4) $C_{2-10}$ alkenyl,
(5) $C_{2-10}$ alkynyl,
(6) heteroaryl,
(7) aryl, and
(8) aryl-$C_{1-10}$ alkyl;
wherein alkyl, alkenyl, alkynyl, cycloalkyl, cycloheteroalkyl, heteroaryl, and aryl are optionally substituted with one to four $R^c$ substituents.

In one class of this embodiment of the present invention, each $R^b$ is independently selected from:
(1) $R^a$,
(2) —$Sn(CH_3)_3$,
(3) $C_{1-10}$ alkyl,
(4) $C_{2-10}$ alkenyl,
(5) heteroaryl,
(6) aryl, and
(7) aryl-$C_{1-10}$ alkyl;
wherein alkyl, alkenyl, cycloalkyl, cycloheteroalkyl, heteroaryl, and aryl are optionally substituted with one to four substituents selected from a group independently selected from $R^c$.

In one subclass of this class, each $R^b$ is independently selected from:
(1) $R^a$,
(2) —$Sn(CH_3)_3$,
(3) $C_{1-6}$ alkyl,
(4) $C_{2-6}$ alkenyl,
(5) heteroaryl,
(6) aryl, and
(7) aryl-$C_{1-10}$ alkyl;
wherein alkyl, alkenyl, cycloalkyl, cycloheteroalkyl, heteroaryl, and aryl moieties in $R^a$ and $R^b$ are optionally substituted with one to four substituents independently selected from $R^c$.

In yet another embodiment of the present invention, each $R^c$ is independently selected from:
(1) halogen,
(2) amino,
(3) carboxy,
(4) $C_{1-4}$ alkyl,
(5) $C_{1-4}$ alkoxy,
(6) aryl,
(7) aryl $C_{1-4}$ alkyl,
(8) hydroxy,
(9) —$CF_3$,
(10) —$OC(O)C_{1-4}$ alkyl,
(11) —$OC(O)N(R^d)_2$, and
(12) aryloxy.

In still another embodiment of the present invention, $R^d$ is independently selected from hydrogen, $C_{1-6}$ alkyl, $C_{2-6}$ alkenyl; $C_{2-6}$ alkynyl; cycloalkyl; cycloalkyl-$C_{1-6}$ alkyl; cycloheteroalkyl; cycloheteroalkyl-$C_{1-6}$ alkyl; aryl; heteroaryl; aryl-$C_{1-6}$ alkyl; and heteroaryl-$C_{1-6}$ alkyl; wherein the alkyl, alkenyl, alkynyl, cycloalkyl, cycloheteroalkyl, heteroaryl, and aryl in $R^d$ are optionally substituted with one to four substituents independently selected from $R^e$. In one class of this embodiment of the present invention, the alkyl, alkenyl, alkynyl, cycloalkyl, cycloheteroalkyl, heteroaryl, and aryl in $R^d$ are optionally substituted with one to two substituents independently selected from a $R^e$.

In another embodiment of the present invention, each $R^e$ is selected from halo, methyl, methoxy, trifluoromethyl, trifluoromethoxy, and hydroxy.

In still another embodiment of the present invention, each m is independently selected from 1 and 2. In one class of this embodiment, m is 1. In another class of this embodiment m is 2.

In yet another embodiment of the present invention, n is independently elected from 0, 1, 2, 3, 4, and 5 at each occurrence. In one class of this embodiment, each n is independently selected from 0, 1, 2, 3, and 4. In one subclass of this class, n is selected from 0, 1, 2, and 3. In another subclass of this class, n is selected from 0, 1, and 2. In still another subclass of this class, n is 0.

In still another embodiment of the present invention, each p is independently selected from 0, 1, and 2. In one class of this embodiment, p is 0. In another class of this embodiment, p is 1. In still another class of this embodiment, p is 2.

As MCH-1R antagonists, the compounds of the present invention may be useful in treating the following conditions: obesity, diabetes, appetite and eating disorders, cardiovascular disease, hypertension, dyslipidemia, myocardial infarction, gall stones, osteoarthritis, certain cancers, AIDS wasting, cachexia, frailty (particularly in elderly), binge eating disorders including bulimina, anorexia, mental disorders including manic depression, depression, schizophrenia, mood disorders, delirium, dementia, severe mental retardation, anxiety, stress, cognitive disorders, sexual function, reproductive function, kidney function, diuresis, locomotor disorders, attention deficit disorder (ADD), substance abuse disorders and dyskinesias including Parkinson's disease, Parkinson-like syndromes, Tourette's syndrome, Huntington's disease, epilepsy, improving memory function, and spinal muscular atrophy.

The present invention is also concerned with treatment of these conditions, and the use of compounds of the present invention for manufacture of a medicament useful in treating these conditions.

The invention is also concerned with pharmaceutical formulations comprising one of the compounds as an active ingredient.

The invention is further concerned with processes for preparing the compounds of this invention.

DETAILED DESCRIPTION OF THE INVENTION

The compounds of this invention are represented by the compound of structural formula I:

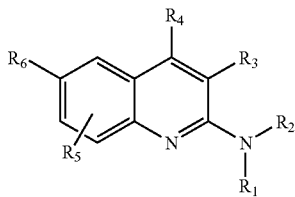

and pharmaceutically acceptable salts thereof.

"Alkyl", as well as other groups having the prefix "alk", such as alkoxy, alkanoyl, means carbon chains which may be linear or branched or combinations thereof. Examples of alkyl groups include methyl, ethyl, n-propyl, isopropyl, n-butyl, 1-methylpropyl, 2-methylpropyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 3-ethylbutyl, 1,1-dimethyl butyl, 1,2-dimethylbutyl, 1,3-dimethylbutyl, 2,2-dimethylbutyl, 2,3-dimethylbutyl, 3,3-dimethyl butyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1-propylbutyl, 2-propylbutyl, 3-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl. 2,4-dimethylpentyl, 3,3-dimethylpentyl, 3,4-dimethylpentyl, 4,4-dimethylpentyl, 1-methyl-1-ethylbutyl, 1-methyl-2-ethylbutyl, 2-methyl-2-ethylbutyl, 1-ethyl-2-methylbutyl, 1-ethyl-3-methylbutyl, 1,1-diethylpropyl, n-octyl, n-nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, bicyclo[2.2.2]octanyl, tetrahydronaphthyl, dihydroindanyl, 3,3-spirohexylindoline, 5,6,7,8-tetrahydroquinoline, and the like.

"Aryl" means mono- or bicyclic aromatic rings containing only carbon atoms. The term also includes aryl group fused to a monocyclic cycloalkyl or monocyclic heterocycloalkyl group in which the point of attachment is on the aromatic portion. Examples of aryl include phenyl, naphthyl, indanyl, indenyl, indolyl, quinazolinyl, quinolinyl, benzthiazolyl, benzoxazolyl, dihydroindanyl, benzisodiazolyl, spirocyclohexylindolinyl, spiro-(dihydrobenzothiophenyl)piperidinyl, spiro-indolinylpiperidinyl, indolinyl, tetrahydroisoquinolinyl, isoindolinyl, benzothiadiazolyl, benzotriazolyl, 1,3-dihydro-2-benzofuranyl, benzothiophenyl, benzodioxolyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5- to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo[2,3-b]pyridyl, quinolyl, indolyl, isoquinolyl, quinazolinyl, benzisodiazolyl, triazolopyrimidinyl, 5,6,7,8-tetrahydroquinolinyl, 2,1,3-benzothiadiazolyl, thienopyridinyl, and the like.

"Heterocycloalkyl" means mono- or bicyclic saturated rings containing at least one heteroatom selected from N, S and O, each of said ring having from 3 to 14 atoms in which the point of attachment may be carbon or nitrogen. The term also refers to bridged rings, includes monocyclic heterocycles fused to an aryl or heteroaryl group in which the point of attachment is on the non-aromatic portion, and also includes spirocyclic rings in which the point of attachment is via a heterocyclic ring. Examples of "heterocycloalkyl" include azetidinyl, pyridyl, pyrrolidinyl, piperidinyl, piperazinyl, imidazolidinyl, morpholinyl, 1-thia-4-aza-cyclohexane, 2,5-diazabicyclo[2.2.2]octanyl, 2,3-dihydrofuro[2,3-b]pyridyl, benzoxazinyl, tetrahydroquinolinyl, tetrahydroisoquinolinyl, dihydroindolyl, indolyl, indolinyl, isoindolinyl, 1,3-dihydro-2-benzofuranyl, benzodioxolyl, hexahydrothienopyridinyl, thienopyridinyl, azacycloheptyl, 2-oxa-5-azabicyclo[2.2.1]heptyl, 2,5-diazabicyclo[2.2.1]heptyl, 2-azabicyclo[2.2.1]heptyl, 7-azabicyclo[2.2.1.]heptyl, 2,4-dizaobicyclo[2.2.2]octyl, 2-azabicyclo[2.2.2]octyl, 3-azabicyclo[3,2.2]nonyl, 2H-pyrrolyl, 4,4-spiro[2,3-dihydrobenzothiophen-3,3-yl]piperidinyl, 4,4-spiro[indoli-3,3-yl]piperidinyl, 2,7-diazaspiro[4.4]nonyl, 2,7-diazaspiro[4.5]decyl, 2,7-diazaspiro[4.6]undecyl, 1,7-diazaspiro[4.4]nonyl, 2,6-dizaospiro[4.5]decyl, 2,6-diazaspiro[4.6]-undecyl and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" includes fluorine, chlorine, bromine and iodine.

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixtures thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column. Alternatively, any enantiomer of a compound of the general Formula I may be obtained by stereospecific synthesis using optically pure starting materials or reagents of known configuration.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Compounds of this invention are antagonists of the MCH receptor and as such are useful for the prevention and treatment of disorders or diseases associated with the MCH receptor. Accordingly, another aspect of the present invention provides a method for the treatment (including prevention, alleviation, amelioration or suppression) of diseases or disorders or symptoms mediated by MCH receptor binding and subsequent cell activation, which comprises administering to a mammal an effective amount of a compound of Formula I Such diseases, disorders, conditions or symptoms are, for example, obesity, diabetes, appetite and eating disorders, cardiovascular disease, hypertension, dyslipidemia, myocardial infarction, gall stones, osteoarthritis, certain cancers, AIDS wasting, cachexia, frailty (particularly in elderly), binge eating disorders including bulimina, anorexia, mental disorders including manic depression, depression, schizophrenia, mood disorders, delirium, dementia, severe mental retardation, anxiety, stress, cognitive disorders, sexual function, reproductive function, kidney function, diuresis, locomotor disorders, attention deficit disorder (ADD), substance abuse disorders and dyskinesias including Parkinson's disease, Parkinson-like syndromes, Tourette's syndrome, Huntington's disease, epilepsy, improving memory function, and spinal muscular atrophy.

The utilities of the present compounds in these diseases or disorders may be demonstrated in animal disease models that have been reported in the literature. The following are examples of such animal disease models: a) suppression of food intake and resultant weight loss in rats (Life Sciences 1998, 63, 113–117); b) reduction of sweet food intake in marmosets (Behavioural Pharm. 1998, 9, 179–181); c) reduction of sucrose and ethanol intake in mice (Psychopharm. 1997, 132, 104–106); d) increased motor activity and place conditioning in rats (Psychopharm. 1998, 135, 324–332; Psychopharmacol. 2000, 151: 25–30); e) spontaneous locomotor activity in mice (J. Pharm. Exp. Ther. 1996, 277, 586–594).

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per day, preferably from about 0.1 mg to about 10 mg per day. For oral administration, the compositions are preferably provided in the form of tablets containing from 0.01 to 1,000 mg, preferably 0.01, 0.05, 0.1, 0.5, 1.0, 2.5, 5.0, 10.0, 15.0, 20.0, 25.0, 30.0, 40.0, 50.0 or 1000.0 milligrams of the active ingredient for the symptomatic adjustment of the dosage to the patient to be treated.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. It will be appreciated that for the treatment or prevention of eating disorders, including obesity, bulimia nervosa and compulsive eating disorders, a compound of the present invention may be used in conjunction with other anorectic agents.

The present invention also provides a method for the treatment or prevention of eating disorders, which method comprises administration to a patient in need of such treatment an amount of a compound of the present invention and an amount of an anorectic agent, such that together they give effective relief.

Suitable anorectic agents of use in combination with a compound of the present invention include, but are not limited to, aminorex, amphechloral, amphetamine, benzphetamine, chlorphentermine, clobenzorex, cloforex, clominorex, clortemine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention also provides a method for the treatment or prevention of obesity, which method comprises administration to a patient in need of such treatment an amount of a compound of the present invention and an amount of an SSRI, such that together they give effective relief.

Suitable selective serotonin reuptake inhibitors of use in combination with a compound of the present invention include: fluoxetine, fluvoxamine, paroxetine and sertraline, and pharmaceutically acceptable salts thereof.

The present invention also provides a method for the treatment or prevention of obesity, which method comprises administration to a patient in need of such treatment an amount of a compound of the present invention and an amount of growth hormone secretagogues such as those disclosed and specifically described in U.S. Pat. No. 5,536,716; melanocortin agonists such as Melanotan II; β-3 agonists such as those disclosed and specifically described in patent publications WO94/18161, WO95/29159, WO97/46556, WO98/04526 and WO98/32753; 5HT-2 agonists; orexin antagonists; melanin concentrating hormone antagonists; galanin antagonists; CCK agonists; GLP-1 agonists; corticotropin-releasing hormone agonists; NPY-5 antagonists; CB1 modulators, such as N-(1-piperidinyl)-5-(4-chlorophenyl)-1-(2,4-dichlorophenyl)-4-methylpyrazole-3-carboxamide (SR141716A), and those described in U.S. Pat. No. 5,624,941 and U.S. Pat. No. 6,028,084, PCT Application Nos. WO98/43636, WO98/31227, WO98/41519, WO98/37061, WO00/10967, WO00/10968, WO97/29079, WO99/02499 and WO98/43635, and EPO Application No. EP-658546; and Y1 antagonists, such that together they give effective relief.

As used herein "obesity" refers to a condition whereby a mammal has a Body Mass Index (BMI), which is calculated as weight per height squared ($kg/m^2$), of at least 25.9. Conventionally, those persons with normal weight, have a BMI of 19.9 to less than 25.9.

It will be appreciated that for the treatment or prevention of obesity, the compounds of the present invention may also be used in combination with histamine receptor-3 (H3) modulators, CB1 cannabinoid receptor antagonists or inverse agonists, and/or phosphodiesterase-3B (PDE3B) inhibitors.

The obesity described herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

Excessive weight is a contributing factor to different diseases including hypertension, diabetes, dyslipidemias, cardiovascular disease, gall stones, osteoarthritis and certain forms of cancers. Bringing about a weight loss can be used, for example, to reduce the likelihood of such diseases and as part of a treatment for such diseases. Weight reduction can be achieved by antagonizing MCH-1R receptor activity to obtain, for example, one or more of the following effects: reducing appetite, increasing metabolic rate, reducing fat intake or reducing carbohydrate craving.

Other compounds that may be combined with a compound of Formula I, either administered separately or in the same pharmaceutical compositions, for the treatment of diabetes and other sequelae of excessive weight include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas, such as tolbutamide and glipizide;

(d) α-glucosidase inhibitors (such as acarbose), (e) cholesterol lowering agents such as (i) HMG-CoA reductase inhibitors (lovastatin, simvastatin, pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activator receptor a agonists such as fenofibric acid derivatives (gemfibrozil, clofibrate, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E, and (vii) thyromimetics;

(f) PPARδ agonists, such as those disclosed in WO97/28149;

(g) antiobesity compounds, such as fenfluramine, dexfenfluramine, phentermine, sibutramine, orlistat, or $β_3$ adrenergic receptor agonists;

(h) feeding behavior modifying agents, such as neuropeptide Y antagonists (e.g. neuropeptide Y5) such as those disclosed in WO 97/19682, WO 97/20820, WO 97/20821, WO 97/20822 and WO 97/20823;

(i) PPARα agonists such as described in WO 97/36579 by Glaxo;

(j) PPARγ antagonists as described in WO97/10813;

(k) serotonin reuptake inhibitors such as fluoxetine and sertraline;

(l) growth hormone secretagogues such as MK-0677.

It will be appreciated that for the treatment or prevention of stress, a compound of the present invention may be used in conjunction with other anti-stress agents, such as anti-anxiety agents. Suitable classes of anti-anxiety agents include benzodiazepines and $5\text{-HT}_{1A}$ agonists or antagonists, especially $5\text{-HT}_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable $5\text{-HT}_{1A}$ receptor agonists or antagonists include, in particular, the $5\text{-HT}_{1A}$ receptor partial agonists buspirone, flesinoxan, gepirone and ipsapirone, and pharmaceutically acceptable salts thereof.

Suitable CRF antagonists include the 4-tetrahydropyridylpyrimidine derivatives disclosed in U.S. Pat. No. 6,187,781; the aryloxy and arylthio-fused pyridine and pyrimidine derivatives disclosed in U.S. Pat. No. 6,124,300; the arylamino-fused pyrimidine derivatives disclosed in U.S. Pat. No. 6,107,300; the pyrazole and pyrazolopyrimidine derivatives disclosed in U.S. Pat. No. 5,705,646, U.S. Pat. No. 5,712,303, U.S. Pat. No. 5,968,944, U.S. Pat. No. 5,958,948, U.S. Pat. No. 6,103,900 and U.S. Pat. No. 6,005,109; the tetrahydropteridine derivatives disclosed in U.S. Pat. No. 6,083,948; the benzoperimidine carboxylic acid derivatives disclosed in U.S. Pat. No. 5,861,398; the substituted 4-phenylaminothiazol derivatives disclosed in U.S. Pat. No. 5,880,135; the cyclic CRF analogs disclosed in U.S. Pat. No. 5,493,006, U.S. Pat. No. 5,663,292 and U.S. Pat. No. 5,874,227; and the compounds disclosed in U.S. Pat. No. 5,063,245, U.S. Pat. No. 5,245,009, U.S. Pat. No. 5,510,458 and U.S. Pat. No. 5,109,111; as well as compounds described in International Patent Specification Nos. WO 94/13643, WO 94/13644, WO 94/13661, WO 94/13676 and WO 94/13677.

As used herein, the term "substance abuse disorders" includes substance dependence or abuse with or without physiological dependence. The substances associated with these disorders are: alcohol, amphetamines (or amphetamine-like substances), caffeine, cannabis, cocaine, hallucinogens, inhalants, nicotine, opioids, phencyclidine (or phencyclidine-like compounds), sedative-hypnotics or benzodiazepines, and other (or unknown) substances and combinations of all of the above.

In particular, the term "substance abuse disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation.

Other "substance abuse disorders" include substance-induced anxiety disorder with onset during withdrawal; substance-induced mood disorder with onset during withdrawal; and substance-induced sleep disorder with onset during withdrawal.

Similarly, compound of Formula I, will be useful as a partial or complete substitute for conventional pain relievers in preparations wherein they are presently co-administered with other agents or ingredients. Thus in further aspects, the invention encompasses pharmaceutical compositions for modulating the perception of pain comprising a non-toxic therapeutically effective amount of the compound of Formula I as defined above and one or more ingredients such as another pain reliever including acetaminophen or phenacetin, or a cyclooxygenase-2 (COX-2) inhibitor; a potentiator including caffeine; a prostaglandin including misoprostol, enprostil, rioprostil, ornoprostol or rosaprostol: a diuretic; a sedating or non-sedating antihistamine. Examples of cyclooxygenase-2 selective inhibitors include rofecoxib (VIOXX®, see U.S. Pat. No. 5,474,995), etoricoxib (ARCOXIA™ see U.S. Pat. No. 5,861,419), celecoxib (CELEBREX®, see U.S. Pat. No. 5,466,823), valdecoxib (see U.S. Pat. No. 6,633,272), parecoxib (see U.S. Pat. No. 5,932,598), COX-189 (Novartis), BMS347070 (Bristol Myers Squibb), tiracoxib (JTE522, Japan Tobacco), ABT963 (Abbott), CS502 (Sankyo) and GW406381 (GlaxoSmithKline). Other examples of cyclooxygenase-2 inhibitors compounds are disclosed in U.S. Pat. No. 6,020,343. In addition the invention encompasses a method of treating pain comprising: administration to a patient in need of such treatment a non-toxic therapeutically effective amount of the compound of Formula I, optionally co-administered with one or more of such ingredients as listed immediately above.

Suitable antipsychotic agents of use in combination with a compound of the present invention for the treatment of schizophrenia include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindone. Other antipsychotic agents include loxapine, sulpiride and risperidone. It will be appreciated that the antipsychotic agents when used in combination with a CB1 receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with a compound of the present invention include dopamine receptor antagonists, especially D2, D3 and D4 dopamine receptor antagonists, and muscarinic M1 receptor agonists. An example of a D3 dopamine receptor antagonist is the compound PNU-99194A. An example of a D4 dopamine receptor antagonist is PNU-101387. An example of a muscarinic M1 receptor agonist is xanomeline.

Another class of antipsychotic agent of use in combination with a CB1 receptor modulator is the $5\text{-HT}_{2A}$ receptor antagonists, examples of which include MDL100907 and fananserin. Also of use in combination with a compound of the present invention are the serotonin dopamine antagonists (SDAs) which are believed to combine $5\text{-HT}_{2A}$ and dopamine receptor antagonist activity, examples of which include olanzapine and ziperasidone.

It will be appreciated that for the treatment of depression or anxiety, a compound of the present invention may be used in conjunction with other anti-depressant or anti-anxiety agents.

Suitable classes of anti-depressant agents include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists neurokinin-1 antagonists and atypical anti-depressants.

Suitable norepinephrine reuptake inhibitors include tertiary amine tricyclics and secondary amine tricyclics. Suitable examples of tertiary amine tricyclics include: amitriptyline, clornipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include those described supra.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those described hereinabove

Suitable atypical anti-depressants include: bupropion, lithium, nefazodone, trazodone and viloxazine, and pharmaceutically acceptable salts thereof.

The neurokinin-1 receptor antagonist may be peptidal or non-peptidal in nature, however, the use of a non-peptidal neurokinin-1 receptor antagonist is preferred. In a preferred embodiment, the neurokinin-1 receptor antagonist is a CNS-penetrant neurokinin-1 receptor antagonist. In addition, for convenience the use of an orally active neurokinin-1 receptor antagonist is preferred. To facilitate dosing, it is also preferred that the neurokinin-1 receptor antagonist is a long acting neurokinin-1 receptor antagonist. An especially preferred class of neurokinin-1 receptor antagonists of use in the present invention are those compounds which are orally active and long acting.

Neurokinin-1 receptor antagonists of use in the present invention are fully described, for example, in U.S. Pat. Nos. 5,162,339, 5,232,929, 5,242,930, 5,373,003, 5,387,595, 5,459,270, 5,494,926, 5,496,833, 5,637,699; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; and in British Patent Publication Nos. 2 266 529, 2 268 931, 2 269 170, 2 269 590, 2 271 774, 2 292 144, 2 293 168, 2 293 169, and 2 302 689.

Specific neurokinin-1 receptor antagonists of use in the present invention include:

(±)-(2R3R,2S3S)-N-{[2-cyclopropoxy-5-(trifluoromethoxy)-phenyl]methyl}-2-phenylpiperidin-3-amine;

2-(S)-(3,5-bis(trifluoromethyl)benzyloxy)-3(S)-(4-fluorophenyl)-4-(3-(5-oxo-1H,4H-1,2,4-triazolo)methyl)morpholine;

2-(R)-(1-(R)-(3,5-bis(trifluoromethyl)phenyl)ethoxy)-4-(3-(5-oxo-1H,4H-1,2,4-triazolo)methyl)-3-(S)-phenyl-morpholine;

2-(S)-(3,5-bis(trifluoromethyl)benzyloxy)-4-(3-(5-oxo-1H,4H-1,2,4-triazolo)methyl)-3-(S)-phenyl-morpholine;

2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine;

2-(R)-(1-(R)-(3,5-bis(trifluoromethyl)phenyl)ethoxy)-4-(5-(N,N-dimethylamino)methyl-1,2,3-triazol-4-yl)methyl-3-(S)-phenylmorpholine;

2-(R)-(1-(R)-(3,5-bis(trifluoromethyl)phenyl)ethoxy)-4-(5-(N,N-dimethylamino)methyl-1,2,3-triazol-4-yl)methyl-3-(S)-(4-fluorophenyl)morpholine;

(3S,5R,6S)-3-[2-cyclopropoxy-5-(trifluoromethoxy)phenyl]-6-phenyl-1-oxa-7-aza-spiro[4.5]decane;

(3R,5R,6S)-3-[2-cyclopropoxy-5-(trifluoromethoxy)phenyl]-6-phenyl-1-oxa-7-aza-spiro[4.5]decane;

2-(R)-(1-(S)-(3,5-bis(trifluoromethyl)phenyl)-2-hydroxyethoxy)-3-(S)-(4-fluorophenyl)-4-(1,2,4-triazol-3-yl)methylmorpholine;

2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine;

2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;

2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine;

or a pharmaceutically acceptable salt thereof.

Suitable classes of anti-anxiety agents include benzodiazepines and 5-HT$_{1A}$ agonists or antagonists, especially 5-HT$_{1A}$ partial agonists, and corticotropin releasing factor (CRF) antagonists.

Suitable benzodiazepines include those previously described herein.

Suitable receptor agonists or antagonists include, in particular, those described supra.

For the treatment of autism, the compounds of the present invention may be used in combination with butyrophenones.

For the treatment of Parkinson's disease and Parkinson-like syndromes, the compounds of the present invention may be used in combination with levodopa, carbidopa/levodopa, amantadine, bromocriptine and other ergot alkaloids, anticholinergic medications such as benztropine, trihexyphenidyl, antihistamines such as diphenhydramine and orphenadrine, mild sedatives, tricyclic antidepressants such as amitriptiline and others described supra, and propanolol.

For the treatment of Huntingdon's Chorea, the compounds of the present invention may be used in combination with phenothiazine, chlorpromazine, and butyrophenone neuroleptics such as haloperidol or reserpine.

For the treatment of epilepsy, the compounds of the present invention may be used together with anticonvulsants such as penytoin, phenobarbital, primidone, carbamazepine, trimethadione, clonazepam, valproate and ethosuximide In one embodiment of a combination for the treatment of male or female sexual dysfunction, the second ingredient to be combined with a compound of Formula I can be a type V cyclic-GMP-specific phosphodiesterase (PDE-V) inhibitor, such as sildenafil and IC-351 or a pharmaceutically acceptable salt thereof; an alpha-adrenergic receptor antagonist, such as phentolamine and yohimbine or a pharmaceutically acceptable salt thereof; or a dopamine receptor agonist, such as apomorphine or a pharmaceutically acceptable salt thereof. "Male sexual dysfunction" includes impotence, loss of libido, and erectile dysfunction. "Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders. "Female sexual dysfunction" can be seen as resulting from multiple components including dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an MC-4 receptor agonist can result in improved blood flow, improved lubrication, improved sensation, facilitation of reaching orgasm, reduction in the refractory period between orgasms, and improvements in arousal and desire. In a broader sense, "female sexual dysfunction" also incorporates sexual pain, premature labor, and dysmenorrhea.

For the treatment of male and female sexual dysfunction, the compounds of the present invention may be employed in combination with a compound selected from a type V cyclic-GMP-specific phosphodiesterase (PDE-V) inhibitor, such as sildenafil and IC-351 or a pharmaceutically acceptable salt thereof; an alpha-adrenergic receptor antagonist, such as phentolamine and yohimbine or a pharmaceutically acceptable salt thereof; or a dopamine receptor agonist, such as apomorphine or a pharmaceutically acceptable salt thereof.

MCH-1R antagonist compounds can be provided in kit. Such a kit typically contains an active compound in dosage forms for administration. A dosage form contains a sufficient amount of active compound such that a beneficial effect can be obtained when administered to a patient during regular intervals, such as 1 to 6 times a day, during the course of 1 or more days. Preferably, a kit contains instructions indicating the use of the dosage form for weight reduction (e.g., to treat obesity or overweight) or stress reduction, and the amount of dosage form to be taken over a specified time period.

The method of treatment of this invention comprises a method of treating melanin concentrating hormone receptor mediated diseases by administering to a patient in need of such treatment a non-toxic therapeutically effective amount of a compound of this invention that selectively antagonizes the MCH receptor in preference to the other G-protein coupled receptors. In particular, the present invention comprises a method of treating MCR-1R receptor subtype mediated diseases by administering to a patient in need of such treatment a non-toxic therapeutically effective amount of a compound of this invention that selectively antagonizes the MCH-1R receptor.

The weight ratio of the compound of the Formula I to the second active ingredient may be varied and will depend upon the effective dose of each ingredient. Generally, an effective dose of each will be used. Thus, for example, when a compound of the Formula I is combined with a β-3 agonist the weight ratio of the compound of the Formula I to the β-3 agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The compounds of Formula I of the present invention can be prepared according to the procedures of the following Schemes and Examples, using appropriate materials and are further exemplified by the following specific examples. Moreover, by utilizing the procedures described with the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously herein above. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray.

The phrase "standard peptide coupling reaction conditions" means coupling a carboxylic acid with an amine using an acid activating agent such as 1-(3-dimethylaminopropyl)-3-ethylcarbodiimide HCl (EDC), 1,3-dicyclohexylcarbodiimide (DCC), and benzotriazol-1-yloxytris(dimethylamino) phosphonium hexafluorophosphate (BOP) in an inert solvent such as dichloromethane in the presence of a catalyst such as 4-dimethylaminopyridine (DMAP) or 1-hydroxybenzotriazole hydrate (HOBT). The use of protecting groups for the amine, carboxylic acid or other functionalities to facilitate the desired reaction and minimize undesired reactions is well documented. Conditions required to remove protecting groups are found in standard textbooks such as Greene, T. and Wuts, P. G. M., *Protective Groups in Organic Synthesis*, John Wiley & Sons, Inc., New York, N.Y., 1991. Benzyloxycarbonyl (CBZ) and t-butyloxycarbonyl (BOC) protecting groups are commonly used protecting groups in organic synthesis, and conditions for their removal are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of trifluoroacetic acid (TFA) and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

| Abbreviations Used in the Description of the Preparation of the Compounds of the Present Invention and Biological Assays: | |
|---|---|
| BOC (boc) | t-butyloxycarbonyl |
| BOP | benzotriazol-1-yloxytris(dimethylamino)phosphonium hexafluorophosphate |
| BSA | Bovine serum albumin |
| Bu | butyl |
| calc. | calculated |
| CBZ (Cbz) | benzyloxycarbonyl |
| DCC | 1,3-dicyclohexylcarbodiimide |
| DIEA | diisopropylethylamine |
| DMAP | 4-dimethylaminopyridine |
| DMF | N,N-dimethylformamide |
| ECB buffer | Extra cellular buffer: 140 nM NaCl, 20 nM KCl, 20 mM HEPES-NaOH pH 7.4, 5 mM glucose, 1 mM MgCl$_2$, 1 mM CaCl$_2$, 0.1 mg/mL BSA |
| EDC | 1-(3-dimethylaminopropyl)-3-ethylcarbodiimide HCl |
| EDTA | Ethylenediaminetetraacetic acid |
| eq. | equivalent(s) |
| ES-MS | electron spray ion-mass spectroscopy |
| Et | ethyl |
| EtOAc | ethyl acetate |
| HEPES | 4-(2-hydroxyethyl)piperazine-1-ethane sulfonic acid |
| HOAc | acetic acid |
| HOBt | 1-hydroxybenzotriazole hydrate |
| HPLC | high performance liquid chromatography |
| h | hour |
| Me | methyl |
| MF | molecular formula |
| MS | mass spectrum |
| Ms | methanesulfonyl |
| POCl$_3$ | phosphorous oxychloride |
| Ph | phenyl |
| Pr | propyl |
| prep. | preparative |
| r.t. | room temperature |
| TEA | triethylamine |
| TFA | trifluoroacetic acid |
| THF | tetrahydrofuran |
| TLC | thin-layer chromatography. |

General Preparation of
N-2-(aminoquinolin-6-yl)carboxamide Compounds
8

Scheme A

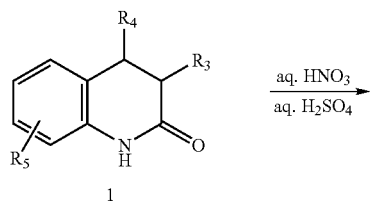

1

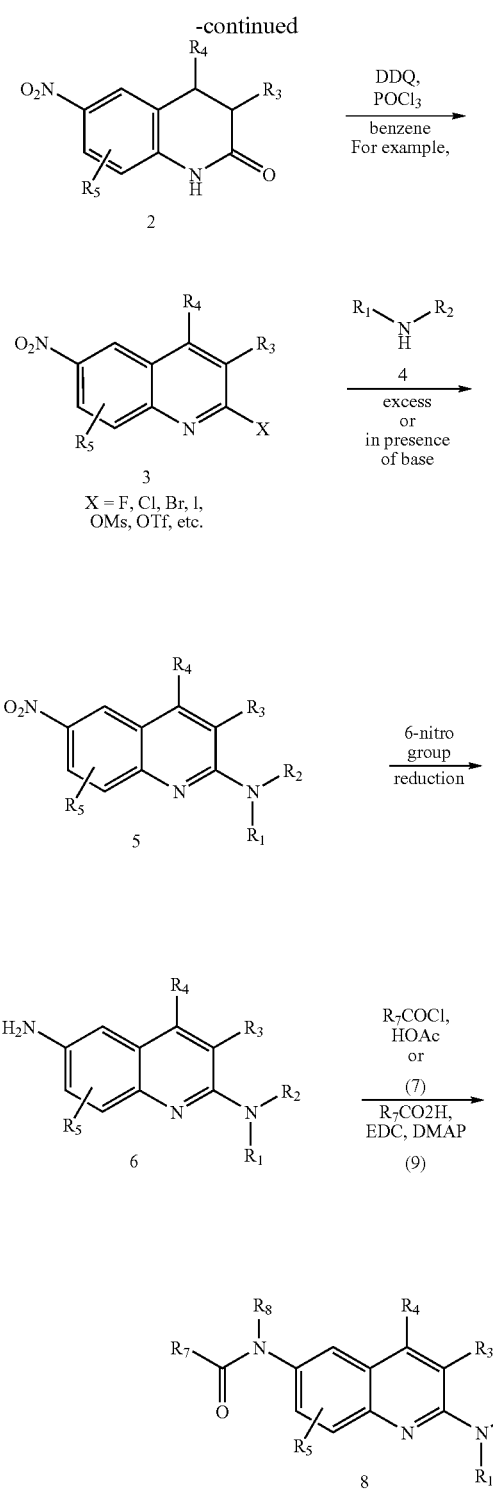

X = F, Cl, Br, I, OMs, OTf, etc.

There are many known preparation of quinolines available to those skilled in the art. Scheme A illustrates the preparation of substituted quinolines utilized for the present invention and follows closely to published procedures reported by Lee et al. *Heterocycles* 1998, 48 (12), pp 2637–2641. Treatment of substituted 3,4-dihydroquinolin-2(1H)-ones 1, with aq. nitric acid in aq. sulfuric acid provides the 6-nitro-3,4-dihydroquinolin-2(1H)-one intermediates 2.

These intermediates 2 may be converted to the substituted quinoline intermediates 3, which possess a leaving group such as halogen, mesylate or triflate at the 2-position by a variety of methods known to those skilled in the art. For example, treatment of 3,4-dihydroquinolin-2(1H)-ones 2 with phosphorous oxychloride and 2,3-dichloro-5,6-dicyano-1,4-benzoquinone in refluxing benzene provides the intermediate 3 with X=Cl. Heating intermediates 3 with a variety of amine intermediates 4, neat or with excess amine in an alcoholic solvent provides the 2-amino-6-nitroquinoline intermediates 5. Alternatively, the 2-substituted-6-nitroquinoline intermediates 3 may be reacted with an amine or amine salt 4 in the presence of excess amine, a tertiary amine base or inorganic base such as sodium bicarbonate to provide the intermediates 5. If the amine reagent 4 is volatile the reaction may be performed in a sealed tube or other apparatus known to those skilled in the art. The 6-nitroquinoline intermediates 5 may be reduced to the substituted quinoline-2,6-diamine intermediates 6 using a variety of methods known to those skilled in the art. For example, the reduction may be achieved by catalytic hydrogenation in the presence of a noble metal or its oxide such as palladium on activated carbon in a protic solvent such as methanol or ethanol. Alternatively, the nitro group may be reduced by a variety of chemical methods known to those skilled in the art such as, catalytic iron (IEI) chloride hexahydrate with carbon and hydrazine system or tin (II) chloride-hydrate in an alcoholic solvent. Reaction of the quinoline-2,6-diamine intermediates 6 with a variety of carboxylic acid chloride intermediates 7 in acetic acid solvent or in an inert solvent such as methylene chloride in the presence of a tertiary amine base provides the desired compounds 8 of the present invention. Alternatively, the carboxamide compounds 8 may be produced by reaction of 2,6-quinolin-2,6-diamine intermediates 6 and a variety of carboxylic acid intermediates 9 using standard peptide coupling conditions such as 1-(3-dimethylaminopropyl)3-ethylcarbodiimide HCl (EDC) and 4-dimethylaminopyridine (DMAP) in an inert solvent such as methylene chloride.

Treatment of carboxylic acid intermediates 9 with oxalyl chloride with a catalytic amount of N,N-dimethylformamide (DMF) in an inert solvent such as methylene chloride under an inert atmosphere provides the corresponding acid chloride intermediates 7 (Scheme B). Similarly, treatment of the carboxylic acid intermediates 9 with thionyl chloride in toluene at reflux provides acid chloride intermediates 7. Carboxylic acid intermediates 9 are available from a wide range of commercial sources. Alternatively, carboxylic acid derivatives 9 may be prepared by a variety of methods known to those skilled in the art such as, but not limited to, oxidation of other functional groups, carbonylation reactions, saponification of ester intermediates, or deprotection of protected carboxylic acids. Homologated carboxylic acids may be prepared from carboxylic acids 9 by conversion to the corresponding carboxaldehyde intermediates (or directly from available carboxaldehydes) followed by homologation utilizing stabilized Wittig or Horner-Emmons reagents to provide unsaturated acid or ester intermediates. These intermediates may be converted directly to carboxylic acid derivatives 9. Alternatively, the resulting olefin may be functionalized or reduced to the saturated derivative by a variety of conditions known to those skilled in the art such as by catalytic hydrogenation in the presence of a noble metal catalyst such as palladium on carbon or platinum oxide. These saturated intermediates may in turn be converted to carboxylic acid derivatives 9.

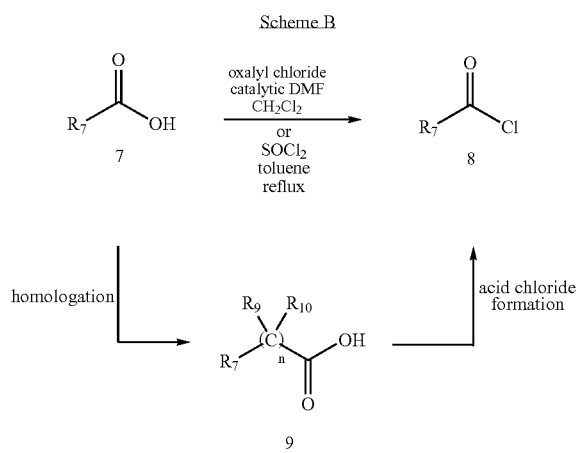

Amine intermediates 4 are available from commercial sources or alternatively may be prepared from a variety of intermediates known to those skilled in the art. For example, amines may be prepared by those skilled in the art by reduction of other functional groups such as carboxamides, lactams, nitriles and nitro-containing compounds. Alternatively, amines may be prepared from compounds containing leaving groups by reaction with amines, amine surrogates such as azides or carbamates followed by reduction or deprotection. Furthermore, primary amines may be reacted with carboxaldehydes or carboxylic acids or derivatives thereof followed by reduction with a variety of reagents such as sodium cyanoborohydride, sodium borohydride, lithium aluminium hydride or borane reagents to produce amine intermediates 4. Many other methods to produce amine intermediates are know in the literature and may be utilized by those skilled in the art for their preparation.

General Preparation of
N,N'-(2-aminoquinolin-6-yl)urea Compounds 11

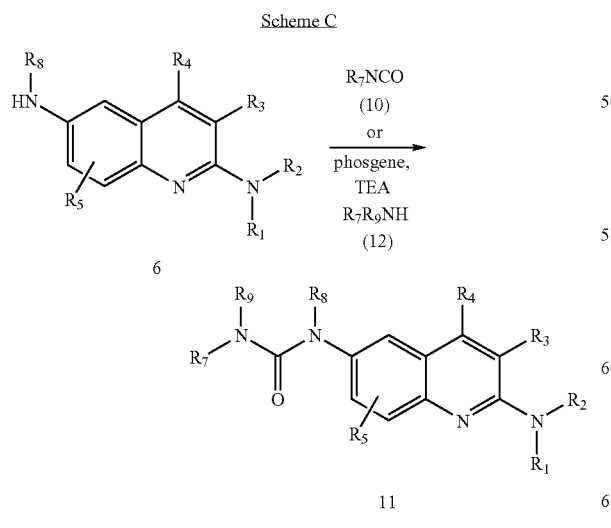

Treatment of quinolin-2,6-diamine intermediates 6 with isocyanate intermediates 10 in an inert solvent provides the substituted N,N'-(2-aminoquinolin-6-yl)urea compounds 11. Alternatively, treatment of an amine intermediate 12 with phosgene or equivalent reagent in the presence of a tertiary amine base such as triethylamine provides isocyanate or carbamoyl chloride intermediates which in turn may be reacted with intermediates 6 to provide N,N'-(2-aminoquinolin-6-yl)urea compounds 11. Similarly, treatment of quinolin-2,6-diamine intermediates 6 with phosgene or equivalent reagent in the presence of a tertiary amine base such triethylamine provides isocyanate or carbamoyl chloride intermediates, which in turn may be reacted with amine intermediates 12 to provide N,N'-(2-aminoquinolin-6-yl) urea compounds 11.

General Preparation of
2-aminoquinolin-6-carboxamide and Related Derivatives

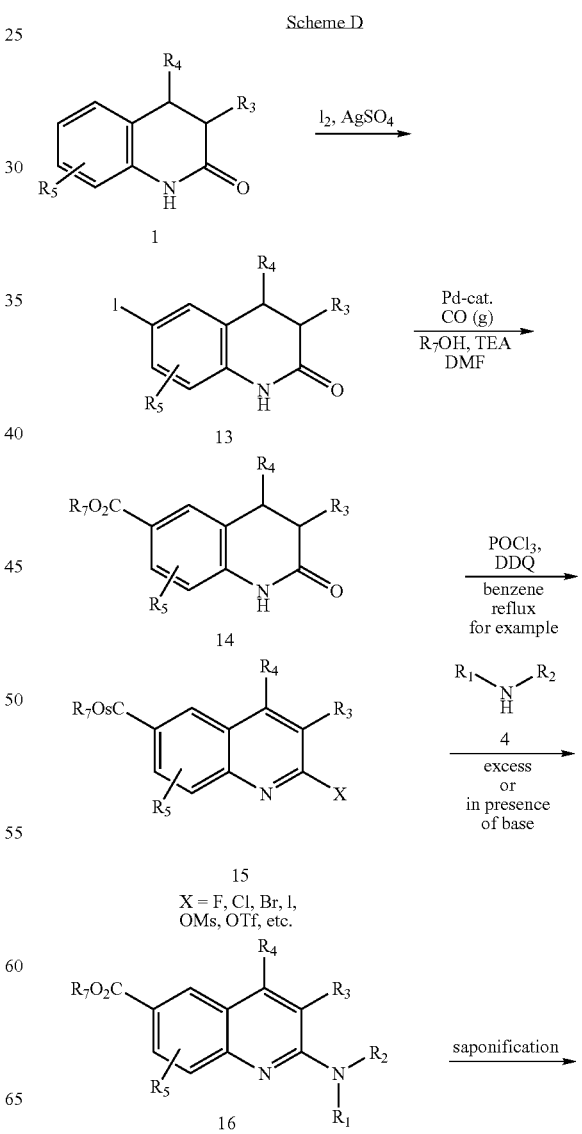

39

-continued

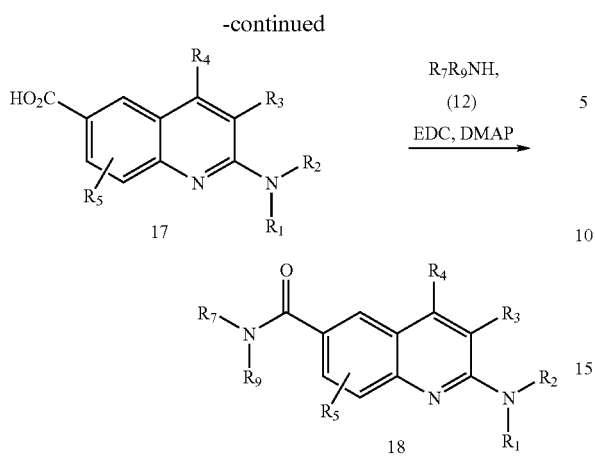

Compounds of the present invention containing carboxamides at the quinoline 6-position may be prepared as outlined in Scheme D. Reaction of 3,4-dihydroquinolinone intermediates 1 with iodine and silver sulfate affords the 6-iodo intermediates 13. Carbonylation of the iodide under a variety of procedures known to those skilled in the art, such as use of a Pd-catalyst in the presence of carbon monoxide (CO) and an alcohol, provides the 2-oxo-1,2,3,4-tetrahydroquinoline-6-carboxylate ester intermediates 14. 2-Chloroquinoline formation using procedures described above in Scheme A affords the 2-chloroquinoline-6-carboxylate ester intermediates 15 (X=Cl). Displacement reactions of the 2-chloro group with amine intermediates 4 under conditions described in Scheme A provides the 2-aminoquinoline-6-carboxylate intermediates 16. Hydrolysis or saponification of the carboxylate intermediates 16 under acidic or basic conditions produces the carboxylic acid intermediates 17. Similarly, removal of other carboxylate protecting group not removed by hydrolysis or for intermediates containing other functional groups incompatible with the above mentioned hydrolysis conditions may be achieved using conditions known to those skilled in the art. For example, tert-butyl esters may be cleaved by treatment with trifluoroacetic acid. Alternatively, benzyl esters may be cleaved by catalytic hydrogenation over a noble metal catalysts such as palladium on activated carbon. Treatment of the resulting carboxylic acid intermediates 17 with amine intermediates 12 under standard peptide coupling conditions such as EDC and DMAP in an inert solvent such as methylene chloride provides the desired quinoline-6-carboxamides 18.

40

General Preparation of Homologated
2-aminoquinolin-6-carboxamide and Related
Derivatives Scheme E

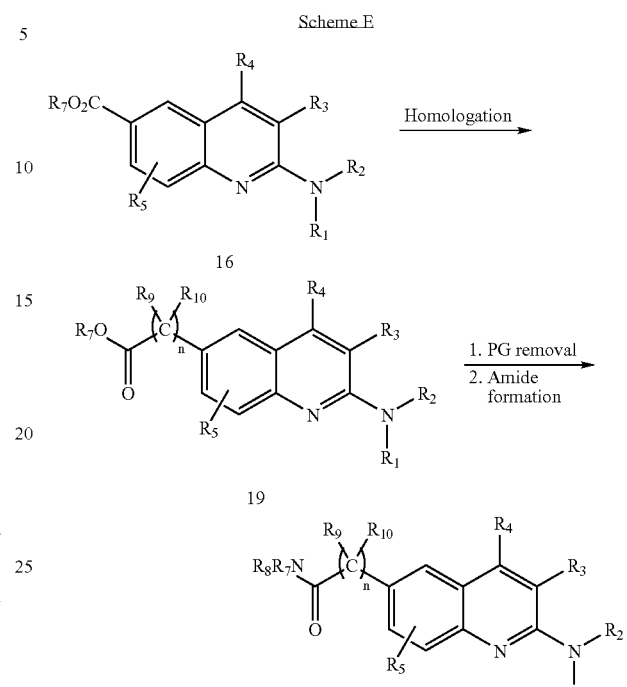

Homologated carboxamide analogs may be prepared by homologation of the carboxylic acid intermediates 16 or other intermediates derived thereof using method known to those skilled in the art such as, but not limited to, the Arndt-Eistert homologation, or by the sequence of conversion of the acid to the alcohol, leaving group formation, cyanide displacement followed by hydrolysis to the homologated carboxylic acid intermediates 19. Similarly, the carboxylic acid intermediates 16 may be converted to the carboxaldehyde intermediate followed by Wittig or Homer-Emmons homologation and subsequent functional group manipulation as described earlier. These homologated carboxylic acid intermediates 19 may be converted by standard peptide coupling techniques such as those described in Scheme D, with a variety of amines to homologated carboxamide derivatives 20. Alternatively, the homologated carboxylic acid intermediates 19 may be prepared from 3,4-dihydro-quinolin-2-one intermediates that possess a homologated carboxylic acid functional group using the reaction sequence outlined in Scheme A.

General Preparation of 4-amino-6-heterocycle
Substituted Quinoline Derivatives and Related
Analogs Scheme F eq. 1

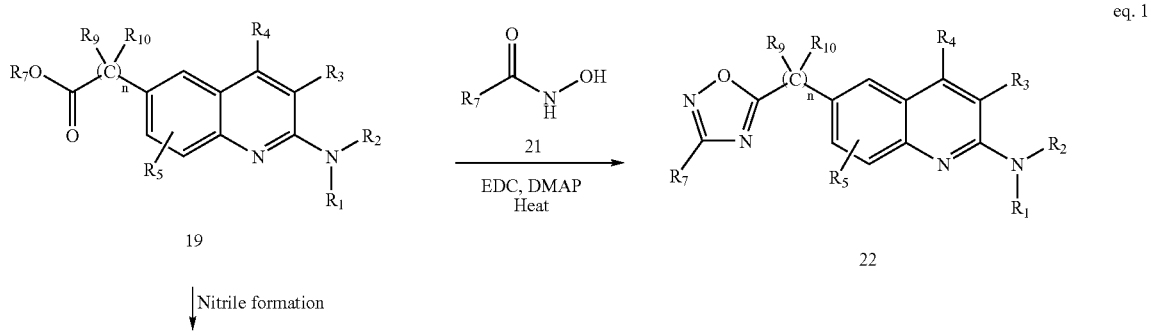

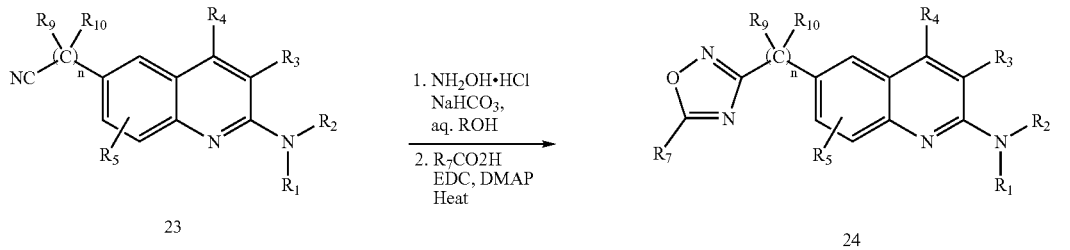

Quinoline derivatives containing heterocycle groups at the 6-position in place a 6-carboxamide or related analogs may be prepared as outlined in Scheme F from 2-aminoquinoline-6-carboxylic acid derivatives 19 or related homologs 1,2,4-Oxadiazolyl or related heterocyclic derivatives are known to be useful replacements for carboxamide, urea, sulfonamide and other hydrogen bond donating functional groups. Removal of these hydrogen bonding groups may change water solubility, remove waters of hydration or vary other physical chemical properties that may improve pharmacokinetic parameters such as oral absorption, oral bioavailability or metabolic disposition of these compounds.

These heterocycle substituted quinoline derivatives may be prepared by a variety of methods known to those skilled in the art. For example, treatment of quinolin-6-carboxylic acid intermediates 19 with EDC and DMAP in the presence of an amidoxime derivative 21 followed by heating at reflux in an inert solvent such 1,4-dioxane or 1,2-dimethoxyethane provides 6-(3-substituted-1,2,4-oxadiazol-yl)quinolin-2-amine derivatives 22. Similarly, homologated (2-aminoquinolin-6-yl)carboxylic acid intermediates 19 provide the related homologated 6-(3-substituted-1,2,4-oxadiazol-5-yl-quinolin-2-amine analogs 22. Amidoxime intermediates 21 may be commercially available or may be prepared from nitrile intermediates by treatment with hydroxylamine hydrochloride in the presence of an inorganic base such as sodium bicarbonate in an alcoholic solvent.

Isomeric (5-substituted-1,2,4-oxadiazol-3yl)quinolin-2-amines 24 may be prepared in a similar fashion from 2-aminoquinoline-6-nitrile intermediates 23 or related homologs. 2-Aminoquinoline-6-nitrile intermediates 23 may be prepared as outlined in Scheme A directly from nitrile substituted 3,4-dihydroquinolin-2-one intermediates. Alternatively, quinoline-6-carboxylic acid derivatives 19 may be converted to quinoline-6-carboxamide derivatives as described earlier followed by dehydration using a variety of methods known to those skilled in the art. Reaction of the nitrile intermediates 23 with hydroxylamine as described above affords the corresponding amidoxime intermediates. Coupling of the amidoxime intermediates with a carboxylic acid derivatives 7 in the presence of EDC and DMAP followed by heating in an inert solvent provides the isomeric 6-(5-substituted-1,2,4-oxadiazol-3-yl)quinolin-2-amine analogs 24. Similarly, homologated 2-aminoquinolin-6-yl)carboxylic acid intermediates 19 may be converted to homologated nitrile intermediates 23 then, by analogy, to related 6-(5-substituted-1,2,4-oxadiazol-3-yl)quinolin-4-amine homologs 24.

Preparation of 6-substituted quinolin-2.6-diamine Derivatives

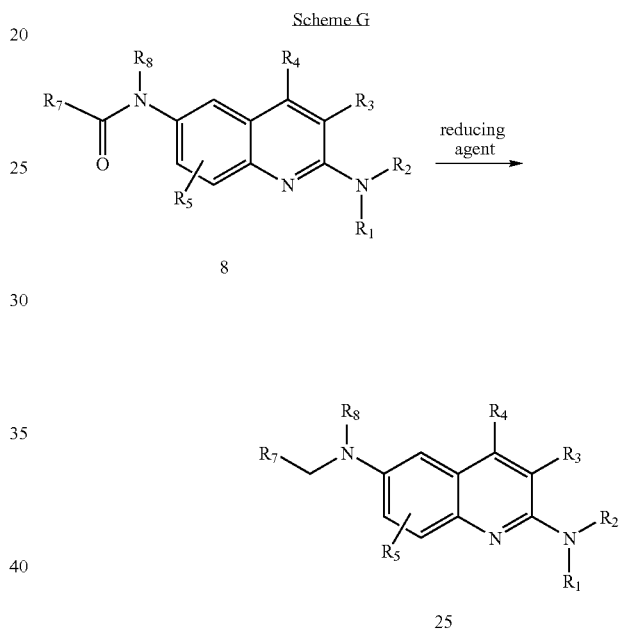

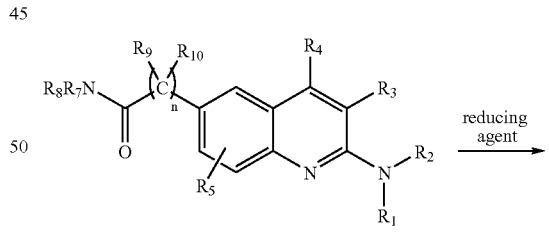

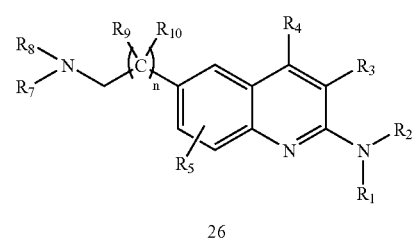

-continued eq. 3

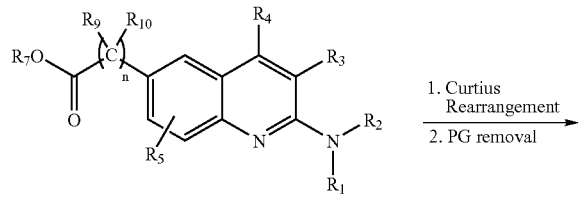

19

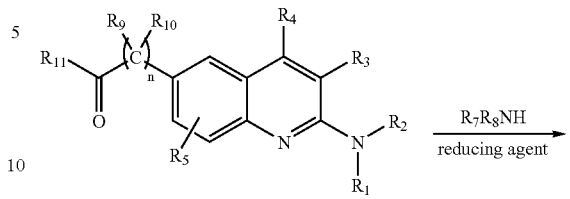

30

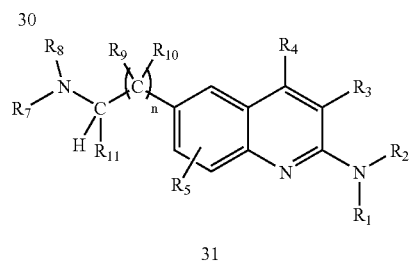

31

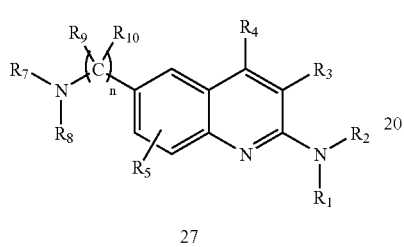

27

Preparation of further 6-substituted-quinolin-2,6-diamine derivatives is outlined in Scheme G. Simple chemical reduction of the carboxamide group of N-(2-aminoquinolin-6-yl) carboxamide intermediates 8 (eq. 1) by a variety of reducing agents known to those skilled in the art, such as borane derivatives or lithium aluminium hydride, affords the 6-substituted-quinolin-2,6-diamine derivatives 25 respectively. Alternatively, carboxylic acid intermediates 19 may be converted to amine derivatives 25 by rearrangement reactions such as the Curtius reaction or related rearrangement reactions known to those skilled in the art. Hydrolysis of amine intermediates or removal of protecting groups resulting from the rearrangement reaction products may provide the desired diaminoquinoline derivatives 27.

Similarly, quinoline diamine derivatives 28 may be converted to other quinoline-diamine derivatives 29 by reductive amination with a carboxaldehyde or ketone derivative (Scheme H, eq. 1) or by first, carboxamide formation, followed by reduction of the carboxamide intermediate to the quinoline diamine derivatives 29. Alternatively, (2-aminoquinolin-6-yl) derived carboxaldehyde intermediates 30 ($R_{11}$=H, eq. 2) or related ketone intermediates 30 ($R_{11}$=alkyl, aryl, cycloalkyl, eq. 2) may be converted to quinoline diamine derivatives 31 by reductive amination with a variety of amines under a variety of conditions known to those skilled in the art such as sodium cyanoborohydride in the presence of a drying agent and acid buffer in an appropriate solvent such as methanol. (2-Aminoquinoline 6-carboxaldehyde intermediates 30 or related homologated intermediates may be prepared by a variety of methods known to those skilled in the art. For example, oxidation of related alcohol derivatives or reduction of carboxylic acid or related carboxamide, ester or nitrile derivatives may provide the desired (2-aminoquinoline-6-carboxaldehyde intermediates 30 or related homologs. Similarly, (2-aminoquinolin-6-yl)ketone intermediates 30 or related homologs may be prepared from above intermediates by many methods known to those skilled in the art. Alternatively, quinoline carboxaldehyde or ketone intermediates 30 may be reduced to the corresponding alcohol intermediates, subsequent leaving group formation then displacement with a suitable amine or surrogate amine nucleophile. Further functional group manipulation or protecting group removal may provide quinoline diamine derivatives 31.

Scheme H eq. 1

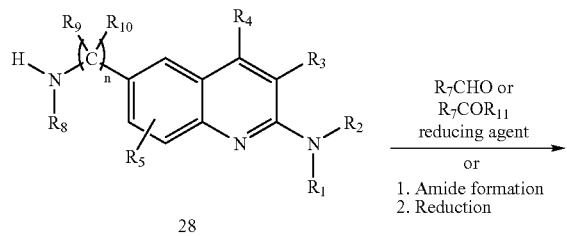

28

Scheme I eq. 1

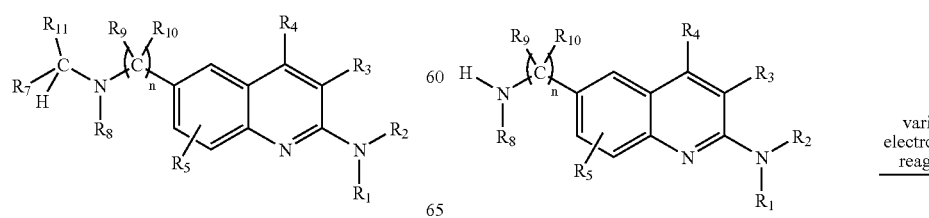

29  32

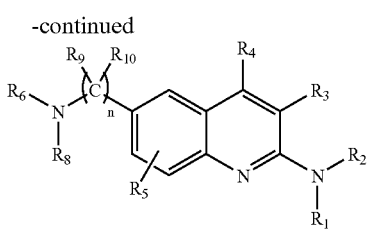

33

Further derivatives of quinoline di amine intermediates 32 may be prepared by reaction of the amine with a variety of electrophiles such as carboxylic acids or their acid chlorides, isocyanates, carbamoyl chlorides, ketenes, chloroformates, sulfonic acids or their sulfonyl chloride to provide further derivatives of the present invention of the general structure 33 (Scheme I).

The following Examples are provided to illustrate the invention and are not to be construed as limiting the scope of the invention in any manner.

EXAMPLE 1

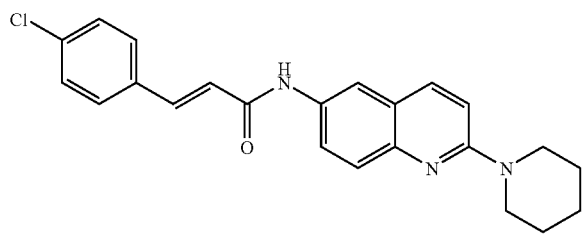

(2E)-3-(4-chlorophenyl)-N-[2-(piperidin-1-yl)quinolin-6-yl]-prop-2-enamide hydrochloride Step A: Preparation of 6-nitro-3,4-dihydroqiuinolin-2(1H)-one In a 500 mL round bottom flask equipped with a stir bar was placed 3,4-dihydroquinolin-2(1H)-one (5 g, 34 mol). To the solid was added with stirring, concentrated sulfuric acid (100 mL). After complete dissolution of the solids, the reaction mixture was cooled in an ice/methanol bath. To the resulting solution was added water (25 mL) followed by dropwise addition by addition funnel of 61% aq. nitric acid (4.6 mL, 34 mmol; 2.1 mL 70% nitric acid diluted with 2.5 mL water). The resulting deep red reaction mixture was stirred for 0.25 h with cooling in the ice/methanol bath. The reaction mixture was carefully poured onto ice (250 g) with stirring and external cooling. After the ice melted, the resulting solids were filtered, washed with excess water (2×25 mL) followed by ether (2×25 mL). Resulting solids were air dried to provide the product as an off-white solid, MS: m/z 193 (MH$^+$), which was used without further purification in the subsequent reaction.

Step B: Preparation of 2-chloro-6-nitroquinoline

To a mixture of the crude product (3.0 g, 15.6 mmol) from Step A, and 2,3-dichloro-5,6-dicyano-1,4-benzoquinone (3.5 g, 15.6 mmol) in 50 mL benzene was added dropwise by addition funnel to phosphorous oxychloride (7.1 mL, 78 mmol). The resulting reaction mixture was heated at reflux for 5 h at which time it was cooled in an ice bath. To the cooled mixture was carefully added water (50 mL). The resulting mixture was neutralized with 5N aq. sodium hydroxide (~60 mL) then filtered. The filtrate was extracted with ether (3×200 mL). The ether extracts were combined, dried over sodium sulfate, filtered and the solvent removed under vacuum to afford the product, MS: m/z 208 (MH$^+$), which was used directly in the next step.

Step C: Preparation of 6-nitro-2-piperidin-1-ylquinoline

The product (208 mg, 1.0 mmol) from Step B and piperidine (0.5 mL, 5 mmol) were mixed in absolute ethanol (3 mL) and then heated at reflux for 4 h. The reaction mixture was cooled to r.t., and the solvent removed under vacuum. The solids were taken up in EtOAc (125 mL). The mixture was transferred to a separatory funnel and washed with water (3×15 mL). The organic layer was dried over sodium sulfate, filtered and the solvent removed under vacuum to afford the product as a yellow solid, MS: m/z 258 (MH$^+$) which was used without further purification.

Step D: Preparation of 2-piperidin-1-ylquinolin-6-amine

The product (204 mg, 0.8 mmol) of Step C and palladium hydroxide on carbon (100 mg) was suspended in methanol. The resulting mixture was degassed then stirred under hydrogen atmosphere (balloon) until all the yellow solids had dissolved. The reaction mixture was filtered through filter aid and the solvent removed under vacuum to afford the product as a brown solid, MS: m/z 228 (MH$^+$), which was used without further purification Step E: Preparation of (2E)-3-(4-chlorophenyl)prop-2-enoyl chloride To a solution of (2E)-3-(4-chlorophenyl)prop-2-enoic acid (2.0 g, 11 mmol) in 50 mL methylene chloride was added oxalyl chloride (1.05 mL, 12.1 mmol) and N,N-dimethylformamide (0.05 mL, 0.6 mmol). The resulting mixture was stirred at r.t. for 6 h. The solvent was removed under vacuum. The resulting solid was diluted with hexanes and the solvent removed under vacuum to provide an off-white solid which was used without further purification.

Step F: Preparation of (2E)-3-(4-chlorophenyl)-N-(2-piperidin-1-ylquinolin-6-yl)prop-2-enamide hydrochloride To a solution of the product of Step D (91 mg, 0.4 mmol) in 2 mL HOAc was added the product of Step E (64 mg, 0.32 mmol). The resulting mixture was stirred at r.t. for 3 h then diluted with 3 mL ether. The resulting mixture was filtered and the resulting solids were washed with ether. The solids were dried under vacuum to afford the product, MS: m/z 392 (MH$^+$), as an off-white solid. Using the appropriate starting materials and following procedures similar to those described above for Example 1, the following compounds were prepared from the corresponding quinoline-2,6-diamine intermediates:

| Ex. # | R₇ | R = NR₁R₂ | Parent Ion (MH⁺) m/z |
|---|---|---|---|
| 2 | 4-(trifluoromethyl)phenyl propenyl | piperidin-1-yl | 426 |
| 3 | 4-chlorophenyl propenyl | N(CH₃)₂ | 352 |
| 4 | 4-(trifluoromethyl)phenyl propenyl | N(CH₃)₂ | 386 |
| 5 | 4-chlorophenyl propenyl | NH(CH₂CH₃) (with N-CH₃) | 352 |
| 6 | 4-(trifluoromethyl)phenyl propenyl | NH(CH₂CH₃) (with N-CH₃) | 386 |
| 7 | 4-chlorophenyl propenyl | NH(CH₂CH₂CH₃) (with N-CH₃) | 366 |
| 8 | 4-chlorophenyl propenyl | NH(CH₂CH₂CH₃) (with N-CH₃) | 401 |
| 9 | 4-(trifluoromethyl)phenyl propenyl | NH-CH(CH₃)₂ (with N-CH₃) | 400 |
| 10 | 4-chlorophenyl propenyl | NH-CH(CH₃)₂ (with N-CH₃) | 366 |
| 11 | 4-(trifluoromethyl)phenyl propenyl | N-methylquinuclidinyl | 452 |
| 12 | 4-chlorophenyl propenyl | N-methylquinuclidinyl | 418 |

-continued
| Ex. # | R₇ | R = NR₁R₂ | Parent Ion (MH⁺)m/z |
|---|---|---|---|
| 13 | 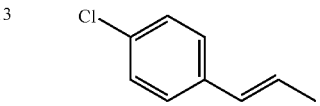 | 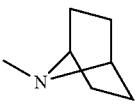 | 404 |
| 14 | 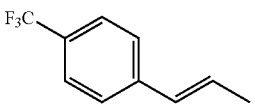 | 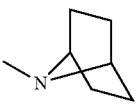 | 438 |
| 15 | 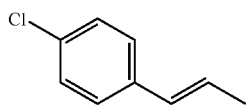 | 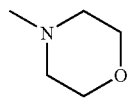 | 394 |
| 16 | 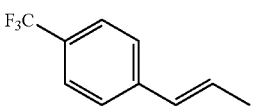 | 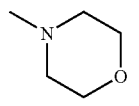 | 428 |
| 17 | 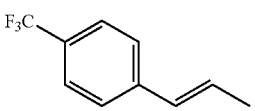 | 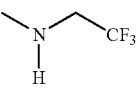 | 440 |
| 18 | 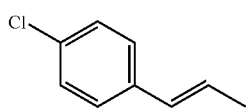 | 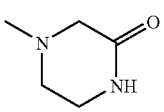 | 407 |
| 19 | 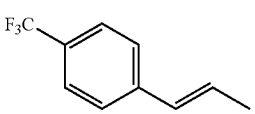 | 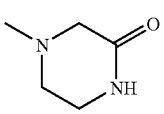 | 441 |
| 20 | 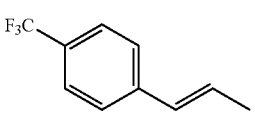 | 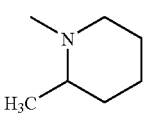 | 440 |
| 21 | 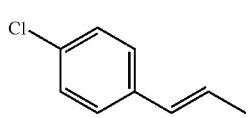 | 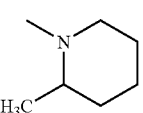 | 406 |
| 22 | 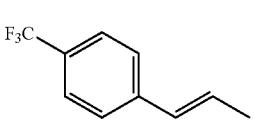 | 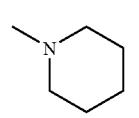 | 426 |
| 23 | 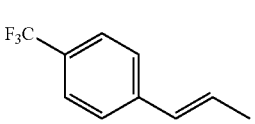 | 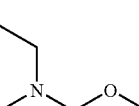 | 471 M-56 |

-continued
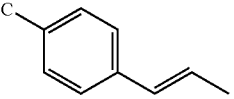
| Ex. # | R₇ | R = NR₁R₂ | Parent Ion (MH⁺)m/z |
|---|---|---|---|
| 24 | 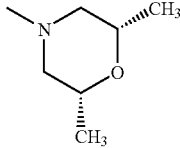 | 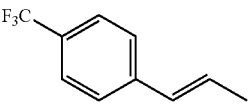 | 456 |
| 25 | 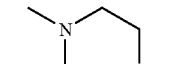 | 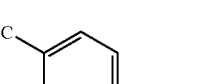 | 427 |
| 26 | 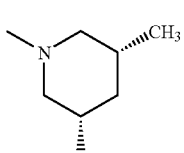 | 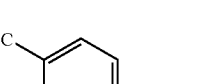 | 454 |
| 27 | 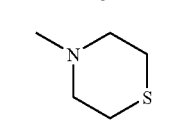 | 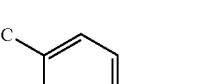 | 444 |
| 28 | 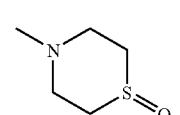 | 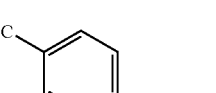 | 460 |
| 29 | 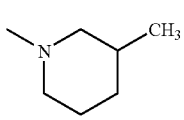 | 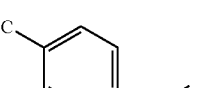 | 442 |
| 30 | 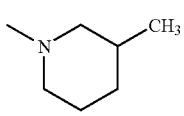 | 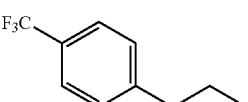 | 440 |
| 31 | 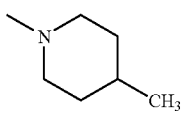 | 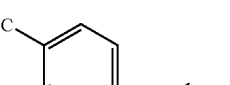 | 442 |
| 32 | 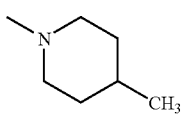 | 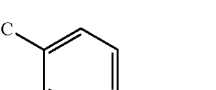 | 440 |
| 33 | 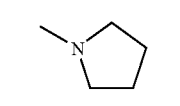 | 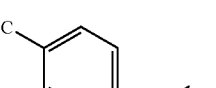 | 414 |
| 34 | 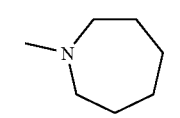 |  | 440 |

-continued

| Ex. # | R₇ | R = NR₁R₂ | Parent Ion (MH⁺)m/z |
|---|---|---|---|
| 35 | 4-(CF₃)-C₆H₄-CH₂CH₂CH₂- | N-methylazepane | 442 |
| 36 | 4-(CF₃)-C₆H₄-CH=CH- (propenyl) | N-methylpyrrolidine | 412 |
| 37 | 4-(CF₃)-C₆H₄-CH=CH- (propenyl) | N-methylazetidine | 398 |
| 38 | 4-(CF₃)-C₆H₄-CH₂CH₂CH₂- | N-methyl-2-azabicyclo[2.2.1]heptane | 440 |
| 39 | 4-(CF₃)-C₆H₄-CH₂CH₂CH₂- | N-methylazetidine | 400 |
| 40 | 4-(CF₃)-C₆H₄-CH=CH- (propenyl) | N-methyl bicyclic amine | 466 |
| 41 | 4-(CF₃)-C₆H₄-CH₂CH₂CH₂- | N-methyl bicyclic amine | 468 |
| 42 | 4-(CF₃)-C₆H₄-CH=CH- (propenyl) | N-methyl-2-azabicyclo[2.2.1]heptane | 438 |
| 43 | 4-(CF₃)-C₆H₄-CH₂CH₂CH₂- | N-methyl oxabicyclic amine | 442 |
| 44 | 4-(CF₃)-C₆H₄-CH₂CH₂CH₂- | 1-methyl-3-phenylpyrrolidine | 490 |
| 45 | 4-(CF₃)-C₆H₄-CH₂CH₂CH₂- | 1-methyl-3-methylpyrrolidine | 428 |

-continued
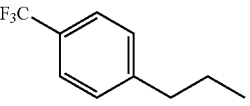
| Ex. # | R₇ | R = NR₁R₂ | Parent Ion (MH⁺)m/z |
|---|---|---|---|
| 46 | 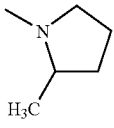 | 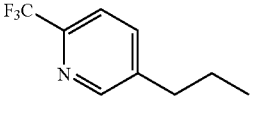 | 428 |
| 47 | 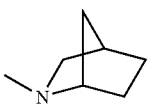 | 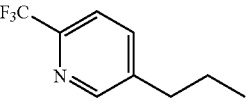 | 441 |
| 48 | 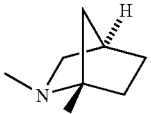 | 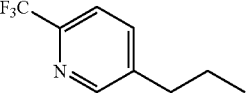 | 441 |
| 49 | 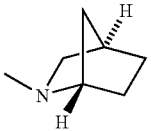 | 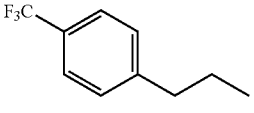 | 441 |
| 50 | 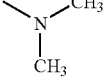 | 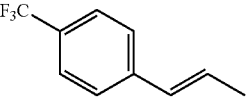 | 388 |
| 51 | 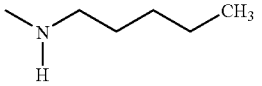 | 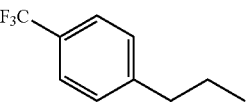 | 414 |
| 52 | 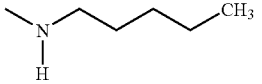 | 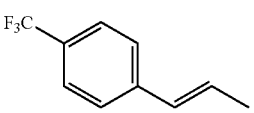 | 416 |
| 53 | 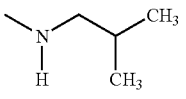 | 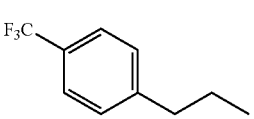 | 414 |
| 54 | 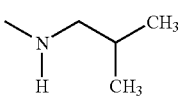 | 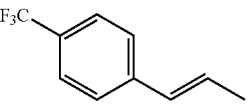 | 416 |
| 55 | 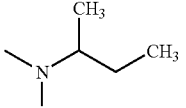 | 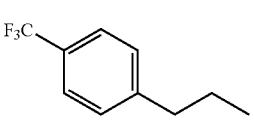 | 414 |
| 56 | 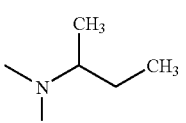 | | 416 |

-continued
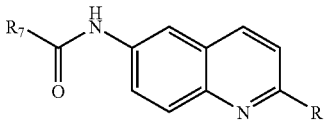
| Ex. # | R7 | R = NR1R2 | Parent Ion (MH+)m/z |
|---|---|---|---|
| 57 | 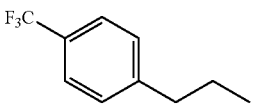 | 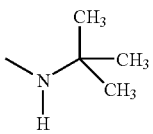 | 416 |
| 58 | 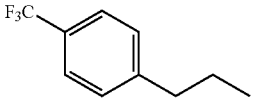 | 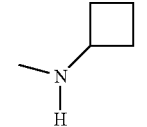 | 414 |
| 59 | 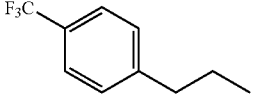 | 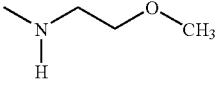 | 418 |
| 60 | 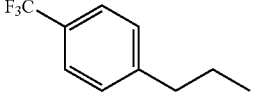 | 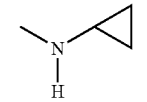 | 400 |
| 61 | 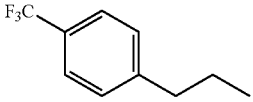 | 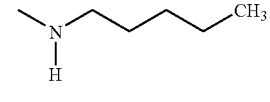 | 430 |
| 62 | 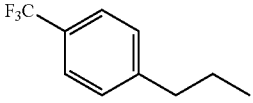 | 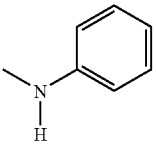 | 436 |
| 63 | 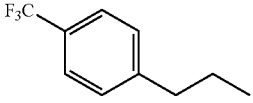 | 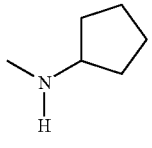 | 428 |
| 64 | 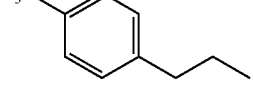 | 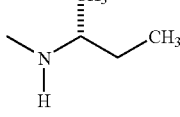 | 416 |
| 65 | 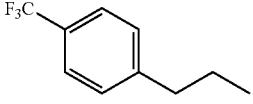 | 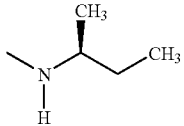 | 416 |
| 66 | 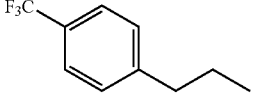 |  | 360 |

-continued

| Ex. # | R₇ | R = NR₁R₂ | Parent Ion (MH⁺) m/z |
|---|---|---|---|
| 67 | 4-(trifluoromethyl)phenyl-propyl | N-methyl cyclohexyl | 442 |
| 68 | 4-(trifluoromethyl)phenyl-propyl | N-methyl methyl | 374 |
| 69 | 4-(trifluoromethyl)phenyl-propyl | N-methyl propyl acetate | 460 |
| 70 | 4-(trifluoromethyl)phenyl-propyl | N-methyl 3-hydroxypropyl | 418 |
| 71 | 4-(trifluoromethyl)phenyl-propyl | N-methyl benzyl | 450 |
| 72 | 4-(trifluoromethyl)phenyl-propyl | N-methyl 2-methylbutyl | 430 |
| 73 | 4-(trifluoromethyl)phenyl-propyl | N-methyl 3-methylbut-2-yl | 430 |
| 74 | 4-(trifluoromethyl)phenyl-propyl | N-methyl t-pentyl | 430 |
| 75 | 6-(trifluoromethyl)pyridin-3-yl-propyl | N-methyl cyclopentyl | 429 |
| 76 | 4-(trifluoromethyl)phenyl-propyl | N-methyl 2-hydroxyethyl | 404 |

-continued
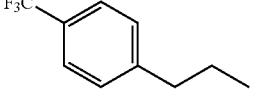
| Ex. # | R7 | R = NR1R2 | Parent Ion (MH+)m/z |
|---|---|---|---|
| 77 | 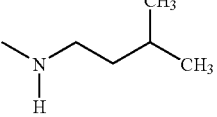 | 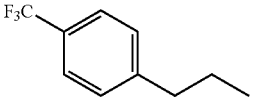 | 430 |
| 78 | 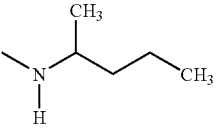 | 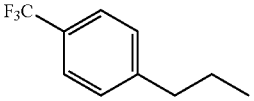 | 430 |
| 79 | 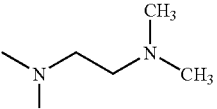 | 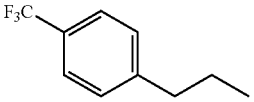 | 431 |
| 80 | 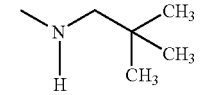 | 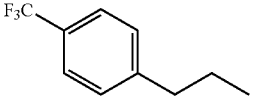 | 430 |
| 81 | 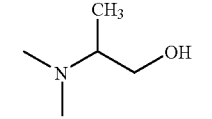 | 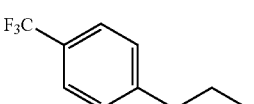 | 418 |
| 82 | 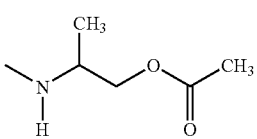 | 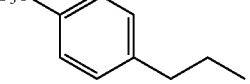 | 460 |
| 83 | 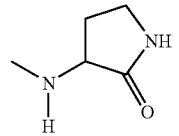 | 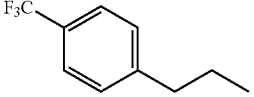 | 443 |
| 84 | 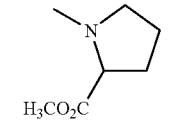 | 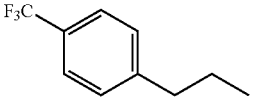 | 473 M-36 |
| 85 | 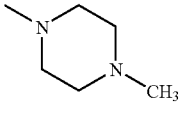 | 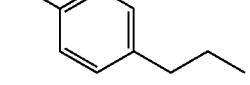 | 443 |
| 86 | 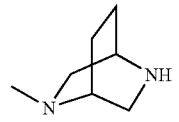 | | 455 |

-continued
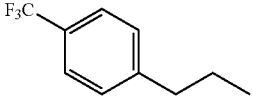
| Ex. # | R7 | R = NR1R2 | Parent Ion (MH+) m/z |
|---|---|---|---|
| 87 | 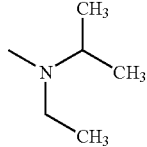 | 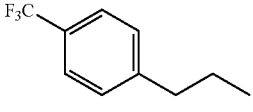 | 430 |
| 88 | 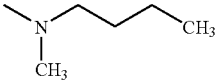 | 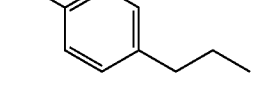 | 430 |
| 89 | 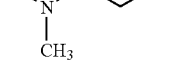 | 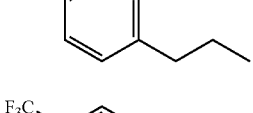 | 418 |
| 90 | 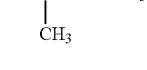 | 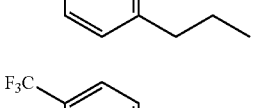 | 402 |
| 91 | 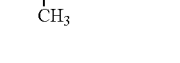 | 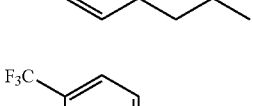 | 416 |
| 92 | 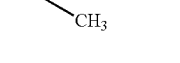 | 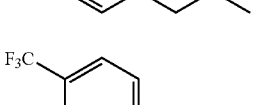 | 430 |
| 93 |  | 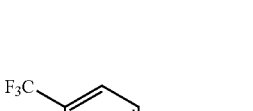 | 464 |
| 94 |  | 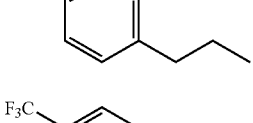 | 478 |
| 95 |  | 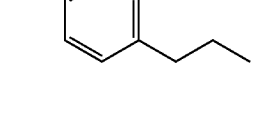 | 492 |
| 96 | 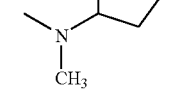 | | 442 |

-continued

| Ex. # | R₇ | R = NR₁R₂ | Parent Ion (MH⁺)m/z |
|---|---|---|---|
| 97 | 4-(CF₃)C₆H₄-CH₂CH₂CH₂- | 1-methyl-3-benzylpiperidin-3-yl (N-attached) | 518 |
| 98 | 4-(CF₃)C₆H₄-CH₂CH₂CH₂- | N(CH₃)-cyclobutyl, N-CH₃ | 428 |
| 99 | 4-(CF₃)C₆H₄-CH₂CH₂CH₂- | N(CH₃)₂-CH(CH₃)CH₂OC(O)CH₃ | 474 |
| 100 | 4-(CF₃)C₆H₄-CH₂CH₂CH₂- | N(CH₃)₂-CH₂CH(CH₃)₂ | 430 |
| 101 | 4-(CF₃)C₆H₄-CH₂CH₂CH₂- | N(CH₃)₂-CH₂CH₂CH(CH₃)₂ | 444 |
| 102 | 4-(CF₃)C₆H₄-CH₂CH₂CH₂- | N(CH₃)₂-CH(CH₃)CH₂CH₃ | 431 |
| 103 | 4-(CF₃)C₆H₄-CH₂CH₂CH₂- | N(CH₃)(CH₂CH₃)₂ → N(CH₃)(Et)₂ | 416 |
| 104 | 4-(CF₃)C₆H₄-CH₂CH₂CH₂- | N(CH₃)(CH₂CH₂CH₃)(CH₂CH₃) | 444 |
| 105 | 4-(CF₃)C₆H₄-CH₂CH₂CH₂- | N(CH₃)₂-cyclohexyl | 456 |
| 106 | 4-(CF₃)C₆H₄-CH₂CH₂CH₂- | N(CH₃)(Et)-cyclohexyl | 470 |

-continued

| Ex. # | R₇ | R = NR₁R₂ | Parent Ion (MH⁺)m/z |
|---|---|---|---|
| 107 | 4-(CF₃)-phenyl-propyl | N-methyl-N-phenyl, CH₃ | 450 |
| 108 | 4-(CF₃)-phenyl-propyl | N(CH₃)₂-isopropyl | 416 |
| 109 | 4-(CF₃)-phenyl-propyl | 1-methylpiperidin-3-yl-methanol | 458 |
| 110 | 4-(CF₃)-phenyl-propyl | N,N-dimethyl-2-methoxyethylamine | 432 |
| 111 | 4-(CF₃)-phenyl-propyl | N-methyl-isopropylamine | 402 |
| 112 | 6-(CF₃)-pyridin-3-yl-propyl | N(CH₃)₂-isopropyl | 417 |
| 113 | 4-(CF₃)-phenyl-propenyl | N(CH₃)₂-isopropyl | 414 |
| 114 | 4-Cl-phenyl-propenyl | N(CH₃)₂-isopropyl | 380 |
| 115 | 4-(CF₃)-phenyl-propyl | N,N-dimethyl-3-(pyridin-4-yl)propylamine | 479 |
| 116 | 4-(CF₃)-phenyl-propyl | N,N-dimethyl-3-(pyridin-3-yl)propylamine | 479 |

| Ex. # | R7 | R = NR1R2 | Parent Ion (MH+)m/z |
|---|---|---|---|
| 117 | F3C-C6H4-CH2CH2- | -N(CH3)-C(CH3)2-CH2-O-C(O)-CH3 | 474 |
| 118 | F3C-C6H4-CH2CH2- | -N(CH3)-CH2-C(CH3)2-CH2-O-C(O)-CH3 | 488 |

EXAMPLE 119

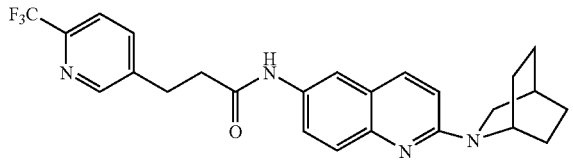

N-[2-(2-azabicyclo[2.2.2]oct-2-yl)quinolin-6-yl]-3-[6-(trifluoromethyl)pyridin-3-yl]propanamide Step A: Preparation of 2-(2-azabicyclo[2.2.2]oct-2-yl)-6-nitroquinoline A mixture of 2-chloro-6-nitroquinoline (5.0 g, 24 mmol, Example 1, Step B), 2-azabicyclo[2.2.2]octane p-toluenesulfonic acid salt (10.2 g, 36 mmol) and sodium bicarbonate (5.1 g, 60 mmol) were mixed in absolute ethanol (100 mL) and then heated at reflux for 24 h. The reaction mixture was cooled to r.t., and the solvent removed under vacuum. The solids were taken up in EtOAc (750 mL). The mixture was transferred to a separatory funnel washed with water (3×100 mL) then brine (100 mL). The organic layer was dried over sodium sulfate, filtered and the solvent removed under vacuum to afford the product as a yellow solid, MS: m/z 284 (MH+) which was used without further purification.

Step B: Preparation of 2-(2-azabicyclo[2.2.2]oct-2-yl) quinolin-6-amine

The product of Step A and palladium hydroxide on carbon (1.3 g, 20% by wt) was suspended in methanol (100 mL) and ethyl acetate (100 mL). The resulting mixture was degassed then stirred under hydrogen atmosphere (balloon) for 6 h. The reaction mixture was filtered through filter aid and the solvent removed under vacuum. The resulting oil was dissolved in ethyl acetate and the solvent removed under vacuum. The resulting oil was suspended in ether and triturated until crystallization occurred. The solids were filtered and washed with ice-cold ether then dried under vacuum to afford the product as a brown solid, MS: m/z 254 (MH+), which was used without further purification Step C: Preparation of tert-butyl 3-[6-(trifluoromethyl)pyridin-3-yl]prop-2-enoate To a solution of [6-(trifluoromethyl)pyridin-3-yl]methanol (9.6 g, 54 mmol) in methylene chloride (200 mL) under nitrogen atmosphere was added ten-butyl (triphenylphosphoranylidene)acetate (24.6 g, 65 mmol) and MnO2 (47.3 g, 544 mmol). The resulting mixture was stirred at r.t. for 24 h. then filtered through a pad of silica gel. The pad was eluted with hexanes/EtOAc (7:1) and the solvent removed under vacuum to afford the product as a white solid, MS: m/z 274 (MH+).

Step D: Preparation of tert-butyl 3-[6-(trifluoromethyl)pyridin-3-yl]propanoate

The product of Step C (2.2 g, 8.1 mmol) in 40 mL methanol and 5% palladium on carbon (0.25 g) was stirred under hydrogen atmosphere (balloon) for 1 h. The reaction mixture was filtered through filter aid and the solvent removed under vacuum to afford the product as a solid, MS: m/z 276 (MH+).

Step E: Preparation of 3-[6-(trifluoromethyl)pyridin-3-yl] propanoic acid:

To a solution of the product Step D (580 mg, 2.1 mmol) in 2 mL methylene chloride was added anisole (2 drops) and trifluoroacetic acid (1 mL). The mixture was heated at 40° C. for several hours and the solvent removed under vacuum. The resulting oil was dried in a vacuum oven at 40° C. overnight to afford the product as a semi-solid, MS: m/z 220 (MH+).

Step F: Preparation of N-[2-(2-azabicyclo[2.2.2]oct-2-yl) quinolin-6-yl]-3-[6-(trifluoromethyl)pyridin-3-yl]propanamide To a solution of the product of Step B (307 mg, 1.2 mmol), the product of Step E (404 mg, 1.2 mmol) and triethylamine (0.17 mL, 1.2 mmol) in 10 mL methylene chloride was added 4-dimethylaminopyridine (222 mg, 1.8 mmol) followed by 1-(3-dimethylaminopropyl)3-ethylcarbodiimide HCl (349 mg, 1.82 mmol). The resulting mixture was stirred at r.t. for 3 days. The solvent was removed under vacuum and residue was purified by preparative thin layer chromatography eluting with hexane/ethyl acetate/triethylamine (1:7:0.1) to afford the product, MS: m/z 455 (MH+), as an off-white solid.

Using the appropriate starting materials and following procedures similar to those described above for Example 119 or Example 1, the following compounds were prepared:

| Ex. # | R7 | R = NR1R2 | Parent Ion (MH+) m/z |
|---|---|---|---|
| 120 | methyl 4-(prop-1-enyl)benzoate | N-methyl azabicyclic | 442 |
| 121 | methyl 4-propylbenzoate | N-methyl azabicyclic | 444 |
| 122 | 4-phenyl bicyclic | N-methyl azabicyclic | 466 |
| 123 | 4'-(trifluoromethyl)-4-methylbiphenyl | N-methyl azabicyclic | 502 |
| 124 | 4-(trifluoromethyl)propylbenzene | N-methyl azabicyclic | 454 |
| 125 | 2-(4-(trifluoromethyl)phenyl)-5-methylpiperidine | N-methyl azabicyclic | 441 |
| 126 | 4-ethyl-(prop-1-enyl)benzene | N-methyl azabicyclic | 412 |
| 127 | 4-(trifluoromethyl)ethylbenzene | N-methyl azabicyclic | 440 |

-continued
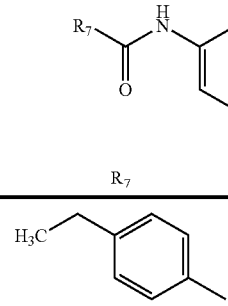
| Ex. # | R7 | R = NR1R2 | Parent Ion (MH+) m/z |
|---|---|---|---|
| 128 | 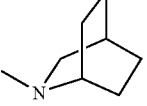 | 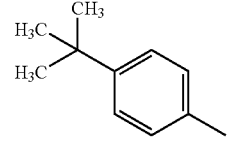 | 386 |
| 129 | 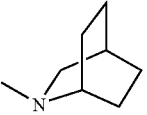 | 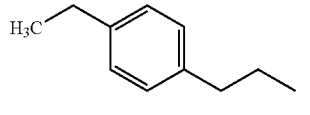 | 414 |
| 130 | 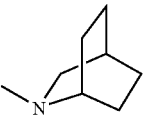 | 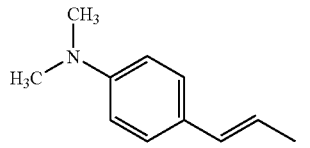 | 414 |
| 131 | 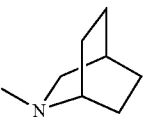 | 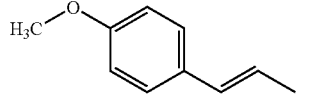 | 427 |
| 132 | 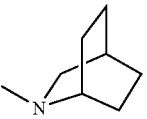 | 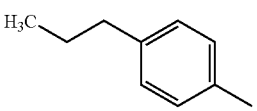 | 414 |
| 133 | 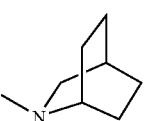 | 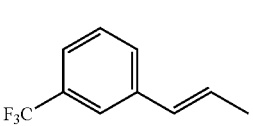 | 400 |
| 134 | 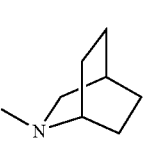 | 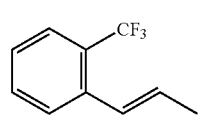 | 452 |
| 135 | 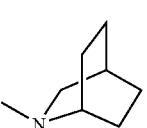 | 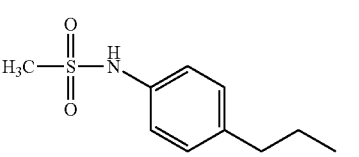 | 452 |
| 136 | 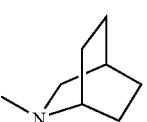 | 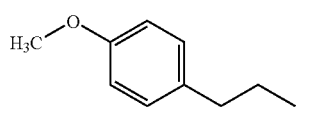 | 479 |
| 137 | 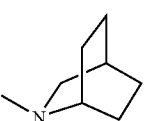 | | 416 |

-continued

| Ex. # | R7 | R = NR1R2 | Parent Ion (MH+) m/z |
|---|---|---|---|
| 138 | 4-(dimethylamino)phenyl with propyl | N-methyl azabicyclic | 429 |
| 139 | 6-(dimethylamino)pyridin-3-yl with propyl | N-methyl azabicyclic | 430 |
| 140 | 6-ethylpyridin-3-yl with propyl | N-methyl azabicyclic | 415 |
| 141 | 4-(methylsulfonyl)phenyl with propyl | N-methyl azabicyclic | 464 |
| 142 | 6-(pyrrolidin-1-yl)pyridin-3-yl with propyl | N-methyl azabicyclic | 456 |
| 143 | 4-(1H-pyrazol-1-yl)phenyl with methyl | N-methyl azabicyclic | 424 |
| 144 | 4-chlorophenyl cyclopropyl | N-methyl azabicyclic | 432 |
| 145 | 5-fluoro-1H-benzimidazol-2-yl with propyl | N-methyl azabicyclic | 444 |
| 146 | 5-(4-methoxyphenyl)furan-2-yl with methyl | N-methyl azabicyclic | 454 |

-continued
| Ex. # | R7 | R = NR1R2 | Parent Ion (MH+) m/z |
|---|---|---|---|
| 147 | 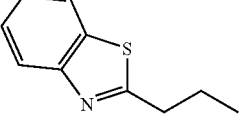 | 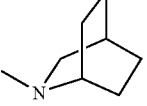 | 443 |
| 148 | 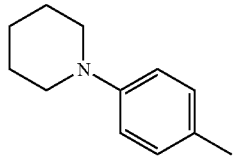 | 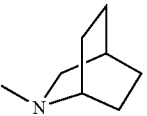 | 441 |
| 149 | 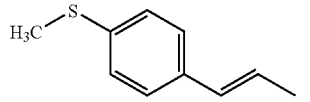 | 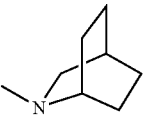 | 430 |
| 150 | 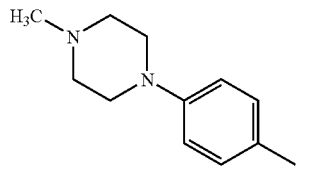 | 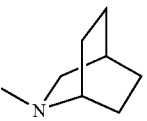 | 456 |
| 151 | 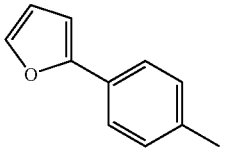 | 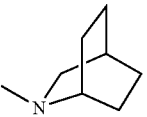 | 424 |
| 152 | 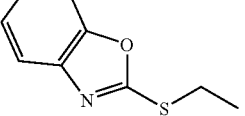 | 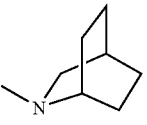 | 445 |
| 153 | 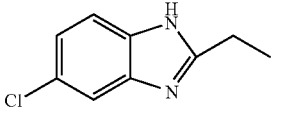 | 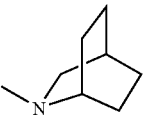 | 446 |
| 154 | 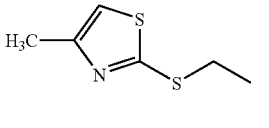 | 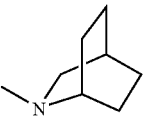 | 425 |
| 155 | 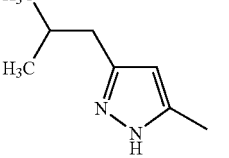 | 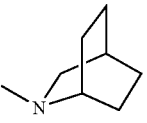 | 404 |

-continued

| Ex. # | R₇ | R = NR₁R₂ | Parent Ion (MH⁺) m/z |
|---|---|---|---|
| 156 | 3-methyl-1-propyl-pyrazol-5-yl | 1-methyl-azabicyclo[2.2.2]oct-3-yl | 390 |
| 157 | 5-methyl-3-(prop-1-enyl)-isoxazol-... | 1-methyl-azabicyclo[2.2.2]oct-3-yl | 389 |
| 158 | 4-(methylsulfonyl)phenyl-propyl | 1-methyl-azabicyclo[2.2.2]oct-3-yl | 450 |
| 159 | 2-propyl-benzothiazol-... | 1-methyl-azabicyclo[2.2.2]oct-3-yl | 429 |
| 160 | 4-(methylsulfonyl)phenyl-propyl | N(CH₃)₂-CH(CH₃)-CH₃ | 426 |
| 161 | 2-propyl-benzothiazol-... | N(CH₃)₂-CH(CH₃)-CH₃ | 405 |

EXAMPLE 162

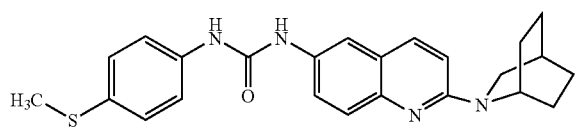

N-[2-(2-azabicyclo[2.2.2]oct-2-yl)quinolin-6-yl]-N'-[4-(methylthio)phenyl]urea

Step A: Preparation of N-[2-(2-azabicyclo[2.2.2]oct-2-yl)quinolin-6-yl]-N'-[4-(methylthio)phenyl]urea To a solution of 2-(2-azabicyclo[2.2.2]oct-2-yl)quinolin-6-amine (21 mg, 0.08 mmol, Example 119, Step B), triethylamine (0.013 mL, 0.09 mmol) in 1 mL methylene chloride was added 4-(methylthio)phenylisocyanate (15 mg, 0.09 mmol). The resulting mixture was stirred at r.t. for 2 h. The solvent was removed under vacuum and the residue was purified by preparative thin layer chromatography eluting with hexane/ethyl acetate (1:1) to afford the product, MS: m/z 419 (MH⁺), as an off-white solid.

Using the appropriate starting materials and following procedures similar to those described above for Example 162, the following compounds were prepared:

| Ex. # | R₇ | R = NR₁R₂ | Parent Ion (MH⁺) m/z |
|---|---|---|---|
| 163 | 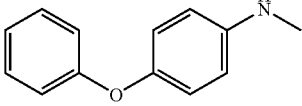 | 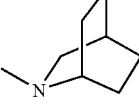 | 465 |
| 164 | 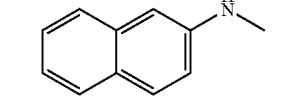 | 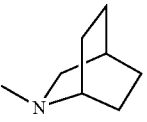 | 423 |
| 165 | 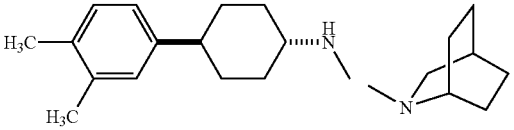 | 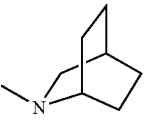 | 483 |
| 166 | 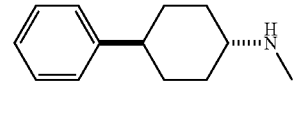 | 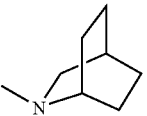 | 455 |
| 167 | 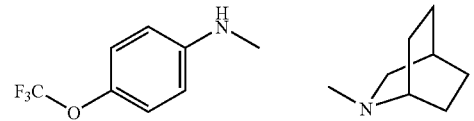 | 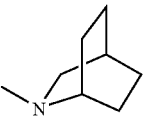 | 457 |
| 168 | 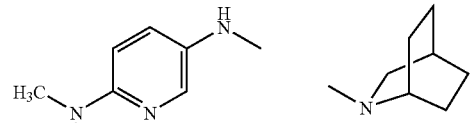 | 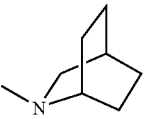 | 417 |
| 169 | 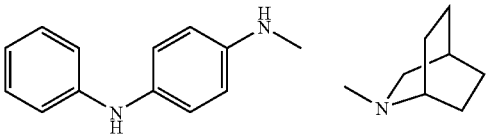 | 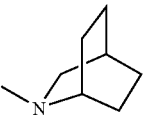 | 464 |
| 170 | 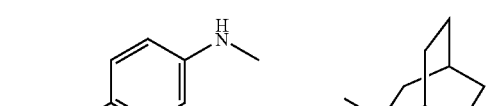 | 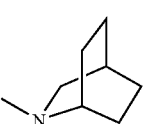 | 418 |
| 171 | 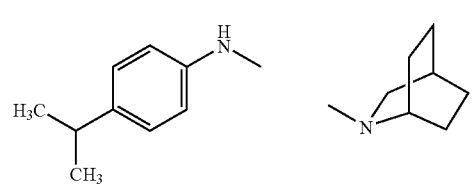 | 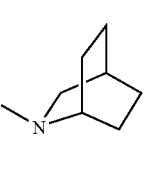 | 415 |

-continued

| Ex. # | R$_7$ | R = NR$_1$R$_2$ | Parent Ion (MH$^+$) m/z |
|---|---|---|---|
| 172 | phenyl-NHMe | N-methylquinuclidinyl | 373 |
| 173 | 4-CF$_3$-phenyl-NHMe | N-methylquinuclidinyl | 441 |
| 174 | 6-CF$_3$-pyridin-3-yl-NHMe | N-methylquinuclidinyl | 442 |
| 175 | 4-H$_2$N-phenyl-NHMe | N-methylquinuclidinyl | 388 |
| 176 | 4-H$_3$CO-phenyl-NHMe | N-methylquinuclidinyl | 403 |
| 177 | 4-(H$_3$C-S(O))-phenyl-NHMe | N-methylquinuclidinyl | 435 |
| 178 | 4-(H$_3$C-S(O)$_2$)-phenyl-NHMe | N-methylquinuclidinyl | 451 |
| 179 | 4-CF$_3$-benzyl-NHMe | N-methylquinuclidinyl | 455 |
| 180 | 4-Cl-benzyl-NHMe | N-methylquinuclidinyl | 421 |

-continued
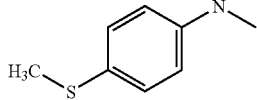
| Ex. # | R7 | R = NR1R2 | Parent Ion (MH+) m/z |
|---|---|---|---|
| 181 |  | 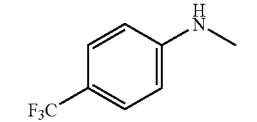 | 353 |
| 182 |  | 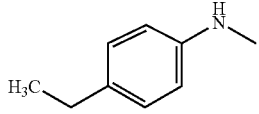 | 375 |
| 183 | 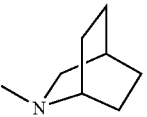 | 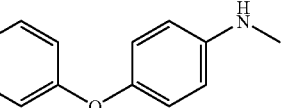 | 401 |
| 184 |  | 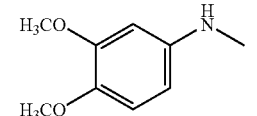 | 399 |
| 185 | 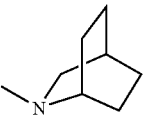 | 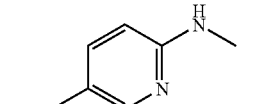 | 433 |
| 186 | 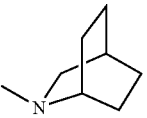 | 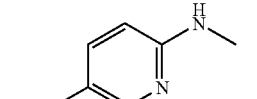 | 442 |
| 185 |  | 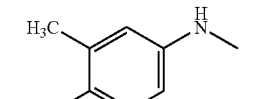 | 376 |
| 186 | 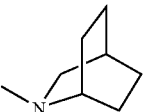 | 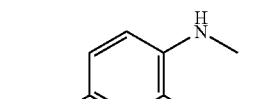 | 401 |
| 187 | 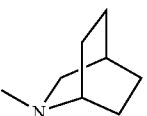 | 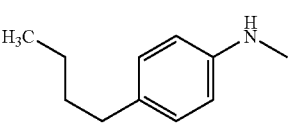 | 401 |
| 188 | 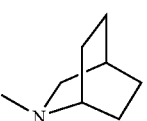 | | 429 |

-continued
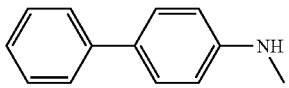
| Ex. # | R₇ | R = NR₁R₂ | Parent Ion (MH⁺) m/z |
|---|---|---|---|
| 189 | 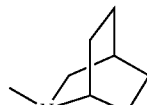 | 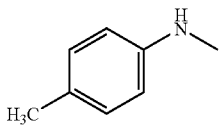 | 449 |
| 190 | 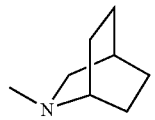 | 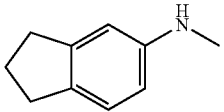 | 387 |
| 191 | 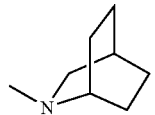 | 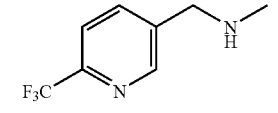 | 413 |
| 192 | 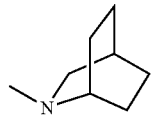 | 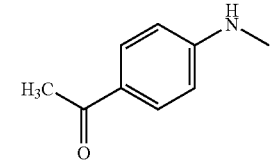 | 456 |
| 193 | 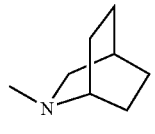 | 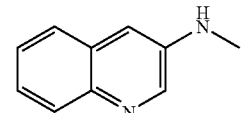 | 415 |
| 194 | 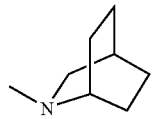 | 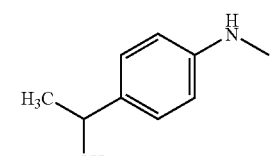 | 424 |
| 195 | 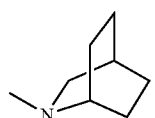 | 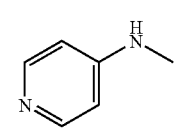 | 417 |
| 196 | 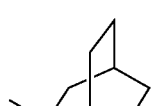 | 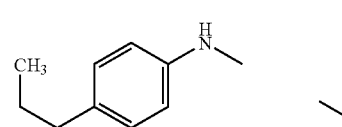 | 374 |
| 197 | 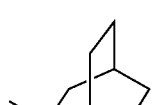 | | 415 |

-continued

| Ex. # | R₇ | R = NR₁R₂ | Parent Ion (MH⁺) m/z |
|---|---|---|---|
| 198 | 5-(methylamino)-2-ethylpyridinyl | N-methylquinuclidinyl | 416 |
| 199 | 3-(methylamino)pyridinyl | N-methylquinuclidinyl | 374 |
| 200 | 3-ethyl-N-methylanilinyl | N-methylquinuclidinyl | 401 |
| 201 | 3,5-dimethyl-N-methylanilinyl | N-methylquinuclidinyl | 401 |
| 202 | 4-(2-(BOC-amino)ethyl)-N-methylanilinyl | N-methylquinuclidinyl | 516 |
| 203 | 4-(methoxycarbonyl)-N-methylanilinyl | N-methylquinuclidinyl | 431 |
| 204 | 4-(2-aminoethyl)-N-methylanilinyl | N-methylquinuclidinyl | 416 |
| 205 | 4-(N,N-dimethylcarbamoyl)-N-methylanilinyl | N-methylquinuclidinyl | 416 |
| 206 | 4-(2-(dimethylamino)ethyl)-N-methylanilinyl | N-methylquinuclidinyl | 444 |

-continued

| Ex. # | R₇ | R = NR₁R₂ | Parent Ion (MH⁺) m/z |
|---|---|---|---|
| 207 | 2-ethyl-5-(methylamino)pyridine | N-methylquinuclidine | 402 |
| 208 | 4-(methylamino)benzonitrile | N-methylquinuclidine | 398 |
| 209 | 4-(dimethylamino)-N-methylaniline | N-methylquinuclidine | 416 |
| 210 | N,N-dimethyl-4-methylaniline (N-methyl) | N-methylquinuclidine | 401 |
| 211 | 4-cyclohexyl-N-methylaniline | N-methylquinuclidine | 455 |
| 212 | 5,6,7,8-tetrahydronaphthalen-1-yl-methylamine | N-methylquinuclidine | 427 |
| 213 | 5,6,7,8-tetrahydronaphthalen-2-yl-methylamine | N-methylquinuclidine | 427 |
| 214 | N-acetyl-N'-methyl-p-phenylenediamine | N-methylquinuclidine | 430 |
| 215 | 4-fluoro-N-methylaniline | N-methylquinuclidine | 391 |

-continued

| Ex. # | R7 | R = NR1R2 | Parent Ion (MH+) m/z |
|---|---|---|---|
| 216 | 5-(methylamino)-2-methylpyridin-yl | N-methylquinuclidinyl | 461 |
| 217 | 4-(methylamino)phenyl-NH-CHO | N-methylquinuclidinyl | 416 |
| 218 | 5-(methylamino)-2-methoxypyridin-yl | N-methylquinuclidinyl | 404 |
| 219 | 4-(methylamino)-SCF3-phenyl | N-methylquinuclidinyl | 509 |
| 220 | 4-(methylamino)-C(O)CH2-phenyl | N-methylquinuclidinyl | 416 |
| 221 | 4-(methylamino)-C(O)NHCH3-phenyl | N-methylquinuclidinyl | 430 |
| 222 | 5-(methylamino)-2-isopropylpyridin-yl | N-methylquinuclidinyl | 416 |
| 223 | 4-(methylamino)-ethyl-phenyl | N-methylquinuclidinyl | 387 |
| 224 | 4-(methylamino)-SCF3-phenyl | N-methylquinuclidinyl | 459 |

-continued

| Ex. # | R₇ | R = NR₁R₂ | Parent Ion (MH⁺) m/z |
|---|---|---|---|
| 225 | 4-(methylthio)phenyl-NH | 1-methyl-azabicyclo[2.2.2]octyl | 405 |
| 226 | 4-(trifluoromethoxy)phenyl-NH | 1-methyl-azabicyclo[2.2.2]octyl | 443 |
| 227 | 5,6,7,8-tetrahydroquinolin-3-yl-NH | 1-methyl-azabicyclo[2.2.2]octyl | 428 |
| 228 | 6-isopropylpyridin-3-yl-NH | 1-methyl-azabicyclo[2.2.2]octyl | 402 |
| 229 | 4-methoxyphenyl-NH | 1-methyl-azabicyclo[2.2.2]octyl | 389 |
| 230 | 4-carboxyphenyl-NH | 1-methyl-azabicyclo[2.2.2]octyl | 417 |
| 231 | 4-(pyrrolidin-1-ylcarbonyl)phenyl-NH | 1-methyl-azabicyclo[2.2.2]octyl | 470 |
| 232 | 4-(morpholin-4-ylcarbonyl)phenyl-NH | 1-methyl-azabicyclo[2.2.2]octyl | 486 |
| 233 | 2-(trifluoromethyl)pyrimidin-5-yl-NH | 1-methyl-azabicyclo[2.2.2]octyl | 443 |

-continued
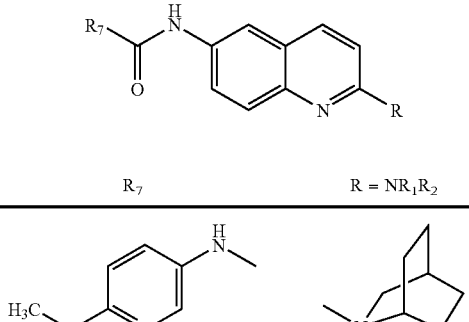
| Ex. # | R₇ | R = NR₁R₂ | Parent Ion (MH⁺) m/z |
|---|---|---|---|
| 234 | 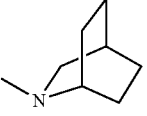 | 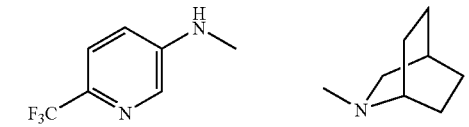 | 390 |
| 235 | 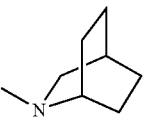 | 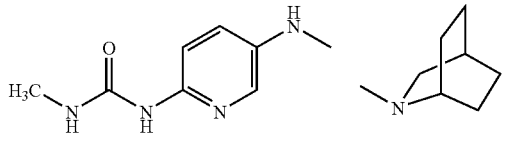 | 428 |
| 236 | 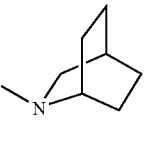 | 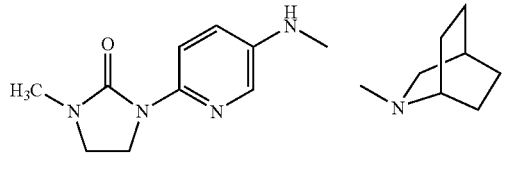 | 445 |
| 237 | 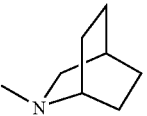 | 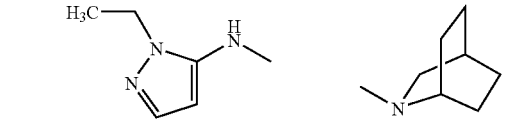 | 471 |
| 238 | 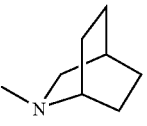 | 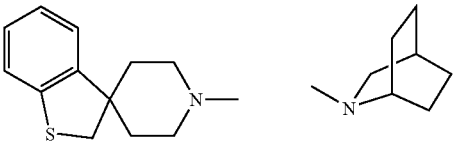 | 391 |
| 239 | 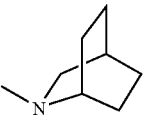 | 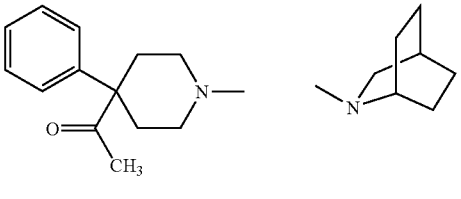 | 485 |
| 240 | 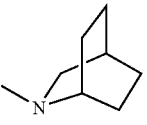 | 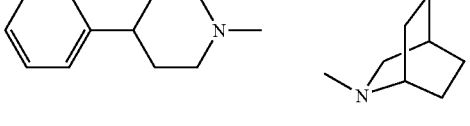 | 483 |
| 241 | 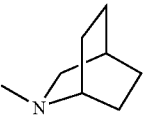 | 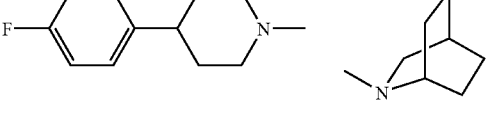 | 441 |
| 242 | 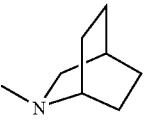 |  | 459 |

-continued

| Ex. # | R7 | R = NR1R2 | Parent Ion (MH+) m/z |
|---|---|---|---|
| 243 | 3-(trifluoromethyl)phenyl-4-hydroxy-1-methylpiperidin-4-yl | 1-methylquinuclidin-3-yl | 525 |
| 244 | 4-chloro-3-(trifluoromethyl)phenyl-4-hydroxy-1-methylpiperidin-4-yl | 1-methylquinuclidin-3-yl | 559 |
| 245 | 1-methyl-4-phenylpiperidin-4-yl | N(CH3)2 | 375 |
| 246 | 1-methyl-4-(4-fluorophenyl)piperidin-4-yl | N(CH3)2 | 393 |
| 247 | 4-acetyl-1-methyl-4-phenylpiperidin-4-yl | N(CH3)2 | 417 |
| 248 | 1'-methylspiro[benzo[b]thiophene-3(2H),4'-piperidine]-3-yl | N(CH3)2 | 419 |
| 249 | 1-methyl-4-phenyl-2,5-dihydro-1H-pyrrol-3-yl | 1-methylquinuclidin-3-yl | 425 |
| 250 | 1-methyl-3-phenylpyrrolidin-3-yl | 1-methylquinuclidin-3-yl | 427 |
| 251 | 1-methylindolin-7-yl | 1-methylquinuclidin-3-yl | 399 |

-continued
| Ex. # | R$_7$ | R = NR$_1$R$_2$ | Parent Ion (MH$^+$) m/z |
|---|---|---|---|
| 252 | 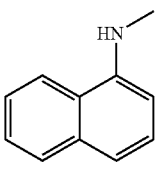 | 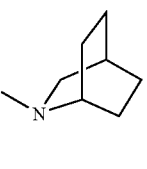 | 423 |
| 253 | 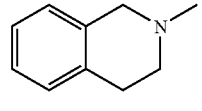 | 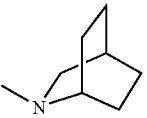 | 413 |
| 254 | 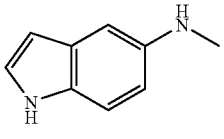 | 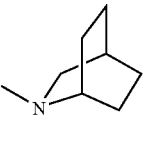 | 412 |
| 255 | 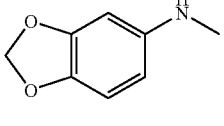 | 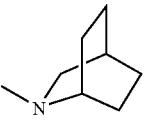 | 417 |
| 256 | 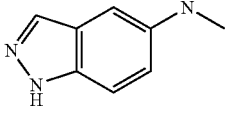 | 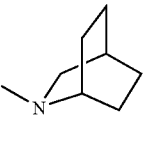 | 413 |
| 257 | 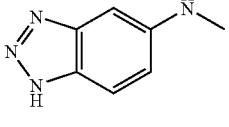 | 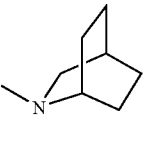 | 414 |
| 258 | 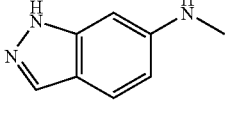 | 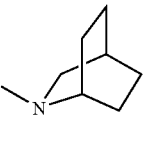 | 413 |
| 259 | 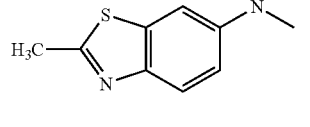 | 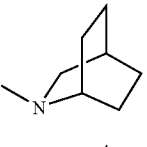 | 444 |
| 260 | 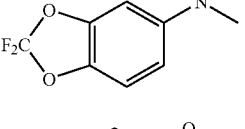 | 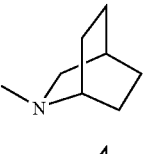 | 453 |
| 261 |  | 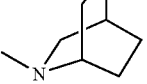 | Not obtained |

-continued

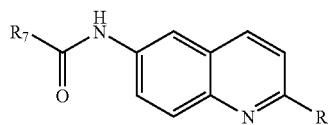

| Ex. # | R₇ | R = NR₁R₂ | Parent Ion (MH⁺) m/z |
|---|---|---|---|
| 262 | benzothiazol-6-yl-NH | N-methylazabicyclo | 430 |
| 263 | 1,3-dihydroisobenzofuran-5-yl-NH | N-methylazabicyclo | 415 |
| 264 | 1-acetylindolin-5-yl-NH | N-methylazabicyclo | 456 |
| 265 | indol-5-yl N,N-dioxide-NH | N-methylazabicyclo | 461 |
| 266 | 2,2-difluoro-1,3-benzodioxol-5-yl-NH | N-methylazabicyclo | 439 |
| 267 | 2-methylbenzothiazol-6-yl-NH | N-methylazabicyclo | 430 |
| 268 | benzothiazol-5-yl-NH | N-methylazabicyclo | 430 |
| 269 | benzimidazol-5-yl-NH | N-methylazabicyclo | 400 |
| 270 | thieno[2,3-b]pyridin-5-yl-NH | N-methylazabicyclo | 416 |

-continued
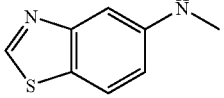
| Ex. # | R₇ | R = NR₁R₂ | Parent Ion (MH⁺) m/z |
|---|---|---|---|
| 271 | 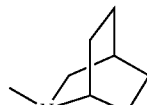 | 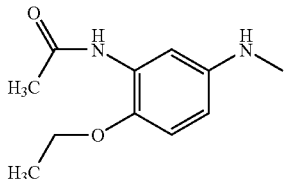 | 416 |
| 272 | 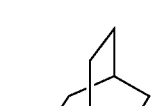 | 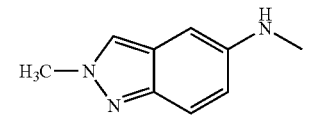 | 474 |
| 273 | 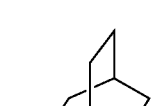 | 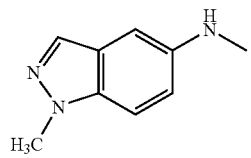 | 427 |
| 274 | 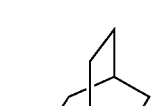 | 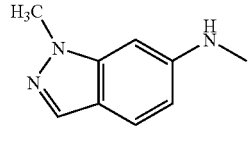 | 427 |
| 275 | 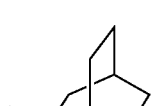 | 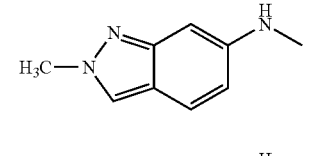 | 427 |
| 276 | 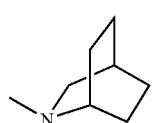 | 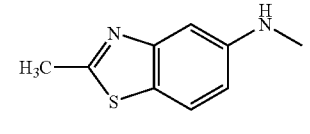 | 427 |
| 277 | 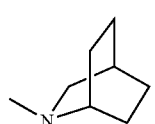 | 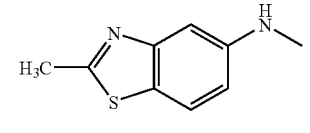 | 429 |
| 278 | 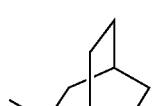 | 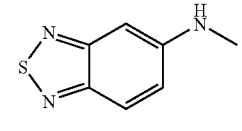 | 443 |
| 279 | 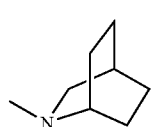 |  | 431 |

-continued

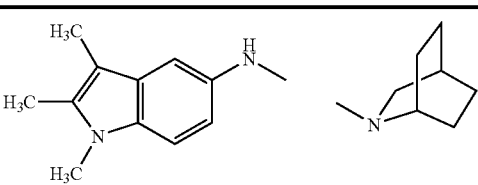

| Ex. # | R7 | R = NR1R2 | Parent Ion (MH+) m/z |
|---|---|---|---|
| 280 | 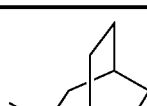 | 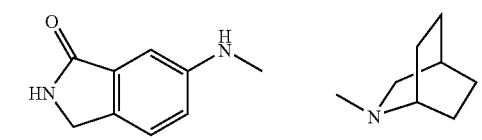 | 440 |
| 281 | 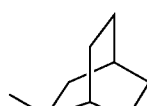 | | 464 |

EXAMPLE 282

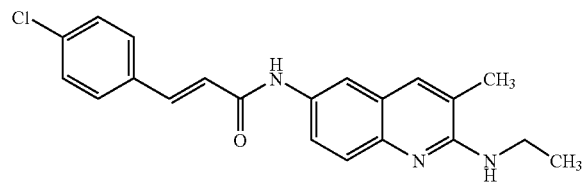

(2E)-3-(4-Chlorophenyl)-N-[2-(ethylamino)-3-methylquinolin-6-yl]prop-2-enamide hydrochloride Step A: Preparation of 2-chloro-3-methyl-6-nitroquinoline To a solution of 4-nitroaniline (10 g, 72 mmol) in chloroform at 0° was added propionyl chloride (7 mL, 80 mol) followed by triethylamine (11.1 mL). The resulting solution was stirred for 2 h at r.t. at which time the reaction mixture was washed with aq. 2N HCl. The organic layer was dried filtered and the solvent removed under vacuum to provide a solid. A solution of phosphorous oxychloride (25 mL) and N,N-dimethylformamide (4.5 mL) was stirred at 0° for 0.15 h then the above solid was added. The resulting reaction mixture was heated at 75° for 12 h at which time the volatiles were removed under vacuum. The residue was cooled in an ice bath. To the cooled mixture was carefully added water (50 mL). The resulting solids were filtered and then washed with water. The solids were extracted with chloroform, the extracts were combined, dried, filtered and the solvent removed under vacuum to afford the product, MS: m/z 224 (MH+), which was used directly in the next step.

Step B: Preparation of N-ethyl-3-methyl-6-nitroquinolin-2-amine

The product (1 g, 4.5 mmol) from Step A and a solution of 2N ethylamine in methanol (5 mL, 25 mmol) were used to prepare the product according to the procedure of Example 1, Step C.

Step C: Preparation of $N^2$-ethyl-3-methylquinoline-2.6-diamine

The product (0.8 g) of Step B and platinum oxide on carbon (~80 mg) was suspended in methanol. The resulting mixture was hydrogenated at 50 PSI for 1 h. The reaction mixture was filtered through filter aid and the solvent removed under vacuum to afford the product, which was used without further purification.

Step D: Preparation of (2E)-3-(4-Chlorophenyl)-N-[2-(ethylamino)-3-methylquinolin-6-yl]prop-2-enamide hydrochloride According to the procedure for Example 1, Step F, the product of Step C (35 mg, 0.17 mmol) and (2E)-3-(4-chlorophenyl)prop-2-enoyl chloride, Example 1, Step E (38 mg, 0.19 mmol) were utilized to afford the product, MS: m/z 367 (MH+), as an off-white solid.

Using the appropriate starting materials and following procedures similar to those described above, the following compounds were prepared from the corresponding quinoline-2,6-diamine intermediates:

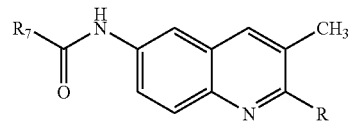
| Ex. # | R<sub>7</sub> | R = NR₁R₂ | Parent Ion (MH+) m/z |
|---|---|---|---|
| 283 | F₃C-C₆H₄-CH=CH- | -N(CH₃)₂ | 400 |
| 284 | Cl-C₆H₄-CH=CH- | -N(CH₃)₂ | 366 |
| 285 | F₃C-C₆H₄-CH₂CH₂- | -N(CH₃)₂ | 402 |
| 286 | F₃C-C₆H₄-CH=CH- | N-methylquinuclidinyl | 466 |
| 287 | Cl-C₆H₄-CH=CH- | N-methylquinuclidinyl | 432 |
| 288 | F₃C-C₆H₄-CH₂CH₂- | N-methylquinuclidinyl | 468 |
| 289 | F₃C-C₆H₄-CH=CH- | morpholinyl | 442 |
| 290 | F₃C-C₆H₄-CH₂CH₂- | morpholinyl | 444 |
| 291 | 4-F₃C-C₆H₄-NH-CH₂- | -N(CH₃)₂ | 389 |
| 292 | 4-F₃C-C₆H₄-NH-CH₂- | morpholinyl | 431 |
| 293 | F₃C-C₆H₄-CH₂CH₂- | N-methyl-2-azabicyclo | 454 |

-continued
| Ex. # | R7 | R = NR1R2 | Parent Ion (MH+) m/z |
|---|---|---|---|
| 294 | 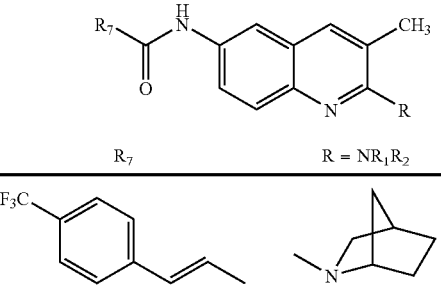 | 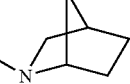 | 452 |
| 295 | 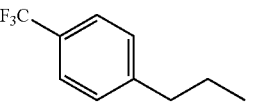 | 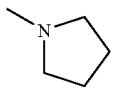 | 428 |
| 296 | 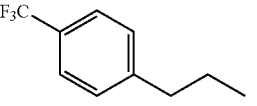 | 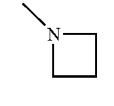 | 414 |
| 297 | 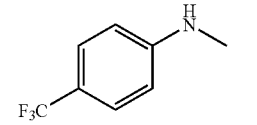 | 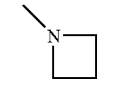 | 401 |
| 298 | 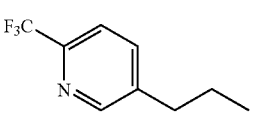 | 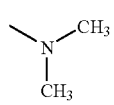 | 403 |
| 299 | 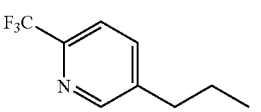 | 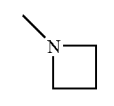 | 415 |
| 300 | 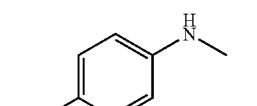 | 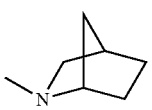 | 441 |
| 301 | 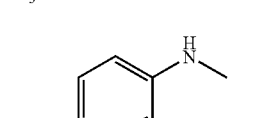 | 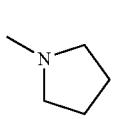 | 415 |
| 302 | 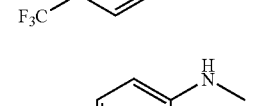 |  | 457 |
| 303 | 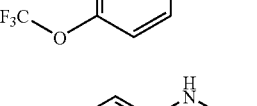 | 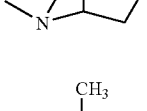 | 417 |
| 304 | 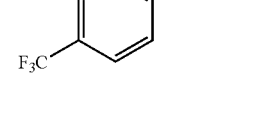 | 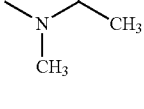 | 430 |

-continued

| Ex. # | R₇ | R = NR₁R₂ | Parent Ion (MH+) m/z |
|---|---|---|---|
| 305 | F₃C-pyridyl-CH₂CH₂- | -N(CH₃)₂ with CH(CH₃)₂ (N,N-dimethyl-isopropylamino) | 431 |
| 306 | F₃C-pyridyl-CH₂CH₂- | 2-azabicyclo[2.2.1]heptyl (N-methyl) | 455 |
| 307 | F₃C-pyridyl-CH₂CH₂- | 1-azabicyclo[2.2.2]octyl (N-methyl) | 469 |
| 308 | 4'-(trifluoromethyl)biphenyl-4-yl | 1-azabicyclo[2.2.2]octyl (N-methyl) | 516 |
| 309 | 6-phenylpyridin-3-yl | 1-azabicyclo[2.2.2]octyl (N-methyl) | 449 |
| 310 | 3-phenyladamantan-1-yl | 1-azabicyclo[2.2.2]octyl (N-methyl) | 480 |

EXAMPLE 311

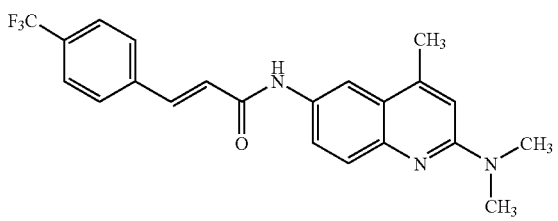

(2E)-N-[2-(Dimethylamino)-4-methylquinolin-6-yl]-3-[4-(trifluoromethyl)phenyl]prop-2-enamide hydrochloride Step A: Preparation of 2-chloro-4-methyl-6-nitroquinoline To a solution of 4-methylquinolin-2(1H)-one (11 g, 69 mmol) in concentrated sulfuric acid (100 mL) was added fuming nitric acid (2.7 mL, 80 mol). The temperature of the resulting solution rose to approximately 50°. The reaction mixture was heated at reflux for 1 h, cooled to r.t and carefully poured onto ice. The resulting precipitate was filtered, washed with ice cold water and ether, then dried under vacuum to provide a solid. A mixture of the solid (8.5 g) and phosphorous oxychloride (40 mL) was heated at 100° for 0.45 h at which time the volatiles were removed under vacuum. The residue was cooled in an ice bath. To the cooled mixture was carefully added water (50 mL). The resulting solids were filtered then washed with water and ether and then dried under vacuum to afford the product, MS: m/z 224 (MH⁺), which was used directly in the next step.

Step B: Preparation of N,N,4-trimethyl-6-nitroquinolin-2-amine

The product was obtained from the product of Step A and a solution of 2N dimethylamine in methanol (5 mL, 25 mmol) according to the procedure of Example 1, Step C.

Step C: Preparation of $N^2,N^2$,4-trimethylquinoline-2,6-diamine

The product was obtained from the product of Step B according to the procedure of Example 282, Step C.

Step D: Preparation of (2E)-N-[2-(dimethylamino)-4-methylquinolin-6-yl]-3-[4-(trifluoromethyl)phenyl]prop-2-enamide hydrochloride The product was obtained from the product of Step D (35 mg, 0.17 mmol) and (2E)-3-((4-trifluoromethyl)phenyl) prop-2-enoyl chloride according to the procedure for Example 1, Step F, MS: m/z 400 (MH$^+$).

Using the appropriate starting materials and following procedures similar to those described above, the following compounds were prepared from the corresponding quinoline-2,6-diamine intermediates:

then extracted with excess chloroform. The combined organic extracts were washed with saturated sodium bicarbonate, dried over sodium sulfate, filtered and the solvent removed under vacuum to provide a solid.

Step B: Preparation of 2-chloro-4-ethyl-6-nitroquinoline

The product was obtained from 4-ethylquinolin-2(1H)-one (Step A) according to the procedure for Example 311, Step A, MS: m/z 237 (MH$^+$), which was used directly in the next step.

| Ex. # | R$_7$ | R$_4$ | R = NR$_1$R$_2$ | Parent Ion (MH+) m/z |
|---|---|---|---|---|
| 312 | F$_3$C-C$_6$H$_4$-CH$_2$CH$_2$- | —CH$_3$ | N(CH$_3$)$_2$ | 402 |
| 313 | F$_3$C-C$_6$H$_4$-CH=CH- | —CH$_3$ | quinuclidinyl | 466 |
| 314 | F$_3$C-C$_6$H$_4$-CH$_2$CH$_2$- | —CH$_3$ | quinuclidinyl | 468 |

EXAMPLE 315

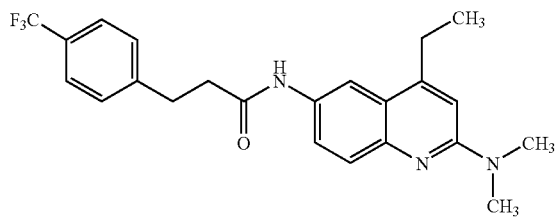

N-[2-(Dimethylamino)-4-ethylquinolin-6-yl]-3-[4-(trifluoromethyl)phenyl]propanamide hydrochloride Step A: Preparation of 4-ethylquinolin-2(1H)-one To a suspension of 4-methylquinolin-2(1H)-one (5 g, 31 mmol) in anhydrous tetrahydrofuran (100 mL) under a nitrogen atmosphere cooled in an acetone/dry ice bath was added dropwise by syringe a 1.6N solution of n-butyl lithium in hexanes (49 mL, 78 mol). The resulting solution was warmed to r.t. for 2 h at which time iodomethane (3 mL, 47 mmol) was added by syringe. The reaction mixture was stirred at r.t. for 0.5 h then cooled in an ice bath. The reaction mixture was quenched by the addition of aq. 2N HCl and Step C: Preparation of 4-ethyl-N$^2$,N$^2$-dimethyl-6-nitroquinolin-2-amine The product was obtained from the product of Step B and a solution of 2N dimethyl-amine in methanol (5 mL, 25 mmol) according to the procedure of Example 1, Step C.

Step D: Preparation of 4-ethyl-N$^2$,N$^2$-dimethylquinoline-2,6-diamine

The product was obtained from the product of Step C according to the procedure of Example 282, Step C.

Step E: 3-[(4-Trifluoromethyl)phenyl]propanoyl chloride

The product was obtained from 3-[(4-trifluoromethyl) phenyl]propanoic acid and oxalyl chloride according to the procedure for Example 1, Step E.

Step F Preparation of N-[2-(dimethylamino)-4-ethylquinolin-6-yl]-3-[4-(trifluoromethyl)phenyl]propanamide hydrochloride The product was obtained from the product of Step D (35 mg, 0.17 mmol) and 3-((4-trifluoromethyl)phenyl)propanoyl chloride according to the procedure for Example 1, Step F, MS: m/z 417 (MH$^+$).

Using the appropriate starting materials and following procedures similar to those described above, the following compounds were prepared from the corresponding quinoline-2,6-diamine intermediates:

| Ex. # | R7 | R4 | R = NR1R2 | Parent Ion (MH+) m/z |
|---|---|---|---|---|
| 316 | 4-(trifluoromethyl)phenyl-CH=CH-CH3 | —CH2CH3 | pyrrolidinyl | 440 |
| 317 | 4-(trifluoromethyl)phenyl-CH2CH2- | —CH2CH3 | pyrrolidinyl | 442 |
| 318 | 4-(trifluoromethyl)phenyl-N(CH3)- | —CH2CH3 | N(CH3)2 | 402 |

EXAMPLE 319

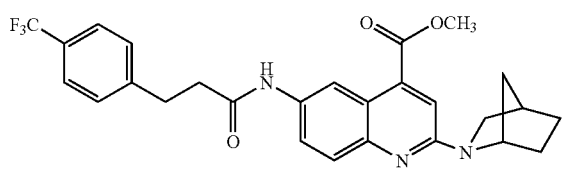

Methyl 2-(2-azabicyclo[2.2.1]hept-2-yl)-6-({3-[4-(trifluoromethyl)phenyl]propanoyl}amino)quinoline-4-carboxylate Step A: Preparation of methyl 2-oxo-1,2-dihydroquinoline-4-carboxylate In a heavy-walled PYREX tube was placed 2-iodoaniline (2.84 g, 13 mmol), dimethylmaleate (2.44 g, 17 mmol), triethylamine (1.4 mL, 10 mmol), palladium diacetate (31 mg, 0.14 mmol) and 6 mL acetonitrile. The tube was flushed with nitrogen and sealed. The sealed tube was heated at 100° for 3.5 h then cooled to r.t. The tube was opened and the resulting solids filtered and washed with acetonitrile. The solids were dissolved in chloroform and the solvent removed under vacuum to provide a solid.

Step B: Preparation of methyl 2-chloro-6-nitroquinoline-4-carboxylate

The product was obtained from methyl 2-oxo-1,2-dihydroquinoline-4-carboxylate (Step A) according to the procedure for Example 311, Step A, MS: m/z 267 (MH$^{30}$), which was used directly in the next step.

Step C: Preparation of methyl 2-(2-azabicyclo[2.2.1]hept-2-yl)-6-nitroquinoline-4-carboxylate The product was obtained from methyl 2-chloro-6-nitroquinoline-4-carboxylate (Step B) and 2-azabicyclo[2.2.1]heptane according to the procedure for Example 1, Step C.

Step D: Preparation of methyl 6-amino-2-(2-azabicyclo[2.2.1]hept-2-yl)quinoline-4-carboxylate The product was obtained from methyl 2-(2-azabicyclo[2.2.1]hept-2-yl)-6-nitro-quinoline-4-carboxylate (Step C) according to the procedure for Example 282, Step C.

Step E: Preparation of methyl 2-(2-azabicyclo[2.2.1]hept-2-yl)-6-({3-[4-(trifluoromethyl)phenyl]propanoyl}amino)quinoline-4-carboxylate The product was obtained from methyl 6-amino-2-(2-azabicyclo[2.2.1]hept-2-yl)quinoline-4-carboxylate (Step D) (35 mg, 0.17 mmol) and 3-[(4-trifluoromethyl)phenyl]propanoyl chloride (Example 315, Step E) according to the procedure for Example 1, Step F, MS: m/z 498 (MH$^+$).

Using the appropriate starting materials and following procedures similar to those described above, the following compounds were prepared from the corresponding quinoline-2,6-diamine intermediates:

| Ex. # | R7 | R4 | R = NR1R2 | Parent Ion (MH+) m/z |
|---|---|---|---|---|
| 320 | 4-(F3C)C6H4-NH-CH2- | —CO2CH3 | 2-azabicyclo[2.2.1]heptyl (N-methyl) | 485 |

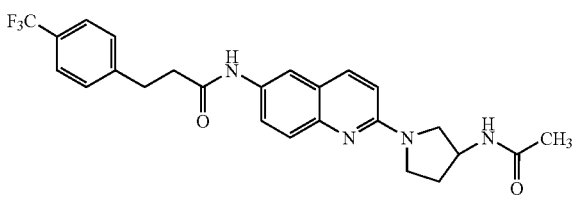

EXAMPLE 321

N-{2-[3-(Acetylamino)pyrrolidin-1-yl]quinolin-6-yl}-3-[4-(trifluoromethyl)phenyl]propanamide hydrochloride Step A: Preparation of tert-butyl 1-(6-nitroquinolin-2-yl)pyrrolidin-3-ylcarbamate The product was obtained from 2-chloro-6-nitroquinoline (Example 1, Step B) and tert-butyl pyrrolidin-3-ylcarbamate according to the procedure of Example 119, Step A, MS: m/z 359 (MH+).

Step B: Preparation of tert-butyl 1-(6-aminoquinolin-2-yl)pyrrolidin-3-ylcarbamate The product was obtained from tert-butyl 1-(6-nitroquinolin-2-yl)pyrrolidin-3-ylcarbamate (Step A) according to the procedure for Example 1, Step D, MS: m/z 329 (MH+), which was used directly in the next step.

Step C: tert-Butyl 1-[6-({3-[4-(trifluoromethyl)phenyl]propanoyl}amino)quinolin-2-yl]pyrrolidin-3-ylcarbamate hydrochloride The product was obtained from tert-butyl 1-(6-aminoquinolin-2-yl)pyrrolidin-3-yl carbamate (Step B) and 3-[(4-trifluoromethyl)phenyl]propanoyl chloride (Example 319, Step E) according to the procedure for Example 1, Step F, MS: m/z 529 (MH+).

Step D: Preparation of N-[2-(3-aminopyrrolidin-1-yl)quinolin-6-yl]-3-[4-(trifluoromethyl)phenyl]propanamide bis trifluoroacetic acid salt To a solution of tert-butyl 1-[6-({3-[4-(trifluoromethyl)phenyl]propanoyl}amino)quinolin-2-yl]pyrrolidin-3-yl carbamate hydrochloride (800 mg, 1.42 mmol; Step C) in methylene chloride (5 mL) was added anisole (0.77 mL, 7.1 mmol) and trifluoroacetic acid (5 mL). The resulting solution was stirred at r.t. for several hours and then the solvent was removed under vacuum. The resulting oil was left at r.t overnight. The residue was triturated with ethyl acetate and the resulting solids filtered, washed with ice cold ethyl acetate and dried under vacuum to afford the product, MS: m/z 429 (MH+), as an off-white solid.

Step E: N-2-[3-(Acetylamino)pyrrolidin-1-yl]quinolin-6-yl)-3-[4-(trifluoromethyl)phenyl]propanamide hydrochloride To a suspension of N-[2-(3-aminopyrrolidin-1-yl)quinolin-6-yl]-3-[4-(trifluoro-methyl)phenyl]propanamide bis trifluoroacetic acid salt (100 mg, 0.15 mmol; Step D) in methylene chloride (1 mL) at r.t. under nitrogen atmosphere was added by syringe triethylamine (0.07 mL, 0.5 mmol). To the resulting solution was added by syringe acetyl chloride (0.012 mL, 0.16 mol). The resulting mixture was stirred at r.t for several hours, during which time a precipitate formed. The solids were filtered and washed with minimal amount of solvent. The solids were taken up in methanol and treated with a solution of 2N HCl in ethanol (0.2 mL). The solvent was removed under vacuum to provide an oil which was crystallized by trituration with ethyl acetate. The solvent was removed under vacuum to provide the product, MS: m/z 471 (MH+), as an off-white solid.

Using the appropriate starting materials and reagents and following procedures similar to those described above, the following compounds were prepared from the corresponding intermediates:

| Ex. # | R₇ | R = NR₁R₂ | Parent Ion (MH+) m/z |
|---|---|---|---|
| 322 | 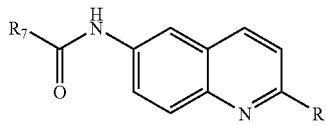 | 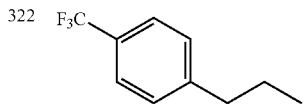 | 486 |
| 323 | 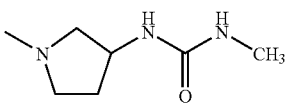 | 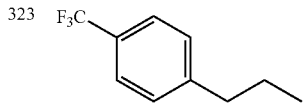 | 472 |
| 324 | 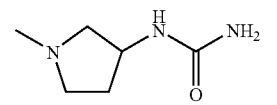 | 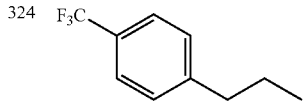 | 507 |
| 325 | 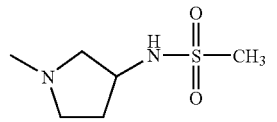 | 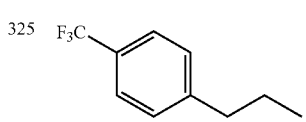 | 529 |
| 326 | 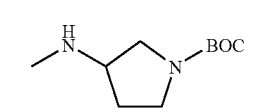 | 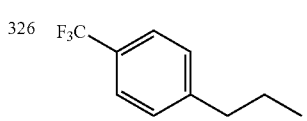 | 429 |
| 327 | 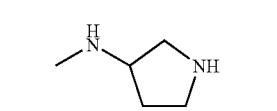 | 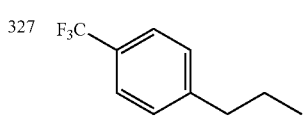 | 486 |
| 328 | 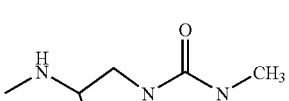 | 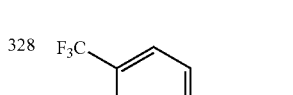 | 525 |
| 329 | 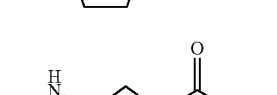 | 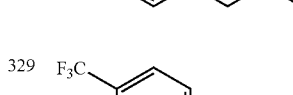 | 471 |
| 330 | 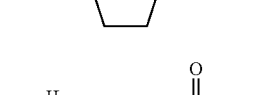 | 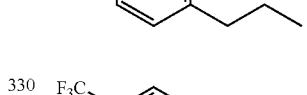 | 459 M-56 |
| 331 | 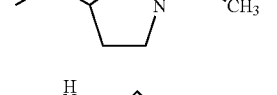 | 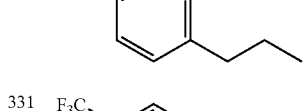 | 415 |
| 332 | 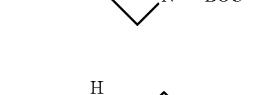 | 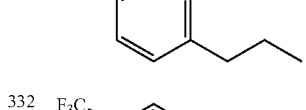 | 485 |

-continued
| Ex. # | R₇ | R = NR₁R₂ | Parent Ion (MH+) m/z |
|---|---|---|---|
| 333 | 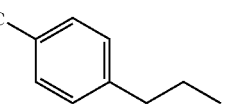 | 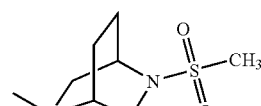 | 533 |
| 334 | 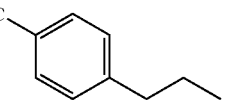 | 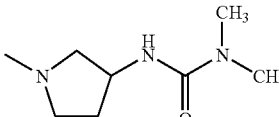 | 500 |
| 335 | 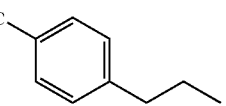 | 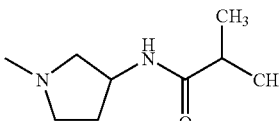 | 499 |
| 336 | 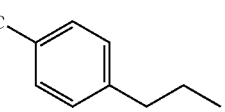 | 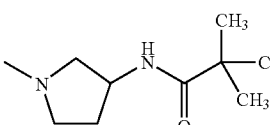 | 513 |
| 337 | 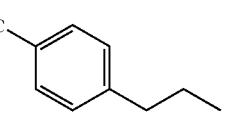 | 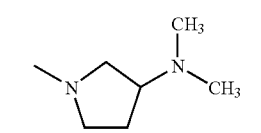 | 457 |
| 338 | 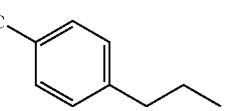 | 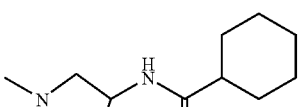 | 540 |
| 339 | 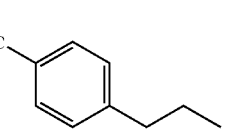 | 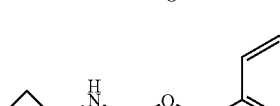 | 549 |
| 340 | 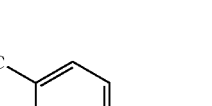 | 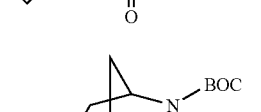 | 541 |
| 341 | 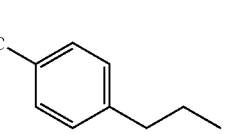 | 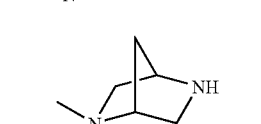 | 441 |
| 342 | 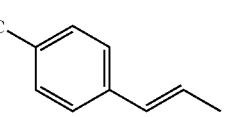 | 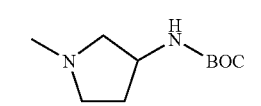 | 527 |

-continued
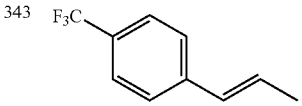
| Ex. # | R7 | R = NR1R2 | Parent Ion (MH+) m/z |
|---|---|---|---|
| 343 | 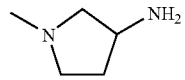 | 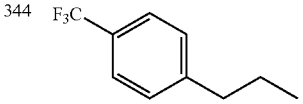 | 427 |
| 344 | 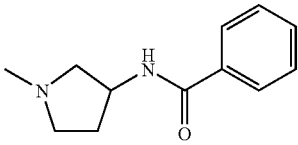 | 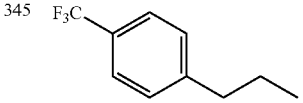 | 533 |
| 345 | 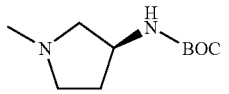 | 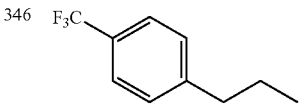 | 529 |
| 346 | 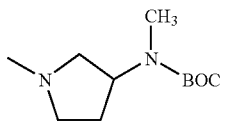 | 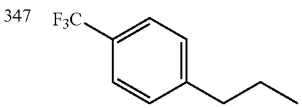 | 543 |
| 347 | 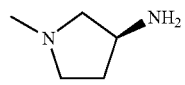 | 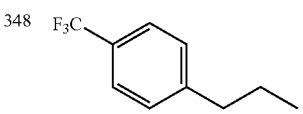 | 427 |
| 348 | 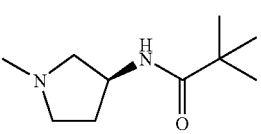 | 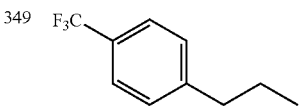 | 513 |
| 349 | 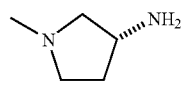 | 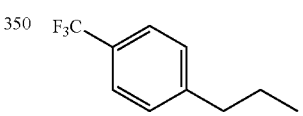 | 427 |
| 350 | 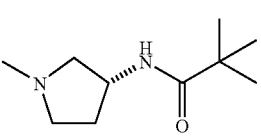 | 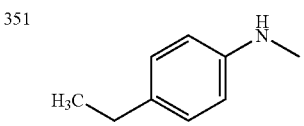 | 513 |
| 351 | 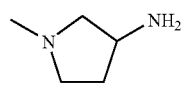 | 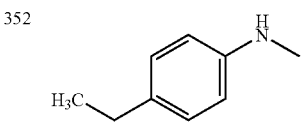 | 376 |
| 352 | 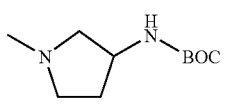 | | 476 |

-continued

| Ex. # | R₇ | R = NR₁R₂ | Parent Ion (MH+) m/z |
|---|---|---|---|
| 353 | 2,2-difluoro-benzodioxole-N(H)-methyl group | N-methyl-(1-methylpyrrolidin-3-yl)-N-methylamine | 456 |
| 354 | 4-(trifluoromethyl)phenethyl | 2-methyl-2,7-diazaspiro[4.4]nonane (N-Me) | 483 |
| 355 | 4-(trifluoromethyl)phenethyl | 2-benzyl-7-methyl-2,7-diazaspiro[4.4]nonane | 559 |
| 356 | 4-(trifluoromethyl)phenethyl | 2-methyl-2,7-diazaspiro[4.4]nonane (N-H) | 469 |

EXAMPLE 357

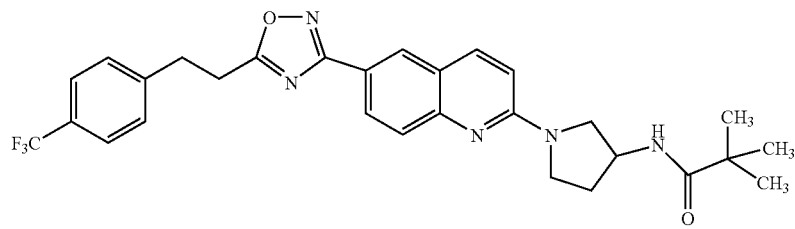

2,2-Dimethyl-N-{1-[6-(5-{2-[4-(trifluoromethyl)phenyl]ethyl}-1,2,4-oxadiazol-3-yl)quinolin-2-yl]pyrrolidin-3-yl}propanamide Step A: 6-Iodo-3,4-dihydroquinolin-2(1H)-one 3,4-Dihydroquinolin-2(1H)-one (7.5 g; 51 mmol) and silver (I) sulfate (17.5 g; 56.1 mmol) were suspended in ethanol (250 mL). A solution of iodine in ethanol (250 mL) was added slowly to the reaction over 1 hour. After 6 hours, the reaction was filtered through CELITE diatomaceous earth and washed copiously with methanol. The volatiles were removed under vacuum and the crude residue was triturated with ether. The solids were collected on a fritted funnel and dried under vacuum. This provided the title compound.

Step B: 2-Oxo-1,2,3,4-tetrahydroquinoline-6-carbonitrile

6-Iodo-3,4-dihydroquinolin-2(1H)-one (1.50 g; 5.50 mmol), sodium cyanide (0.54 g; 11.0 mmol), copper (I) iodide (0.105 g; 0.5 mmol) and tetrakis(triphenylphosphine)palladium(0) (0.32 g; 0.3 mmol) were combined in a flask equipped with a reflux condenser. The flask was subjected to several evacuation-nitrogen purge cycles followed by the addition of acetonitrile (25 mL). The reaction was heated to reflux for 5 hours. After cooling, the reaction was diluted with ethyl acetate (200 mL), filtered through CELITE diatomaceous earth and rinsed with copious amounts of ethyl acetate. The organic solution was washed twice with brine (50 mL), dried over sodium sulfate, filtered through a fritted funnel, and the volatiles were removed under vacuum. The crude residue was crystallized from methanol, which afforded the title compound.

Step C: 2-Chloroquinoline-6-carbonitrile

The crude product was prepared from the product of Step B according to the procedure for Example 1, Step B. This furnished the title compound.

Step D: N-[1-(6-cyanoquinolin-2-yl)pyrrolidin-3-yl]-2,2-dimethylpropanamide

The product was prepared from the product of Step C and 2,2-dimethyl-N-pyrrolidin-3-ylpropanamide according to the procedure for Example 119, Step A. This furnished the title compound MS: m/z 323.

Step E N-(1-{6-[(Hydroxyamino)(imino)methyl]quinolin-2-yl}pyrrolidin-3-yl)-2,2-dimethylpropanamide A mixture of the product of Step D (60 mg; 0.1863 mmol), hydroxyl amine hydrochloride (3 eq.), sodium carbonate (4 eq.) in 1.5 mL water and 2.5 mL ethanol was heated to 90° C. for 6 h. The mixture was diluted with dichloromethane, washed twice with brine, dried over sodium sulfate, filtered through a fritted funnel and the volatiles were removed under vacuum. This provided the product, MS: m/z 356, which was used in the next step without further purification.

Step F: 2,2-Dimethyl-N-{1-[6-(5-{2-[4-(trifluoromethyl)phenyl]ethyl}-1,2,4-oxadiazol-3-yl)quinolin-2-yl]pyrrolidin-3-yl}propanamide To a mixture of the product of Step E, (66 mg) in anhydrous diglyme (2 mL) was added 4-trifluoromethylphenylpropionic acid (1.1 eq.) and EDC (2 eq.). The reaction mixture was heated to 50° C. overnight. After approximately 18 h, the mixture was heated at 110° C. for 2 hr. The mixture was cooled to r.t., quenched with water and extracted with excess EtOAc. The combined extracts were dried over a drying agent filtered and the solvent removed under vacuum. The residue was purified by preparative TLC eluting with EtOAc to afford the product, MS: m/z 538.

Using the appropriate starting materials and following procedures similar to those described above, the following compounds were prepared:

| Ex. # | R⁶ | R | Parent ion (MH+) m/z |
|---|---|---|---|
| 358 | | | 510 |
| 359 | | | 524 |
| 360 | | | 554 |
| 361 | | | 454 |
| 362 | | | 510 |

Biological Assays

MCH-1R and MCH-2R Radioligand Binding Assays

Membrane binding assays were performed on transiently-transfected COS-7 cells expressing human MCH-2R from the plasmid vector pCI-neo (Promega, Madison, Wis.), on a Chinese hamster ovary (CHO) cell line stably expressing the MCH-2R from the plasmid vector pEF1/V5-HisB (Invitrogen, Carlsbad, Calif.), or a CHO cell line stably expressing human MCH-1R from pcDNA3.1. For transient expression, COS-7 cells were cultured in Dulbecco's modified Eagle medium (Gibco BRL, Rockville, Md.) with 10% heat inactivated fetal calf serum. A suspension of $7 \times 10^6$ COS-7 cells were transfected with 20 µg of pCI-neo/MCH-2R plasmid by electroporation and cells were harvested after 60–72 hours. Membranes were prepared from transient and stable transfectants by hypotonic lysis, frozen in liquid nitrogen, and stored at –80° C. A scintillation proximity assay (SPA) was developed to measure the specific binding of $[^{125}I]$-[Phe$^{13}$Tyr$^{19}$]-hMCH. SPA were carried out using wheatgerm agglutinin-polyvinyltoluene beads (Amersham Corp., Arlington Heights, Ill.), in 96-well OptiPlates (Packard, Meriden, Conn.). Each well contained 0.25 mg of SPA beads, 1–10 µg of membrane protein, and 200 µL binding buffer (50 mM Tris pH 7.4, 10 mM $MgCl_2$, 2 mM EDTA, 12% glycerol, 0.1% BSA). Binding buffer contained 50 mM Tris pH 7.4, 8 mM $MgCl_2$, 12% glycerol, 0.1% BSA (Sigma, St. Louis, Mo.) and protease inhibitors: 4 µg/mL of leupeptin (Sigma, St. Louis, Mo.), 40 µg/ML of Bacitracin (Sigma, St. Louis, Mo.), 5 µg/mL of Aprotinin (Roche Molecular Biochem., Indianapolis, Ind.), 0.05M AEBSF (Roche Molecular Biochem., Indianapolis, Ind.), and 5 mM Phosphoramidon (Boeringer Mannheim). Assays were optimized with respect to membrane preparations: for CHO/MCH-1R membranes, 1 µg of membranes per well yielded a >6× specific binding window and for COS or CHO MCH-2R membranes, 8 µg of membrane protein yielded a window of about 3×. Specific binding is defined as the difference between total binding and non-specific binding conducted in the presence of 500 nM unlabeled hMCH. Beads were coated with membranes for 20 minutes and dispensed to the 96 wells, various concentrations of test compounds in DMSO were added (final DMSO concentration 1%–2%), then 25 nCi of $[^{125}I]$-[Phe$^{13}$Tyr$^{19}$]-hMCH (~2000 Ci/mmol; NEN Life Sciences, Boston, Mass.) was added to the wells. After equilibrating at r.t. for 3 hours, the plates were read in a TopCount (Packard, Meriden, Conn.). $IC_{50}$ calculations were performed using Prism 3.0 (GraphPad Software, San Diego, Calif.). The $IC_{50}$ values were measured in three different experiments. A filter-based assay was also used for MCH-2R in 96-well plates. Total volume per binding assay point was 200 µL. Binding conditions were 50 mM Tris pH 7.4, 10 mM $MgCl_2$, 2 mM EDTA 200 µg/mL bacitracin, 1 µM phosphoramidon, 2.5 to 5 µg protein, with and without 10 µM MCH unlabeled peptide as a competitor. Dose response curves were from 10 µM in 5 fold or 3-fold dilution series for 11 points. The mixture was shaken for 5 minutes on a platform shaker, and incubated at r.t. for 1 hour. Filter plates were presoaked in 1% PEI. The binding reaction was harvested onto filters using Packard Filternate harvester (Meriden, Conn.). The filters were then washed in 50 mM Tris pH 7.4, 10 mM $MgCl_2$, 2 mM EDTA, 0.04% Tween 20, 6–8 times per plate. The plates were dried for 20 minutes at 55° C. or overnight at r.t. 30 µL microscintillant was added per well and counted for 1.5–3 minutes in inverted format on Packard TopCount. $IC_{50}$ calculations were performed using Prism 3.0 (GraphPad Software, San Diego, Calif.).

Functional Assay for MCH-1R and MCH-2R

The aequorin bioluminescence assay is a reliable test for identifying G-protein-coupled receptors which couple through the G protein subunit family consisting of $G_q$ and $G_{i}$, which leads to the activation of phospholipase C, mobilization of intracellular calcium, and activation of protein kinase C. Stable cell lines expressing either the MCH-1R or the MCH-2R and the aequorin reporter protein were used. The assay was performed using a Luminoskan RT luminometer (Labsystems Inc., Gaithersburg, Md.) controlled by custom software written for a Macintosh PowerPC 6100. 293AEQ17/MCH-1R(or MCH-2R) cells were cultured for 72 h and the apo-aequorin in the cells was charged for 1 h with coelenterazine (10 µM) under reducing conditions (300 M reduced glutathione) in ECB buffer (140 mM NaCl, 20 mM KCl, 20 mM HEPES-NaOH, pH 7.4, 5 mM glucose, 1 mM $MgCl_2$, 1 mM $CaCl_2$, 0.1 mg/mL bovine serum albumin). The cells were harvested, washed once in ECB medium, and resuspended to 500,000 cells/mL. 100 µL of cell suspension (corresponding to $5 \times 10^4$ cells) was then injected into the test plate containing the test ligands, and the integrated light emission was recorded over 30 s, in 0.5-s units. 20 µL of lysis buffer (0.1% final Triton X-100 concentration) was then injected and the integrated light emission recorded over 10 s, in 0.5-s units. To detect antagonists, test ligands were pre-incubated for ~10 minutes at varying concentrations prior to injection on the test ligand plate containing MCH agonists. The "fractional response" values for each well were calculated by taking the ratio of the integrated response to the initial challenge to the total integrated luminescence including the Triton X-100 lysis response. The functional $EC_{50}$ values were measured in three separate assays.

Selective MCH-1R antagonist compounds of the present invention have $IC_{50}$ affinities for the MCH-1R receptor between 0.1 and 10000 nM, are at least 20× selective for the MCH-1R receptor over the MCH-2R receptor, and are functional antagonists lacking agonist activity at the MCH-1R receptor.

REFERENCES

MCH-1R (Human)
Lakaye et al., "Cloning of the rat brain cDNA encoding for the SLC-1 G protein-coupled receptor reveals the presence of an intron in the gene," Biochim. Biophys Acta; 1401(2):216–20 (1998).
Saito et al., "Molecular characterization of the melanin-concentrating-hormone receptor", Nature; 400(6741):265–9 (1999).
Chambers et al., "Melanin-concentrating hormone is the cognate ligand for the orphan G-protein-coupled receptor SLC-1", Nature; 400(6741): 261–5 (1999).

MCH-2R (human):
Sailer et al., "Identification and characterization of a second melanin-concentrating hormone receptor, MCH-2R", Proc. Natl. Acad. Sci. U S A;98(13):7564–9 (2001).

In Vivo Food Intake Models.
1) Overnight food intake. Sprague Dawley rats are injected intracerebroventricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 hours post compound administration is measured.

2) Food intake in diet induced obese mice. Male C57/B16J mice maintained on a high fat diet (60% fat calories) for 6.5 months from 4 weeks of age are dosed intraperitoneally with test compound. Food intake and body weight are measured over an eight day period. Biochemical parameters relating to obesity, including leptin, insulin, triglyceride, free fatty acid, cholesterol and serum glucose levels are determined.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for obesity, diabetes, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims that follow and that such claims be interpreted as broadly as is reasonable.

What is claimed is:
1. A compound of structural formula (I):

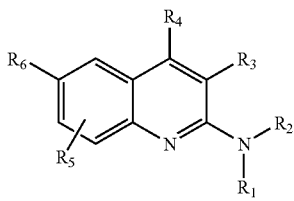

wherein:
$R^1$ and $R^2$ are independently selected from the group consisting of:
(1) hydrogen,
(2) $C_{1-6}$ alkyl,
(3) $C_{2-6}$ alkenyl,
(4) $C_{2-6}$ alkynyl,
(5) cycloalkyl-$C_{0-6}$ alkyl,
(6) heterocycloalkyl-$C_{0-10}$ alkyl,
(7) aryl-$C_{0-10}$ alkyl, and
(8) heteroaryl-$C_{0-10}$ alkyl;
wherein alkyl, alkenyl, and alkynyl, moieties above are optionally substituted with one to four substituents independently selected from $R^a$; and wherein cycloalkyl, heterocycloalkyl aryl and heteroaryl moieties above are optionally substituted with one to four substituents independently selected from $R^b$; and wherein sulfur-containing heterocyclic rings may be mono- or di-oxidized on the sulfur atom;
or, $R^1$ and $R^2$ together with the nitrogen atom to which they are attached, form a 4- to 11-membered bridged or unbridged or spirocyclic heterocyclic ring, optionally containing one or two additional heteroatoms selected from N, S, and O, optionally having one or more degrees of unsaturation, optionally fused to a 6-membered heteroaromatic or aromatic ring, either unsubstituted or substituted with one to four substituents independently selected from $R^b$; and wherein sulfur-containing heterocyclic rings may be mono- or di-oxidized on the sulfur atom;
$R^3$ and $R^4$ are independently selected from the group consisting of:
(1) hydrogen,
(2) halogen,
(3) $C_{1-8}$ alkyl,
(4) perfluoro $C_{1-6}$ alkyl,
(5) $C_{2-6}$ alkenyl,
(6) $C_{2-6}$ alkynyl,
(7) cycloalkyl,
(8) cycloalkyl-$C_{1-6}$ alkyl,
(9) cycloheteroalkyl,
(10) cycloheteroalkyl-$C_{1-6}$ alkyl,
(11) aryl,
(12) aryl-$C_{1-6}$ alkyl,
(13) heteroaryl,
(14) heteroaryl-$C_{1-6}$ alkyl,
(15) —$OR^7$,
(16) —$NR^7R^7$,
(17) —$CO_2R^7$,
(18) cyano, and
(19) —$C(O)NR^7R^7$;
wherein alkyl, alkenyl and alkynyl, moieties above are optionally substituted with one to four substituents independently selected from $R^a$; and wherein cycloalkyl, heterocycloalkyl, aryl and heteroaryl moieties above are optionally substituted with one to four substituents independently selected from $R^b$; and wherein sulfur-containing heterocyclic rings may be mono- or di-oxidized on the sulfur atom;
$R^5$ is
hydrogen
(6);
$R^6$ is selected from the group consisting of:
(1) —$(CH_2)_n$-heteroaryl-$R^7$,
(2) —$(CH_2)_nNR^7C(O)R^7$, and
(3) —$(CH_2)_nN(R^7)_2$, and
wherein one or two of the hydrogen atoms in $(CH_2)_n$ may be substituted with $R^a$;
$R^7$ is independently selected at each occurrence from the group consisting of:
(1) hydrogen,
(2) $C_{1-6}$ alkyl,
(3) aryl,
(4) heteroaryl,
(5) cycloalkyl,
(6) heterocycloalkyl,
(7) aryl $C_{1-3}$ alkyl,
(8) heteroaryl $C_{1-3}$ alkyl,
(9) cycloalkyl $C_{1-3}$ alkyl,
(10) heterocycloalkyl $C_{1-3}$ alkyl,
(11) aryl $C_{2-3}$ alkenyl,
(12) heteroaryl $C_{2-3}$ alkenyl,
(13) cycloalkyl $C_{2-3}$ alkenyl, and
(14) heterocycloalkyl $C_{2-3}$ alkenyl,
wherein the alkyl and alkenyl moieties are optionally substituted with one to four substituents selected from $R^a$; and wherein the aryl, heteroaryl, cycloalkyl and heterocycloalkyl moieties are independently substituted with one to four substituents selected from $R^b$;

and wherein sulfur-containing heterocyclic rings may be mono- or di-oxidized on the sulfur atom;

each $R^a$ is independently selected from:
(1) —$OR^d$,
(2) —$NR^dS(O)_mR^d$,
(3) —$NO_2$,
(4) halogen,
(5) —$S(O)_mR^d$,
(6) —$SR^d$,
(7) —$S(O)_2OR^d$,
(8) —$S(O)_pN(R^d)_2$,
(9) —$N(R^d)_2$,
(10) —$O(CR^dR^d)_nN(R^d)_2$,
(11) —$C(O)R^d$,
(12) —$CO_2R^d$,
(13) —$CO_2(CR^dR^d)_nCON(R^d)_2$,
(14) —$OC(O)R^d$,
(15) —CN,
(16) —$C(O)N(R^d)_2$,
(17) —$NR^dC(O)R^d$,
(18) —$OC(O)N(R^d)_2$,
(19) —$NR^dC(O)OR^d$,
(20) —$NR^dC(O)N(R^d)_2$,
(21) —$CR^d(N—OR^d)$,
(22) —$CF_3$,
(23) cycloalkyl,
(24) cycloheteroalkyl, and
(25) oxo;

each $R^b$ is independently selected from:
(1) $R^a$,
(2) —$Sn(CH_3)_3$,
(3) $C_{1-10}$ alkyl,
(4) $C_{2-10}$ alkenyl,
(5) $C_{2-10}$ alkynyl,
(6) heteroaryl,
(7) aryl, and
(8) aryl-$C_{1-10}$ alkyl;
  wherein alkyl, alkenyl, alkynyl, cycloalkyl, cycloheteroalkyl, heteroaryl, and aryl are optionally substituted with one to four substituents selected from a group independently selected from $R^c$;

each $R^c$ is independently selected from:
(1) halogen,
(2) amino,
(3) carboxy,
(4) $C_{1-4}$ alkyl,
(5) $C_{1-4}$ alkoxy,
(6) aryl,
(7) aryl $C_{1-4}$ alkyl,
(8) hydroxy,
(9) —$CF_3$,
(10) —$OC(O)C_{1-4}$ alkyl,
(11) —$OC(O)N(R^d)_2$, and
(12) aryloxy;

$R^d$ is independently selected from hydrogen, $C_{1-6}$ alkyl, $C_{2-6}$ alkenyl; $C_{2-6}$ alkynyl; cycloalkyl; cycloalkyl-$C_{1-6}$ alkyl; cycloheteroalkyl; cycloheteroalkyl-$C_{1-6}$ alkyl; aryl; heteroaryl; aryl-$C_{1-6}$ alkyl; and heteroaryl-$C_{1-6}$ alkyl;
wherein the alkyl, alkenyl, alkynyl, cycloalkyl, cycloheteroalkyl, heteroaryl, and aryl in $R^d$ are optionally substituted with one to four substituents independently selected from $R^e$;

each $R^e$ is selected from halo, methyl, methoxy, trifluoromethyl, trifluoromethoxy, and hydroxy;

m is selected from 1 and 2;
n is selected from: 0, 1, 2, 3, 4, and 5;
p is selected from 0, 1, and 2;
and pharmaceutically acceptable salts thereof.

2. The compound according to claim 1, wherein:
$R^1$ and $R^2$ are independently selected from the group consisting of:
(1) hydrogen,
(2) $C_{1-6}$ alkyl,
(3) $C_{2-6}$ alkenyl,
(4) cycloalkyl-$C_{0-6}$ alkyl,
(5) heterocycloalkyl-$C_{0-6}$ alkyl,
(6) aryl-$C_{0-6}$ alkyl, and
(7) heteroaryl-$C_{0-10}$ alkyl;
wherein alkyl and alkenyl moieties above are optionally substituted with one to three substituents independently selected from $R^a$; wherein cycloalkyl, heterocycloalkyl, aryl and heteroaryl moieties above are optionally substituted with one to three substituents independently selected from $R^b$;
or, $R^1$ and $R^2$ together with the nitrogen atom to which they are attached, form a 4- to 11-membered bridged or unbridged or spirocyclic heterocyclic ring, optionally containing one additional heteroatom selected from N, S, and O, optionally having one or more degrees of unsaturation, optionally fused to a 6-membered heteroaromatic or aromatic ring, either unsubstituted or substituted with an $R^b$ substituent;

$R^3$ and $R^4$ are independently selected from the group consisting of:
(1) hydrogen,
(2) halogen,
(3) $C_{1-8}$ alkyl,
(4) trifluoromethyl,
(5) $C_{2-6}$ alkenyl,
(6) cycloalkyl,
(7) cycloalkyl-$C_{1-6}$ alkyl,
(8) cycloheteroalkyl,
(9) cycloheteroalkyl-$C_{1-6}$ alkyl,
(10) aryl,
(11) aryl-$C_{1-6}$ alkyl,
(12) heteroaryl,
(13) heteroaryl-$C_{1-6}$ alkyl,
(14) —$OR^7$,
(15) —$NR^7R^7$,
(16) —$CO_2R^7$, and
(17) —$C(O)NR^7R^7$;
wherein alkyl and alkenyl moieties above are optionally substituted with one to four substituents independently selected from $R^a$; and wherein cycloalkyl, heterocycloalkyl, aryl and heteroaryl moieties above are optionally substituted with an $R^b$ substituent;

$R^5$ is
hydrogen
(10);

$R^6$ is selected from the group consisting of:
(1) —$(CH_2)_n$-heteroaryl-$R^7$,
(2) —$(CH_2)_nNR^7C(O)R^7$, and
(3) —$(CH_2)_nN(R^7)_2$,
wherein one or two of the hydrogen atoms in $(CH_2)_n$ may be substituted with $R^a$;

$R^7$ is independently selected at each occurrence from the group consisting of:
(1) hydrogen,
(2) $C_{1-6}$ alkyl,
(3) aryl,
(4) heteroaryl, (5) cycloalkyl,
(6) heterocycloalkyl,
(7) aryl $C_{1-3}$ alkyl,
(8) heteroaryl $C_{1-3}$ alkyl,
(9) cycloalkyl $C_{1-3}$ alkyl,
(10) heterocycloalkyl $C_{1-3}$ alkyl,
(11) aryl $C_{2-3}$ alkenyl,
(12) heteroaryl $C_{2-3}$ alkenyl,
(13) cycloalkyl $C_{2-3}$ alkenyl, and
(14) heterocycloalkyl $C_{2-3}$ alkenyl, wherein the alkyl and alkenyl moieties are optionally substituted with one to four substituents selected from $R^a$; and wherein the aryl, heteroaryl, cycloalkyl and heterocycloalkyl moieties are independently substituted with one to four substituents selected from $R^b$; and wherein sulfur-containing heterocyclic rings may be mono- or di-oxidized on the sulfur atom;

each $R^a$ is independently selected from:
(1) —$OR^d$,
(2) —$NR^d S(O)_m R^d$,
(3) —$NO_2$,
(4) halogen,
(5) —$S(O)_m R^d$,
(6) —$SR^d$,
(7) —$S(O)_2 OR^d$,
(8) —$S(O)_p N(R^d)_2$,
(9) —$N(R^d)_2$,
(10) —$O(CR^d R^d)_n N(R^d)_2$,
(11) —$C(O)R^d$,
(12) —$CO_2 R^d$,
(13) —$CO_2(CR^d R^d)_n CON(R^d)_2$,
(14) —$OC(O)R^d$,
(15) —CN,
(16) —$C(O)N(R^d)_2$,
(17) —$NR^d C(O)R^d$,
(18) —$OC(O)N(R^d)_2$,
(19) —$NR^d C(O)OR^d$,
(20) —$NR^d C(O)N(R^d)_2$,
(21) —$CR^d(N—OR^d)$,
(22) —$CF_3$,
(23) cycloalkyl,
(24) cycloheteroalkyl, and
(25) oxo;

each $R^b$ is independently selected from:
(1) $R^a$,
(2) —$Sn(CH_3)_3$,
(3) $C_{1-10}$ alkyl,
(4) $C_{2-10}$ alkenyl,
(5) heteroaryl,
(6) aryl, and
(7) aryl-$C_{1-10}$ alkyl;
wherein alkyl, alkenyl, cycloalkyl, cycloheteroalkyl, heteroaryl, and aryl are optionally substituted with one to four $R^c$ substituents;

each $R^c$ is independently selected from:
(1) halogen,
(2) amino,
(3) carboxy,
(4) $C_{1-4}$ alkyl,
(5) $C_{1-4}$ alkoxy,
(6) aryl,
(7) aryl $C_{1-4}$ alkyl,
(8) hydroxy,
(9) —$CF_3$,
(10) —$OC(O)C_{1-4}$ alkyl,
(11) —$OC(O)N(R^d)_2$, and
(12) aryloxy;

each $R^d$ is independently selected from hydrogen, $C_{1-6}$ alkyl, $C_{2-6}$ alkenyl; $C_{2-6}$ alkynyl; cycloalkyl; cycloalkyl-$C_{1-6}$ alkyl; cycloheteroalkyl; cycloheteroalkyl-$C_{1-6}$ alkyl; aryl; heteroaryl; aryl-$C_{1-6}$ alkyl; and heteroaryl-$C_{1-6}$ alkyl;
wherein the alkyl, alkenyl, alkynyl, cycloalkyl, cycloheteroalkyl, heteroaryl, and aryl in $R^d$ are optionally substituted with one to two substituents independently selected from a $R^e$;
each $R^e$ is selected from halo, methyl, methoxy, trifluoromethyl, trifluoromethoxy, and hydroxy;
m is selected from 1 and 2;
n is selected from: 0, 1, 2, 3, 4, and 5;
p is selected from 0, 1, and 2;
and pharmaceutically acceptable salts thereof.

3. The compound according to claim 2, wherein:
$R^1$ is selected from the group consisting of:
(1) hydrogen, and
(2) $C_{1-6}$ alkyl, optionally substituted with one to three substituents independently selected from $R^a$;

$R^2$ is selected from the group consisting of:
(1) hydrogen,
(2) $C_{1-6}$ alkyl,
(3) cycloalkyl-$C_{0-6}$ alkyl,
(4) heterocycloalkyl-$C_{0-6}$ alkyl,
(5) aryl-$C_{0-6}$ alkyl, and
(6) heteroaryl-$C_{0-10}$ alkyl;
wherein alkyl moieties above are optionally substituted with one to three substituents independently selected from $R^a$; and wherein cycloalkyl, heterocycloalkyl, aryl and heteroaryl moieties above are optionally substituted with one to three substituents independently selected from $R^b$;
or, $R^1$ and $R^2$ together with the nitrogen atom to which they are attached, form a 4- to 11-membered bridged or unbridged or spirocyclic heterocyclic ring, optionally containing one additional heteroatom selected from N, S, and O, either unsubstituted or substituted with an $R^b$ substituent;

$R^3$ is selected from the group consisting of:
(1) hydrogen,
(2) halogen,
(3) $C_{1-8}$ alkyl,
(4) trifluoromethyl,
(5) —OH,
(6) —$OCH_3$,
(7) —$NH_2$,
(8) —$CO_2 R^7$, and
(9) —$C(O)NH_2$;
wherein alkyl moieties above are optionally substituted with one to two substituents independently selected from $R^a$;

$R^4$ is selected from the group consisting of:
(1) hydrogen,
(2) halogen,
(3) $C_{1-8}$ alkyl,
(4) trifluoromethyl,
(5) cycloalkyl,
(6) cycloheteroalkyl,
(7) aryl,
(8) aryl-$C_{1-6}$ alkyl,
(9) heteroaryl,
(10) —OH,
(11) —OCH,
(12) —$NH_2$,
(13) —$CO_2 R^7$, and
(14) —$C(O)NH_2$;

wherein alkyl moieties above are optionally substituted with one to four substituents independently selected from $R^a$; and wherein cycloalkyl, heterocycloalkyl, aryl and heteroaryl moieties above are optionally substituted with an $R^b$ substituent;

$R^5$ is
hydrogen
(10);

$R^6$ is selected from the group consisting of:
(1) —$(CH_2)_n$-heteroaryl-$R^7$,
(2) —$(CH_2)_n NR^7 C(O)R^7$, and
(3) —$(CH_2)_n N(R^7)_2$,
wherein one or two of the hydrogen atoms in $(CH_2)_n$ may be substituted with $R^a$;

$R^7$ is independently selected at each occurrence from the group consisting of:
(1) hydrogen,
(2) $C_{1-6}$ alkyl,
(3) aryl,
(4) heteroaryl,
(5) cycloalkyl,
(6) heterocycloalkyl,
(7) aryl $C_{1-3}$ alkyl,
(8) heteroaryl $C_{1-3}$ alkyl,
(9) cycloalkyl $C_{1-3}$ alkyl,
(10) heterocycloalkyl $C_{1-3}$ alkyl,
(11) aryl $C_{2-3}$ alkenyl,
(12) heteroaryl $C_{2-3}$ alkenyl,
(13) cycloalkyl $C_{2-3}$ alkenyl, and
(14) heterocycloalkyl $C_{2-3}$ alkenyl,
wherein the alkyl and alkenyl moieties are optionally substituted with one to three substituents selected from $R^a$; and wherein the aryl, heteroaryl, cycloalkyl and heterocycloalkyl moieties are independently substituted with one to three substituents selected from $R^b$; and wherein sulfur-containing heterocyclic rings may be mono- or di-oxidized on the sulfur atom;

each $R^a$ is independently selected from:
(1) —$OR^d$,
(2) —$NR^d S(O)_m R^d$,
(3) —$NO_2$,
(4) halogen,
(5) —$S(O)_m R^d$,
(6) —$SR^d$,
(7) —$S(O)_2 OR^d$,
(8) —$S(O)_p N(R^d)_2$,
(9) —$N(R^d)_2$,
(10) —$O(CR^d R^d)_n N(R^d)_2$,
(11) —$C(O)R^d$,
(12) —$CO_2 R^d$,
(13) —$CO_2(CR^d R^d)_n CON(R^d)_2$,
(14) —$OC(O)R^d$,
(15) —CN,
(16) —$C(O)N(R^d)_2$,
(17) —$NR^d C(O)R^d$,
(18) —$OC(O)N(R^d)_2$,
(19) —$NR^d C(O)OR^d$,
(20) —$NR^d C(O)N(R^d)_2$,
(21) —$CR^d(N-OR^d)$,
(22) —$CF_3$,
(23) cycloalkyl,
(24) cycloheteroalkyl, and
(25) oxo;

each $R^b$ is independently selected from:
(1) $R^a$,
(2) —$Sn(CH_3)_3$,
(3) $C_{1-10}$ alkyl,
(4) $C_{2-10}$ alkenyl,
(5) heteroaryl,
(6) aryl, and
(7) aryl-$C_{1-10}$ alkyl;
wherein alkyl, alkenyl, cycloalkyl, cycloheteroalkyl, heteroaryl, and aryl moieties in $R^a$ and $R^b$ are optionally substituted with one to four $R^c$ substituents;

each $R^c$ is independently selected from:
(1) halogen,
(2) amino,
(3) carboxy,
(4) $C_{1-4}$ alkyl,
(5) $C_{1-4}$ alkoxy,
(6) aryl,
(7) aryl $C_{1-4}$ alkyl,
(8) hydroxy,
(9) —$CF_3$,
(10) —$OC(O)C_{1-4}$ alkyl,
(11) —$OC(O)N(R^d)_2$, and
(12) aryloxy;

$R^d$ is independently selected from hydrogen, $C_{1-6}$ alkyl, $C_{2-6}$ alkenyl; $C_{2-6}$ alkynyl; cycloalkyl; cycloalkyl-$C_{1-6}$ alkyl; cycloheteroalkyl; cycloheteroalkyl-$C_{1-6}$ alkyl; aryl; heteroaryl; aryl-$C_{1-6}$ alkyl; and heteroaryl-$C_{1-6}$ alkyl;
wherein the alkyl, alkenyl, alkynyl, cycloalkyl, cycloheteroalkyl, heteroaryl, and aryl in $R^d$ are optionally substituted with one to two substituents independently selected from a $R^e$;

each $R^e$ is selected from halo, methyl, methoxy, trifluoromethyl, trifluoromethoxy, and hydroxy;

m is selected from 1 and 2;
n is selected from: 0, 1, 2, 3, and 4;
p is selected from 0, 1, and 2;
and pharmaceutically acceptable salts thereof.

4. The compound according to claim 3, wherein:
$R^1$ is selected from the group consisting of:
(1) hydrogen,
(2) methyl,
(3) ethyl, and
(4) propyl,
optionally substituted with one to three substituents independently selected from $R^a$;

$R^2$ is selected from the group consisting of:
(1) hydrogen,
(2) $C_{1-6}$ alkyl,
(3) cycloalkyl-$C_{0-6}$ alkyl,
(4) heterocycloalkyl-$C_{0-6}$ alkyl, and
(5) aryl-$C_{0-6}$ alkyl,
wherein alkyl moieties above are optionally substituted with one to three substituents independently selected from $R^a$; and wherein cycloalkyl, heterocycloalkyl, aryl and heteroaryl moieties above are optionally substituted with one to three substituents independently selected from $R^b$;
or, $R^1$ and $R^2$ together with the nitrogen atom to which they are attached, form a 4- to 11-membered bridged or unbridged or spirocyclic heterocyclic ring, optionally containing one additional heteroatom selected from N, S, and O, either unsubstituted or substituted with an $R^b$ substituent;

$R^3$ is selected from the group consisting of:
(1) hydrogen,
(2) halogen,
(3) $C_{1-8}$ alkyl, and
(4) trifluoromethyl, wherein alkyl moieties above are optionally substituted with one to two substituents independently selected from $R^a$;

$R^4$ is selected from the group consisting of:
(1) hydrogen,
(2) $C_{1-8}$ alkyl,
(3) trifluoromethyl,
(4) cycloalkyl,
(5) cycloheteroalkyl,
(6) aryl,
(7) heteroaryl,
(8) —$NH_2$,
(9) —$CO_2H$,
(10) —$CO_2CH_3$, and
(11) —$CO_2CH_2CH_3$;

wherein alkyl moieties above are optionally substituted with one to two substituents independently selected from $R^a$; and wherein cycloalkyl, heterocycloalkyl, aryl and heteroaryl moieties above are optionally substituted with an $R^b$ substituent;

$R^5$ is
hydrogen
(6);

$R^6$ is selected from the group consisting of:
(1) —$(CH_2)_n$-heteroaryl-$R^7$,
(2) —$(CH_2)_nNR^7C(O)R^7$, and
(3) —$(CH_2)_nN(R^7)_2$, wherein one or two of the hydrogen atoms in $(CH_2)_n$ may be substituted with $R^a$;

$R^7$ is independently selected at each occurrence from the group consisting of:
(1) hydrogen,
(2) $C_{1-6}$ alkyl,
(3) aryl,
(4) heteroaryl,
(5) cycloalkyl,
(6) heterocycloalkyl,
(7) aryl $C_{1-3}$ alkyl,
(8) heteroaryl $C_{1-3}$ alkyl,
(9) cycloalkyl $C_{1-3}$ alkyl,
(10) heterocycloalkyl $C_{1-3}$ alkyl,
(11) aryl $C_{2-3}$ alkenyl,
(12) heteroaryl $C_{2-3}$ alkenyl,
(13) cycloalkyl $C_{2-3}$ alkenyl, and
(14) heterocycloalkyl $C_{2-3}$ alkenyl, wherein the alkyl and alkenyl moieties are optionally substituted with one to three substituents selected from $R^a$; and wherein the aryl, heteroaryl, cycloalkyl and heterocycloalkyl moieties are independently substituted with one to three substituents selected from $R^b$; and wherein sulfur-containing heterocyclic rings may be mono- or di-oxidized on the sulfur atom;

each $R^a$ is independently selected from:
(1) —$OR^d$,
(2) —$NHSO_2CH_3$,
(3) —$NO_2$,
(4) halogen,
(5) —$S(O)_mCH_3$,
(6) —$SR^d$,
(7) —$S(O)_2OR^d$,
(8) —$S(O)_pN(R^d)_2$,
(9) —$N(R^d)_2$,
(10) —$O(CR^dR^d)_nN(R^d)_2$,
(11) —$C(O)R^d$,
(12) —$CO_2R^d$,
(13) —$CO_2(CR^dR^d)_nCON(R^d)_2$,
(14) —$OC(O)R^d$,
(15) —CN,
(16) —$C(O)N(R^d)_2$,
(17) —$NR^dC(O)R^d$,
(18) —$OC(O)N(R^d)_2$,
(19) —$NR^dC(O)OR^d$,
(20) —$NR^dC(O)N(R^d)_2$,
(21) —$CR^d(N—OR^d)$,
(22) —$CF_3$,
(23) cycloalkyl,
(24) cycloheteroalkyl, and
(25) oxo;

each $R^b$ is independently selected from:
(1) $R^a$,
(2) —$Sn(CH_3)_3$,
(3) $C_{1-6}$ alkyl,
(4) $C_{2-6}$ alkenyl,
(5) heteroaryl,
(6) aryl, and
(7) aryl-$C_{1-10}$ alkyl;

wherein alkyl, alkenyl, cycloalkyl, cycloheteroalkyl, heteroaryl, and aryl moieties in $R^a$ and $R^b$ are optionally substituted with one to four $R^c$ substituents;

each $R^c$ is independently selected from:
(1) halogen,
(2) amino,
(3) carboxy,
(4) $C_{1-4}$ alkyl,
(5) $C_{1-4}$ alkoxy,
(6) aryl,
(7) aryl $C_{1-4}$ alkyl,
(8) hydroxy,
(9) —$CF_3$,
(10) —$OC(O)C_{1-4}$ alkyl,
(11) —$OC(O)N(R^d)_2$, and
(12) aryloxy;

$R^d$ is independently selected from hydrogen, $C_{1-6}$ alkyl, $C_{2-6}$ alkenyl; $C_{2-6}$ alkynyl; cycloalkyl; cycloalkyl-$C_{1-6}$ alkyl; cycloheteroalkyl; cycloheteroalkyl-$C_{1-6}$ alkyl; aryl; heteroaryl; aryl-$C_{1-6}$ alkyl; and heteroaryl-$C_{1-6}$ alkyl;

wherein the alkyl, alkenyl, alkynyl, cycloalkyl, cycloheteroalkyl, heteroaryl, and aryl in $R^d$ are optionally substituted with one to two substituents independently selected from a $R^e$;

each $R^e$ is selected from halogen, methyl, methoxy, trifluoromethyl, trifluoromethoxy, and hydroxy;

m is selected from 1 and 2;
n is selected from: 0, 1, 2, 3, and 4;
p is selected from 0, 1, and 2;

and pharmaceutically acceptable salts thereof.

5. The compound according to claim 4, wherein:
$R^1$ is selected from the group consisting of:
(1) hydrogen, and
(2) methyl;
optionally substituted with one to three substituents independently selected from $R^a$;

$R^2$ is selected from the group consisting of:
(1) methyl,
(2) ethyl,
(3) n-propyl,
(4) isopropyl,
(5) t-butyl,
(6) n-butyl,
(7) cyclopropyl,
(8) cyclobutyl,
(9) cyclopentyl,
(10) cyclohexyl,

(11) heterocycloalkyl-$C_{0-6}$ alkyl, wherein the heterocycloalkyl moiety is selected from azetidinyl, pyrrolidinyl, and pyridyl and
(12) phenyl-$C_{0-6}$ alkyl,
wherein alkyl moieties above are optionally substituted with one to three substituents independently selected from $R^a$; and wherein cycloalkyl, heterocycloalkyl, and aryl moieties above are optionally substituted with one to three substituents independently selected from $R^b$;
or, $R^1$ and $R^2$ together with the nitrogen atom to which they are attached, form a 4- to 11-membered heterocyclic ring, selected from: azetidinyl, pyrrolidinyl, piperidinyl, morpholinyl, 1-thia-4-azacyclohexyl, 2,5-diazabicyclo[2.2.2]octanyl, azacycloheptyl, 2-oxa-5-azabicyclo[2.2.1]heptyl, 2,5-diazabicyclo[2.2.1]heptyl, 2-azabicyclo[2.2.1]heptyl, 7-azabicyclo[2.2.1]heptyl, 2,5-diazabicyclo[2.2.2]octyl, 2-azabicyclo[2.2.2]octyl, and 3-azabicyclo[3.2.2]nonyl, 2,7-diazaspiro[4.4]nonyl, 2,7-diazaspiro[4.5]decyl, 2,7-diazaspiro[4.6]undecyl, 1,7-diazaspiro[4.4]nonyl, 2,6-dizaospiro[4.5]decyl, 2,6-diazaspiro[4.6]-undecyl, either unsubstituted or substituted with an $R^b$ substituent;
$R^3$ is selected from the group consisting of:
(1) hydrogen,
(2) halogen,
(3) methyl,
(4) ethyl,
(5) propyl, and
(6) trifluoromethyl,
wherein alkyl moieties above are optionally substituted with one to two substituents independently selected from $R^a$;
$R^4$ is selected from the group consisting of:
(1) hydrogen,
(2) methyl,
(3) ethyl,
(4) propyl,
(5) trifluoromethyl,
(6) —$CO_2H$,
(7) —$CO_2CH_3$ and
(8) —$CO_2CH_2CH_3$;
wherein alkyl moieties above are optionally substituted with one to three substituents independently selected from $R^a$;
$R^5$ is hydrogen;
$R^6$ is selected from the group consisting of:
(1)-heteroaryl-$R^7$,
(2) —$NHC(O)R^7$,
(3) —$NH(R^7)$, and
(4) —$(CH_2)_nNH(R^7)$,
wherein one or two of the hydrogen atoms in $(CH_2)_n$ may be substituted with $R^a$;
$R^7$ is independently selected at each occurrence from the group consisting of:
(1) hydrogen,
(2) $C_{1-6}$ alkyl,
(3) aryl, selected from: phenyl, naphthyl, indanyl, indenyl, indolyl, quinazolinyl, quinolinyl, benzthiazolyl, benzoxazolyl, dihydroindanyl, benzisodiazolyl, spirocyclohexylindolinyl, spiro-(dihydrobenzothiophenyl)piperidinyl, spiro-indolinylpiperidinyl, indolinyl, tetrahydroisoquinolinyl, isoindolinyl, benzothiadiazolyl, benzotriazolyl, 1,3-dihydro-2-benzofuranyl, benzothiophenyl, benzodioxolyl, tetrahydronaphthyl, 2,3-dihydrobenzofuranyl, dihydrobenzopyranyl, and 1,4-benzodioxanyl,
(4) heteroaryl, selected from: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo[2,3-b]pyridyl, quinolyl, indolyl, isoquinolyl, quinazolinyl, benzisodiazolyl, triazolopyrimidinyl, 5,6,7,8-tetrahydroquinolinyl, 2,1,3-benzothiadiazolyl, and thienopyridinyl,
(5) cycloalkyl, selected from: cyclopropyl, cyclobutyl, cyclopentyl, cyclohexyl, cycloheptyl, tetrahydronaphthyl, decahydronaphthyl, indanyl, bicyclo[2.2.2]octanyl, tetrahydronaphthyl, and dihydroindanyl,
(6) heterocycloalkyl, selected from: azetidinyl, pyridyl, pyrrolidinyl, piperidinyl, piperazinyl, imidazolidinyl, morpholinyl, 1-thia-4-aza-cyclohexane, 2,5-diazabicyclo[2.2.2]octanyl, 2,3-dihydrofuro[2,3-b]pyridyl, benzoxazinyl, tetrahydroquinolinyl, tetrahydroisoquinolinyl, dihydroindolyl, indolyl, indolinyl, isoindolinyl, 1,3-dihydro-2-benzofuranyl, benzodioxolyl, hexahydrothienopyridinyl, thienopyridinyl, azacycloheptyl, 4,4-spiro[2,3-dihydrobenzothiophen-3,3-yl]piperidinyl, and 4,4-spiro[indoli-3,3-yl]piperidinyl,
(7) aryl $C_{1-3}$ alkyl, wherein the aryl moiety is selected from: phenyl, naphthyl, indanyl, indenyl, indolyl, quinazolinyl, quinolinyl, benzthiazolyl, benzoxazolyl, dihydroindanyl, benzisodiazolyl, spirocyclohexylindolinyl, spiro-(dihydrobenzothiophenyl)piperidinyl, spiro-indolinylpiperidinyl, indolinyl, tetrahydroisoquinolinyl, isoindolinyl, benzothiadiazolyl, benzotriazolyl, 1,3-dihydro-2-benzofuranyl, benzothiophenyl, benzodioxolyl, tetrahydronaphthyl, 2,3-dihydrobenzofuranyl, dihydrobenzopyranyl, and 1,4-benzodioxanyl,
(8) heteroaryl $C_{1-3}$ alkyl, wherein the heteroaryl moiety is selected: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo[2,3-b]pyridyl, quinolyl, indolyl, isoquinolyl, quinazolinyl, benzisodiazolyl, triazolopyrimidinyl, 5,6,7,8-tetrahydroquinolinyl, 2,1,3-benzothiadiazolyl, and thienopyridinyl,
(9) cycloalkyl $C_{1-3}$ alkyl, wherein the cycloalkyl moiety is selected from: cyclopropyl, cyclobutyl, cyclopentyl, cyclohexyl, cycloheptyl, tetrahydronaphthyl, decahydronaphthyl, indanyl, bicyclo[2.2.2]octanyl, tetrahydronaphthyl, and dihydroindanyl,
(10) heterocycloalkyl $C_{1-3}$ alkyl, wherein the heterocycloalkyl moiety is selected from: azetidinyl, pyridyl, pyrrolidinyl, piperidinyl, piperazinyl, imidazolidinyl, morpholinyl, 1-thia-4-aza-cyclohexane, 2,5-diazabicyclo[2.2.2]octanyl, 2,3-dihydrofuro[2,3-b]pyridyl, benzoxazinyl, tetrahydroquinolinyl, tetrahydroisoquinolinyl, dihydroindolyl, indolyl, indolinyl, isoindolinyl, 1,3-dihydro-2-benzofuranyl, benzodioxolyl, hexahydrothienopyridinyl, thienopyridinyl, azacycloheptyl, 4,4-spiro[2,3-dihydrobenzothiophen-3,3-yl]piperidinyl, and 4,4-spiro[indoli-3,3-yl]piperidinyl,
(11) aryl $C_{2-3}$ alkenyl, wherein the aryl moiety is selected from: phenyl, naphthyl, indanyl, indenyl, indolyl, quinazolinyl, quinolinyl, benzthiazolyl, benzoxazolyl, dihydroindanyl, benzisodiazolyl, spirocyclohexylindolinyl, spiro-(dihydrobenzothiophenyl) piperidinyl, spiro-indolinylpiperidinyl, indolinyl, tetrahydroisoquinolinyl, isoindolinyl, benzothiadiazolyl, benzotriazolyl, 1,3-dihydro-2-benzofuranyl, benzothiophenyl, benzodioxolyl, tetrahydronaphthyl, 2,3-dihydrobenzofuranyl, dihydrobenzopyranyl, and 1,4-benzodioxanyl,

(12) heteroaryl $C_{2-3}$ alkenyl, wherein the heteroaryl moiety is selected from: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo[2,3-b]pyridyl, quinolyl, indolyl, isoquinolyl, quinazolinyl, benzisodiazolyl, triazolopyrimidinyl, 5,6,7,8-tetrahydroquinolinyl, 2,1,3-benzothiadiazolyl, and thienopyridinyl,

(13) cycloalkyl $C_{2-3}$ alkenyl, wherein the cycloalkyl moiety is selected from: cyclopropyl, cyclobutyl, cyclopentyl, cyclohexyl, cycloheptyl, tetrahydronaphthyl, decahydronaphthyl, indanyl, bicyclo[2.2.2]octanyl, tetrahydronaphthyl, and dihydroindanyl, and

(14) heterocycloalkyl $C_{2-3}$ alkenyl, wherein the heterocycloalkyl moiety is selected from: azetidinyl, pyridyl, pyrrolidinyl, piperidinyl, piperazinyl, imidazolidinyl, morpholinyl, 1-thia-4-aza-cyclohexane, 2,5-diazabicyclo[2.2.2]octanyl, 2,3-dihydrofuro[2,3-b]pyridyl, benzoxazinyl, tetrahydroquinolinyl, tetrahydroisoquinolinyl, dihydroindolyl, indolyl, indolinyl, isoindolinyl, 1,3-dihydro-2-benzofuranyl, benzodioxolyl, hexahydrothienopyridinyl, thienopyridinyl, azacycloheptyl, 4,4-spiro[2,3-dihydrobenzothiophen-3,3-yl]piperidinyl, and 4,4-spiro[indoli-3,3-yl]piperidinyl;

wherein the alkyl moieties are optionally substituted with one to three substituents selected from $R^a$; and wherein the aryl, heteroaryl, cycloalkyl and heterocycloalkyl moieties are independently substituted with one to three substituents selected from $R^b$; and wherein sulfur-containing heterocyclic rings may be mono- or di-oxidized on the sulfur atom;

each $R^a$ is independently selected from:
(1) —$OR^d$,
(2) —$NHSO_2CH_3$,
(3) —$NO_2$,
(4) halogen,
(5) —$S(O)_mCH_3$,
(6) —$SCH_3$,
(7) —$SCF_3$,
(8) —$S(O)_2OR^d$,
(9) —$S(O)_pN(R^d)_2$,
(10) —$N(CH_3)_2$,
(11) —$NH_2$,
(12) —$O(CR^dR^d)_nN(R^d)_2$,
(13) —$C(O)R^d$,
(14) —$CO_2H$,
(15) —$CO_2CH_3$,
(16) t-butyloxycarbonyl,
(17) —$CO_2(CR^dR^d)_nCON(R^d)_2$,
(18) —$OC(O)R^d$,
(19) —CN,
(20) —$C(O)N(R^d)_2$,
(21) —$NR^dC(O)R^d$,
(22) —$OC(O)N(R^d)_2$,
(23) —$NR^dC(O)OR^d$,
(24) —$NR^dC(O)N(R^d)_2$,
(25) —$CR^d(N—OR^d)$,
(26) —$CF_3$,
(27) cycloalkyl,
(28) cycloheteroalkyl, and
(29) oxo;

each $R^b$ is independently selected from:
(1) —$R^a$,
(2) —$Sn(CH_3)_3$,
(3) $C_{1-6}$ alkyl,
(4) $C_{2-6}$ alkenyl,
(5) heteroaryl,
(6) aryl, and
(7) aryl-$C_{1-10}$ alkyl;

wherein alkyl, alkenyl, cycloalkyl, cycloheteroalkyl, heteroaryl, and aryl moieties in $R^a$ and $R^b$ are optionally substituted with one to four $R^c$ substituents;

each $R^c$ is independently selected from:
(1) halogen,
(2) amino,
(3) carboxy,
(4) $C_{1-4}$ alkyl,
(5) $C_{1-4}$ alkoxy,
(6) aryl,
(7) aryl $C_{1-4}$ alkyl,
(8) hydroxy,
(9) —$CF_3$,
(10) —$OC(O)C_{1-4}$ alkyl,
(11) —$OC(O)N(R^d)_2$, and
(12) aryloxy;

$R^d$ is independently selected from hydrogen, $C_{1-6}$ alkyl, $C_{2-6}$ alkenyl; $C_{2-6}$ alkynyl; cycloalkyl; cycloalkyl-$C_{1-6}$ alkyl; cycloheteroalkyl; cycloheteroalkyl-$C_{1-6}$ alkyl; aryl; heteroaryl; aryl-$C_{1-6}$ alkyl; and heteroaryl-$C_{1-6}$ alkyl;

wherein the alkyl, alkenyl, alkynyl, cycloalkyl, cycloheteroalkyl, heteroaryl, and aryl in $R^d$ are optionally substituted with one to two substituents independently selected from a $R^e$;

each $R^e$ is selected from halogen, methyl, methoxy, trifluoromethyl, trifluoromethoxy, and hydroxy;

m is selected from 1 and 2;

n is selected from: 0, 1, 2, 3, and 4;

p is selected from 0, 1, and 2;

and pharmaceutically acceptable salts thereof.

6. The compound according to claim 1 of structural formula:

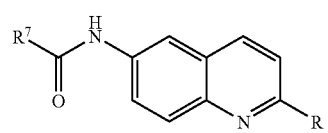

wherein: $R^7$ and R are as illustrated in the table below:

| Ex. # | R⁷ | R = NR¹R² |
|---|---|---|
| 1 | 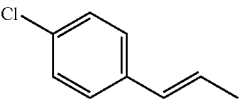 | 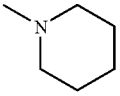 |
| 2 | 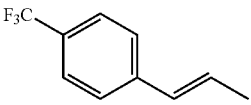 | 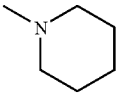 |
| 3 | 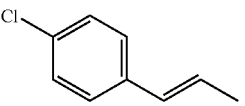 | 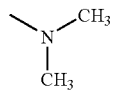 |
| 4 | 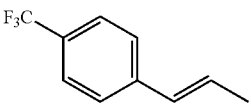 | 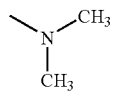 |
| 5 | 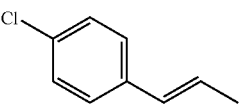 | 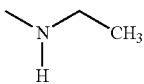 |
| 6 | 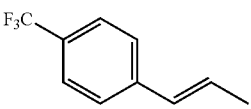 | 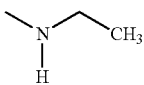 |
| 7 | 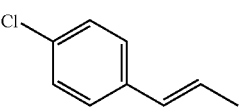 | 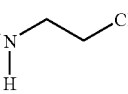 |
| 8 | 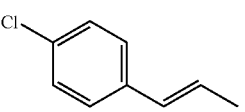 | 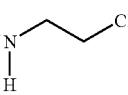 |
| 9 | 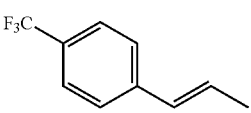 | 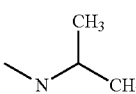 |
| 10 | 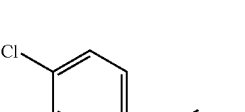 | 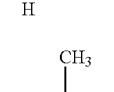 |
| 11 | 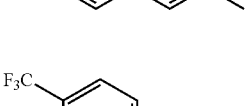 | 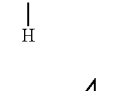 |
| 12 | 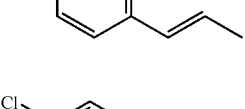 | 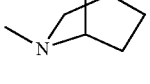 |

-continued
| Ex. # | R⁷ | R = NR¹R² |
|---|---|---|
| 13 | 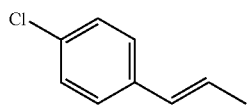 | 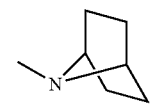 |
| 14 | 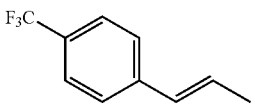 | 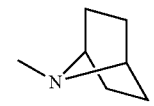 |
| 15 | 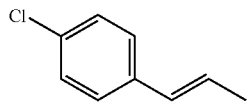 | 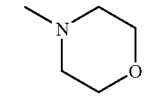 |
| 16 | 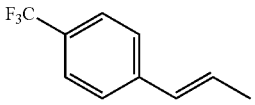 | 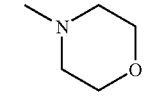 |
| 17 | 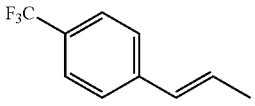 | 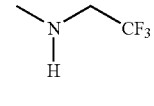 |
| 18 | 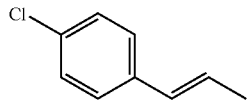 | 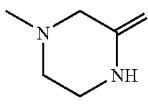 |
| 19 | 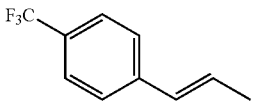 | 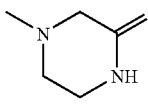 |
| 20 | 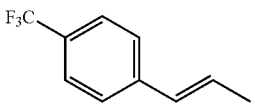 | 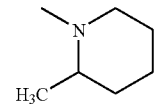 |
| 21 | 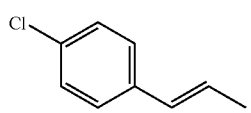 | 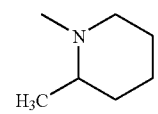 |
| 22 | 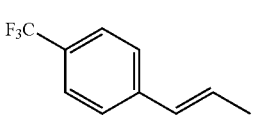 | 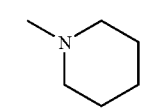 |
| 23 | 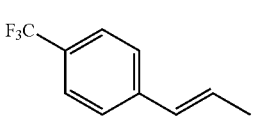 | 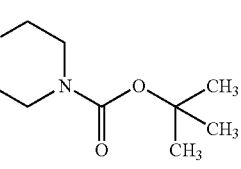 |
| 24 | 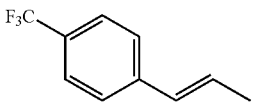 | 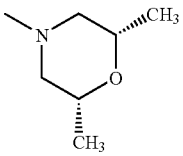 |

-continued

| Ex. # | R⁷ | R = NR¹R² |
|---|---|---|
| 25 | 4-(F₃C)C₆H₄-CH=CH-CH₃ | 4-methylpiperazin-1-yl (NH) |
| 26 | 4-(F₃C)C₆H₄-CH=CH-CH₃ | (3R,5S)-1,3,5-trimethylpiperidin-1-yl |
| 27 | 4-(F₃C)C₆H₄-CH=CH-CH₃ | thiomorpholin-4-yl (N-methyl) |
| 28 | 4-(F₃C)C₆H₄-CH=CH-CH₃ | 1-methylthiomorpholin-4-yl S-oxide |
| 29 | 4-(F₃C)C₆H₄-CH₂CH₂CH₃ | 1,3-dimethylpiperidin-1-yl |
| 30 | 4-(F₃C)C₆H₄-CH=CH-CH₃ | 1,3-dimethylpiperidin-1-yl |
| 31 | 4-(F₃C)C₆H₄-CH₂CH₂CH₃ | 1,4-dimethylpiperidin-1-yl |
| 32 | 4-(F₃C)C₆H₄-CH=CH-CH₃ | 1,4-dimethylpiperidin-1-yl |
| 33 | 4-(F₃C)C₆H₄-CH₂CH₂CH₃ | 1-methylpyrrolidin-1-yl |
| 34 | 4-(F₃C)C₆H₄-CH=CH-CH₃ | 1-methylazepan-1-yl |
| 35 | 4-(F₃C)C₆H₄-CH₂CH₂CH₃ | 1-methylazepan-1-yl |
| 36 | 4-(F₃C)C₆H₄-CH=CH-CH₃ | 1-methylpyrrolidin-1-yl |

-continued
| Ex. # | R[7] | R = NR[1]R[2] |
|---|---|---|
| 37 | 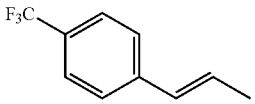 | 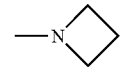 |
| 38 | 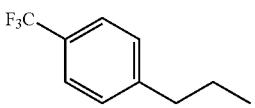 | 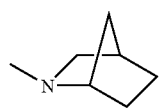 |
| 39 | 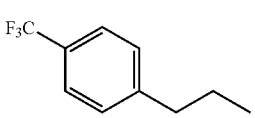 | 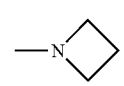 |
| 40 | 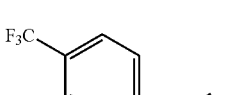 | 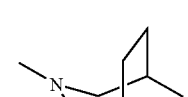 |
| 41 | 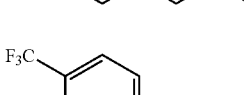 |  |
| 42 | 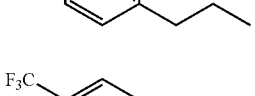 | 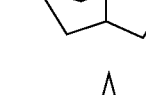 |
| 43 | 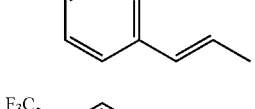 | 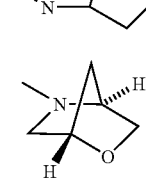 |
| 44 | 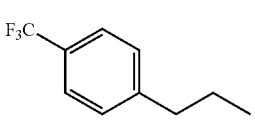 | 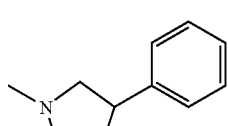 |
| 45 | 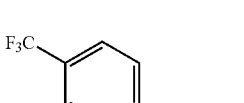 | 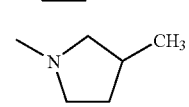 |
| 46 | 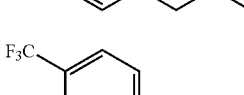 | 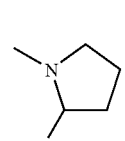 |
| 47 | 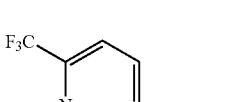 | 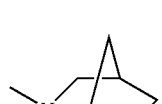 |
| 48 | 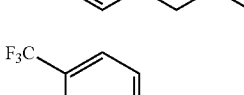 | 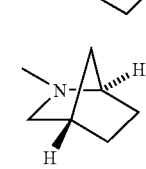 |

-continued

| Ex. # | R⁷ | R = NR¹R² |
|---|---|---|
| 49 | 5-propyl-2-(trifluoromethyl)pyridine | (1S,4S)-2-methyl-2-azabicyclo[2.2.1] |
| 50 | 4-(trifluoromethyl)phenylpropyl | N,N-dimethylamine |
| 51 | 4-(trifluoromethyl)phenyl-propenyl | N-methyl-N-propylamine |
| 52 | 4-(trifluoromethyl)phenylpropyl | N-methyl-N-propylamine |
| 53 | 4-(trifluoromethyl)phenyl-propenyl | N-methyl-N-isobutylamine |
| 54 | 4-(trifluoromethyl)phenylpropyl | N-methyl-N-isobutylamine |
| 55 | 4-(trifluoromethyl)phenyl-propenyl | N-methyl-N-sec-butylamine |
| 56 | 4-(trifluoromethyl)phenylpropyl | N-methyl-N-sec-butylamine |
| 57 | 4-(trifluoromethyl)phenylpropyl | N-methyl-N-tert-butylamine |
| 58 | 4-(trifluoromethyl)phenylpropyl | N-methyl-N-cyclobutylamine |
| 59 | 4-(trifluoromethyl)phenylpropyl | N-methyl-N-(2-methoxyethyl)amine |
| 60 | 4-(trifluoromethyl)phenylpropyl | N-methyl-N-cyclopropylamine |

-continued
| Ex. # | R⁷ | R = NR¹R² |
|---|---|---|
| 61 | 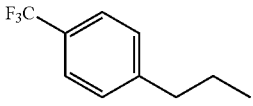 | 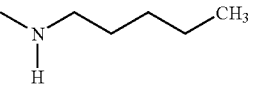 |
| 62 | 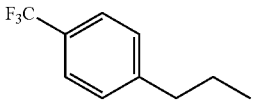 | 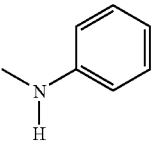 |
| 63 | 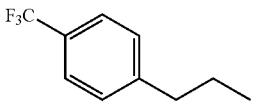 | 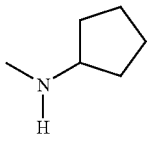 |
| 64 | 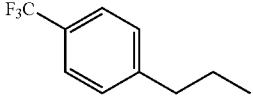 | 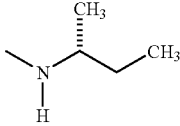 |
| 65 | 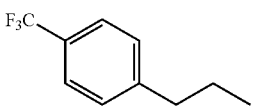 | 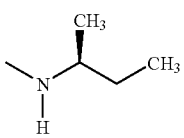 |
| 66 | 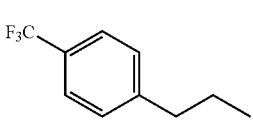 | 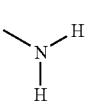 |
| 67 | 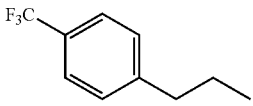 | 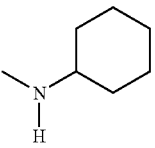 |
| 68 | 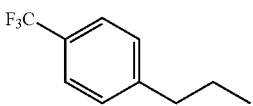 | 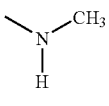 |
| 69 | 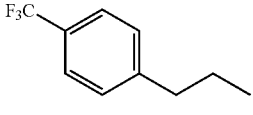 | 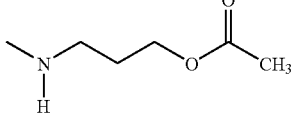 |
| 70 | 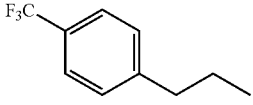 | 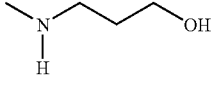 |
| 71 | 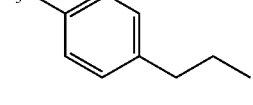 | 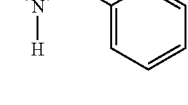 |

-continued
| Ex. # | R⁷ | R = NR¹R² |
|---|---|---|
| 72 | 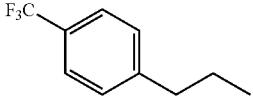 | 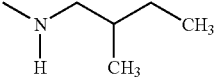 |
| 73 | 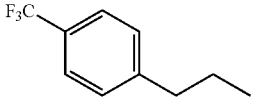 | 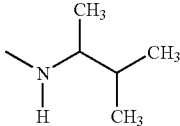 |
| 74 | 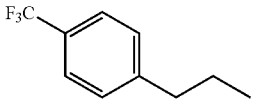 | 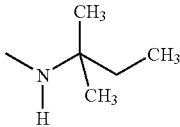 |
| 75 | 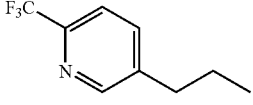 | 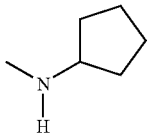 |
| 76 | 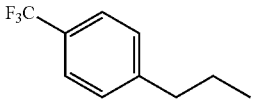 | 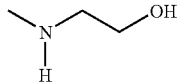 |
| 77 | 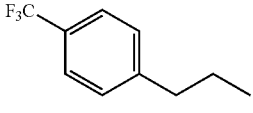 | 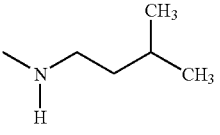 |
| 78 | 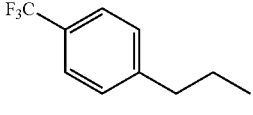 | 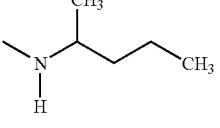 |
| 79 | 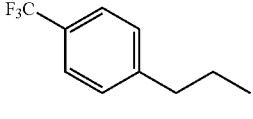 | 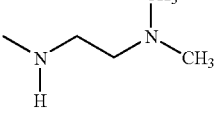 |
| 80 | 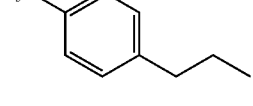 | 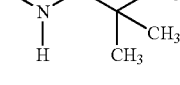 |
| 81 | 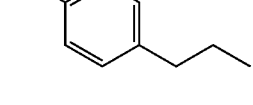 | 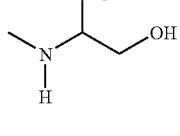 |
| 82 | 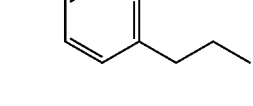 | 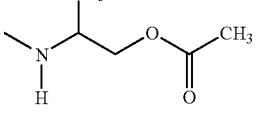 |

| Ex. # | R⁷ | R = NR¹R² |
|---|---|---|
| 83 | 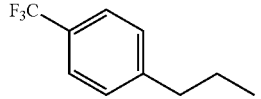 | 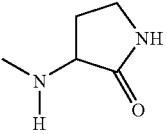 |
| 84 | 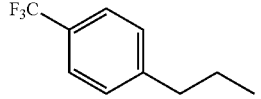 | 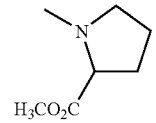 |
| 85 | 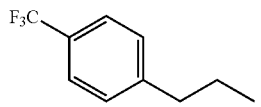 | 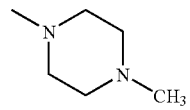 |
| 86 | 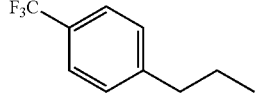 | 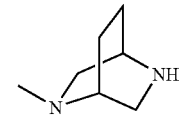 |
| 87 | 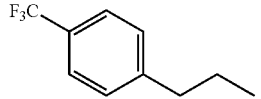 | 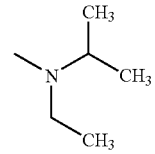 |
| 88 | 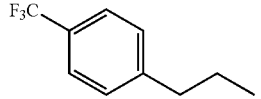 | 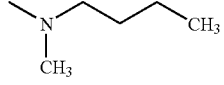 |
| 89 | 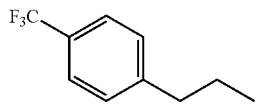 | 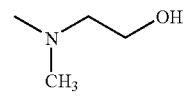 |
| 90 | 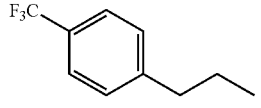 | 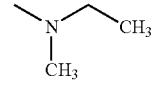 |
| 91 | 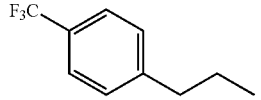 | 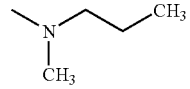 |
| 92 | 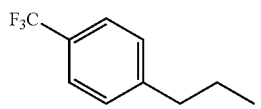 | 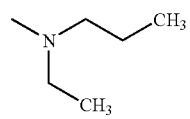 |
| 93 | 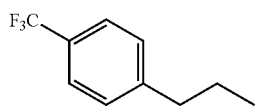 | 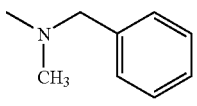 |

-continued

| Ex. # | R⁷ | R = NR¹R² |
|---|---|---|
| 94 | 4-(CF₃)-C₆H₄-CH₂CH₂CH₂- | -N(CH₃)-CH₂CH₂-C₆H₅ |
| 95 | 4-(CF₃)-C₆H₄-CH₂CH₂CH₂- | -N(CH₃)-CH₂CH₂CH₂-C₆H₅ |
| 96 | 4-(CF₃)-C₆H₄-CH₂CH₂CH₂- | -N(CH₃)-cyclopentyl |
| 97 | 4-(CF₃)-C₆H₄-CH₂CH₂CH₂- | 1-methyl-3-benzylpiperidine |
| 98 | 4-(CF₃)-C₆H₄-CH₂CH₂CH₂- | -N(CH₃)-cyclobutyl |
| 99 | 4-(CF₃)-C₆H₄-CH₂CH₂CH₂- | -N(CH₃)-CH(CH₃)-CH₂-O-C(=O)-CH₃ |
| 100 | 4-(CF₃)-C₆H₄-CH₂CH₂CH₂- | -N(CH₃)-CH₂-CH(CH₃)₂ |
| 101 | 4-(CF₃)-C₆H₄-CH₂CH₂CH₂- | -N(CH₃)-CH₂CH₂-CH(CH₃)₂ |
| 102 | 4-(CF₃)-C₆H₄-CH₂CH₂CH₂- | -N(CH₃)-CH(CH₃)-CH₂CH₃ |
| 103 | 4-(CF₃)-C₆H₄-CH₂CH₂CH₂- | -N(CH₃)(CH₂CH₃)(CH₂CH₃) or -N(CH₃)-CH₂CH₃... with ethyl |
| 104 | 4-(CF₃)-C₆H₄-CH₂CH₂CH₂- | -N(CH₃)-(CH₂CH₂CH₃)(CH₂CH₂CH₃) |

-continued
| Ex. # | R⁷ | R = NR¹R² |
|---|---|---|
| 105 | 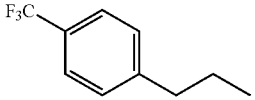 | 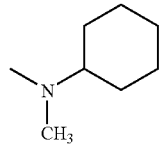 |
| 106 | 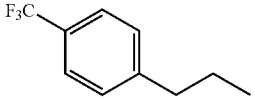 | 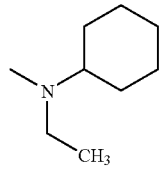 |
| 107 | 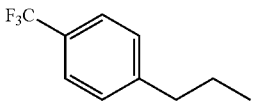 | 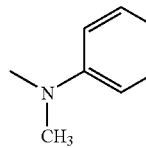 |
| 108 | 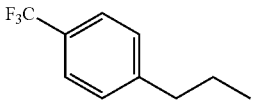 | 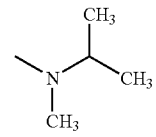 |
| 109 | 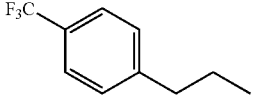 | 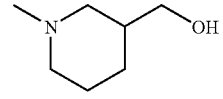 |
| 110 | 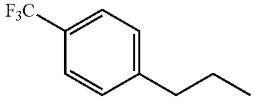 | 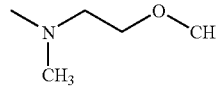 |
| 111 | 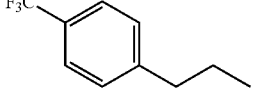 | 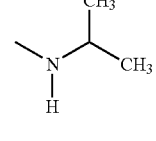 |
| 112 | 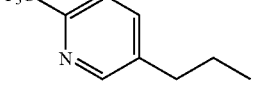 | 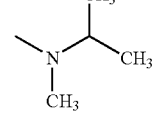 |
| 113 | 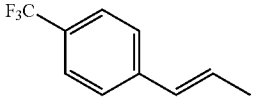 | 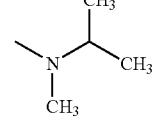 |
| 114 | 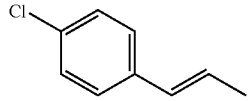 | 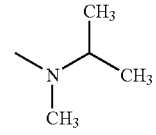 |

-continued

| Ex. # | R⁷ | R = NR¹R² |
|---|---|---|
| 115 | 4-(CF₃)-C₆H₄-CH₂CH₂CH₂- | -N(CH₃)-CH₂CH₂CH₂-(4-pyridyl) |
| 116 | 4-(CF₃)-C₆H₄-CH₂CH₂CH₂- | -N(CH₃)-CH₂CH₂CH₂-(3-pyridyl) |
| 117 | 4-(CF₃)-C₆H₄-CH₂CH₂CH₂- | -NH-C(CH₃)₂-CH₂-O-C(O)CH₃ |
| 118 | 4-(CF₃)-C₆H₄-CH₂CH₂CH₂- | -NH-CH₂-C(CH₃)₂-CH₂-O-C(O)CH₃ |
| 119 | 6-(CF₃)-pyridin-3-yl-CH₂CH₂CH₂- | N-methyl-quinuclidinyl |
| 120 | 4-(CH₃OC(O))-C₆H₄-CH=CH-CH₂- | N-methyl-quinuclidinyl |
| 121 | 4-(CH₃OC(O))-C₆H₄-CH₂CH₂CH₂- | N-methyl-quinuclidinyl |
| 122 | 4-phenyl-1-methyl-bicyclo[2.2.2]octyl | N-methyl-quinuclidinyl |
| 123 | 4'-(CF₃)-biphenyl-4-yl-CH₂- | N-methyl-quinuclidinyl |
| 124 | 4-(CF₃)-C₆H₄-CH₂CH₂CH₂- | N-methyl-quinuclidinyl |

-continued
| Ex. # | R⁷ | R = NR¹R² |
|---|---|---|
| 125 | 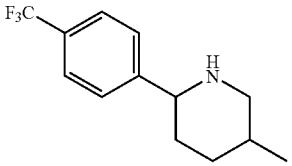 | 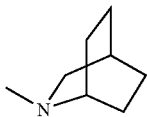 |
| 126 | 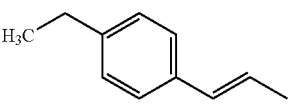 | 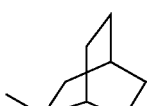 |
| 127 | 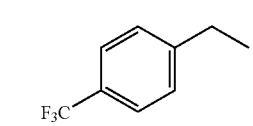 | 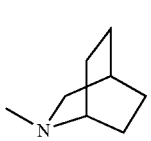 |
| 128 | 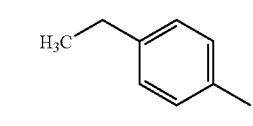 | 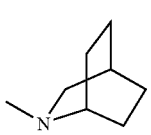 |
| 129 | 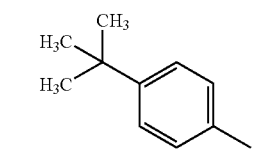 | 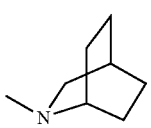 |
| 130 | 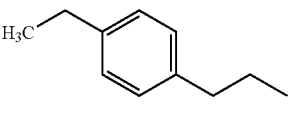 | 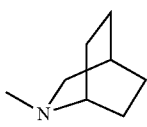 |
| 131 | 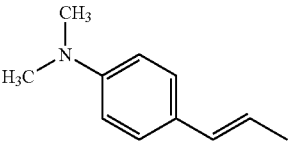 | 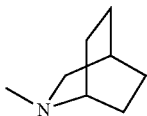 |
| 132 | 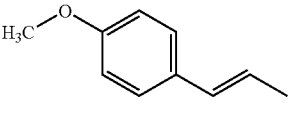 | 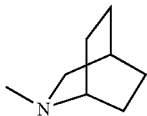 |
| 133 | 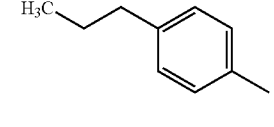 | 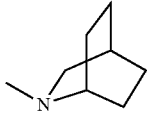 |
| 134 | 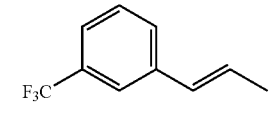 | 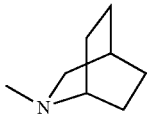 |
| 135 | 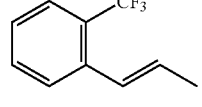 | 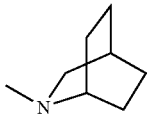 |

-continued
| Ex. # | R[7] | R = NR[1]R[2] |
|---|---|---|
| 136 | 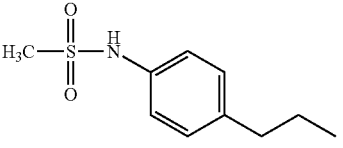 | 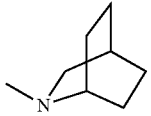 |
| 137 | 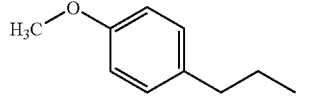 | 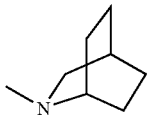 |
| 138 | 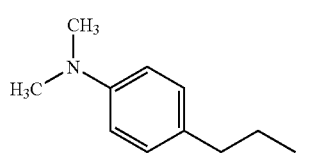 | 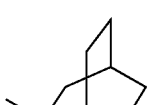 |
| 139 | 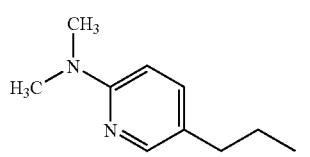 | 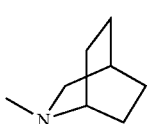 |
| 140 | 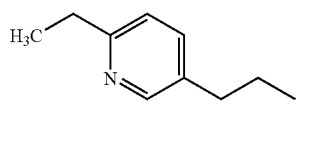 | 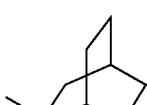 |
| 141 | 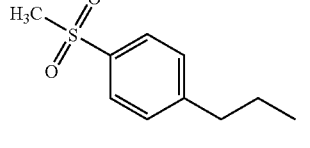 | 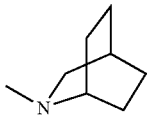 |
| 142 | 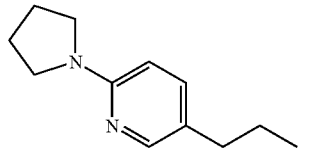 | 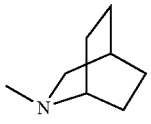 |
| 143 | 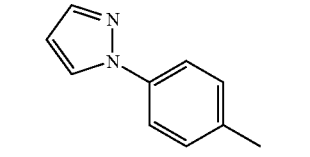 | 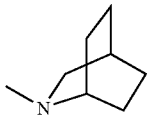 |
| 144 | 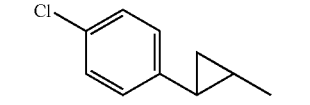 | 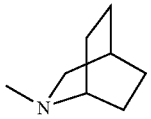 |
| 145 | 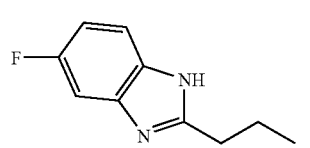 | 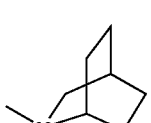 |

-continued

| Ex. # | R⁷ | R = NR¹R² |
|---|---|---|
| 146 | 5-(4-methoxyphenyl)-2-methylfuran | N-methylquinuclidine-like bicyclic amine |
| 147 | 2-propylbenzothiazole | N-methyl bicyclic amine |
| 148 | 1-(4-methylphenyl)piperidine | N-methyl bicyclic amine |
| 149 | 4-(methylthio)-β-methylstyrene | N-methyl bicyclic amine |
| 150 | 1-methyl-4-(4-methylphenyl)piperazine | N-methyl bicyclic amine |
| 151 | 2-(4-methylphenyl)furan | N-methyl bicyclic amine |
| 152 | 2-(ethylthio)benzoxazole | N-methyl bicyclic amine |
| 153 | 5-chloro-2-ethyl-1H-benzimidazole | N-methyl bicyclic amine |
| 154 | 2-(ethylthio)-4-methylthiazole | N-methyl bicyclic amine |

-continued

| Ex. # | R⁷ | R = NR¹R² |
|---|---|---|
| 155 | 3-isobutyl-5-methyl-1H-pyrazole | N-methyl-azabicyclo[2.2.1]heptane |
| 156 | 3-methyl-1-propyl-pyrazole | N-methyl-azabicyclo[2.2.1]heptane |
| 157 | 5-methyl-3-(prop-1-enyl)-isoxazole | N-methyl-azabicyclo[2.2.1]heptane |
| 158 | 4-(methylsulfonyl)propylbenzene | N-methyl-azabicyclo[2.2.1]heptane |
| 159 | 2-propyl-benzothiazole | N-methyl-azabicyclo[2.2.1]heptane |
| 160 | 4-(methylsulfonyl)propylbenzene | N,N-dimethyl-isopropylamine |
| 161 | 2-propyl-benzothiazole | N,N-dimethyl-isopropylamine |
| 162 | 4-(trifluoromethylthio)-N-methyl-aniline | N-methyl-azabicyclo[2.2.1]heptane |
| 163 | 4-phenoxy-N-methyl-aniline | N-methyl-azabicyclo[2.2.1]heptane |
| 164 | N-methyl-naphthalen-2-amine | N-methyl-azabicyclo[2.2.1]heptane |

-continued

| Ex. # | R⁷ | R = NR¹R² |
|---|---|---|
| 165 | 3,4-dimethylphenyl-cyclohexyl-NH(CH₃) | N-methyl-azabicyclo[2.2.2] |
| 166 | 4-phenyl-cyclohexyl-NH(CH₃) | N-methyl-azabicyclo[2.2.2] |
| 167 | 4-(trifluoromethoxy)phenyl-NH(CH₃) | N-methyl-azabicyclo[2.2.2] |
| 168 | 6-(dimethylamino)pyridin-3-yl-NH(CH₃) | N-methyl-azabicyclo[2.2.2] |
| 169 | 4-(phenylamino)phenyl-NH(CH₃) | N-methyl-azabicyclo[2.2.2] |
| 170 | 4-nitrophenyl-NH(CH₃) | N-methyl-azabicyclo[2.2.2] |
| 171 | 4-isopropylphenyl-NH(CH₃) | N-methyl-azabicyclo[2.2.2] |
| 172 | phenyl-NH(CH₃) | N-methyl-azabicyclo[2.2.2] |
| 173 | 4-(trifluoromethyl)phenyl-NH(CH₃) | N-methyl-azabicyclo[2.2.2] |
| 174 | 6-(trifluoromethyl)pyridin-3-yl-NH(CH₃) | N-methyl-azabicyclo[2.2.2] |

-continued
| Ex. # | R⁷ | R = NR¹R² |
|---|---|---|
| 175 |  |  |
| 176 |  |  |
| 177 |  |  |
| 178 |  |  |
| 179 |  |  |
| 180 |  |  |
| 181 |  |  |
| 182 |  |  |
| 183 |  |  |
| 184 |  |  |

-continued
| Ex. # | R⁷ | R = NR¹R² |
|---|---|---|
| 185 | 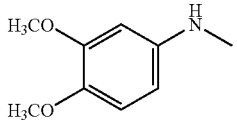 | 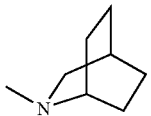 |
| 186 | 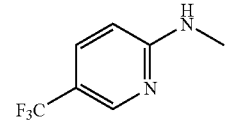 | 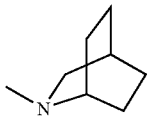 |
| 185 | 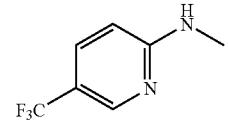 | 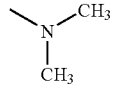 |
| 186 | 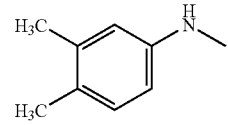 | 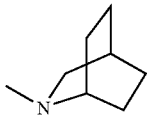 |
| 187 | 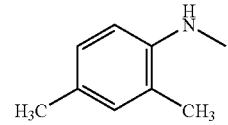 | 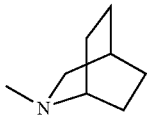 |
| 188 | 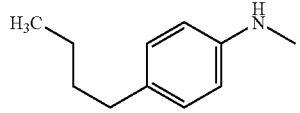 | 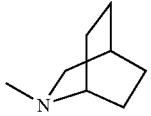 |
| 189 | 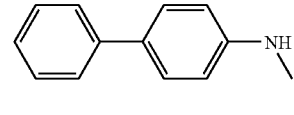 | 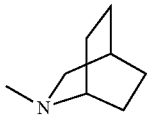 |
| 190 | 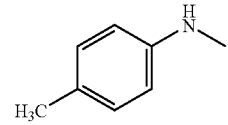 | 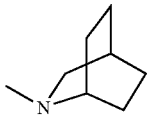 |
| 191 | 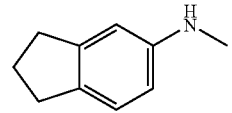 | 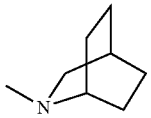 |
| 192 | 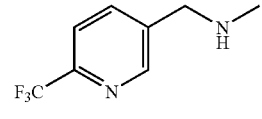 | 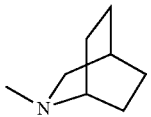 |
| 193 | 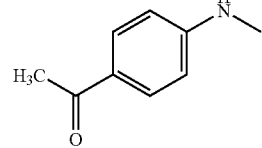 | 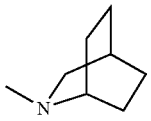 |

-continued
| Ex. # | R⁷ | R = NR¹R² |
|---|---|---|
| 194 | 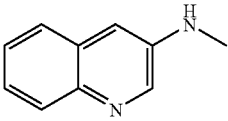 | 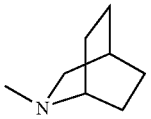 |
| 195 | 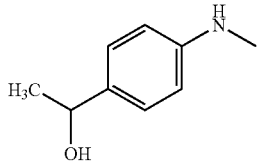 | 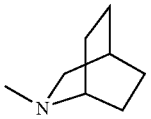 |
| 196 | 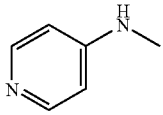 | 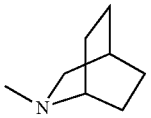 |
| 197 | 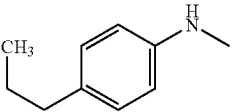 | 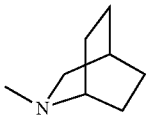 |
| 198 | 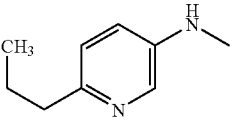 | 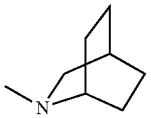 |
| 199 | 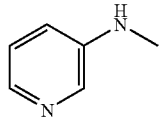 | 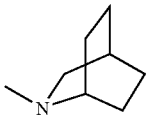 |
| 200 | 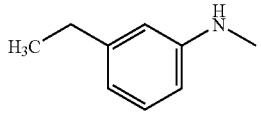 | 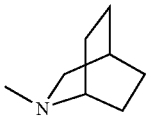 |
| 201 | 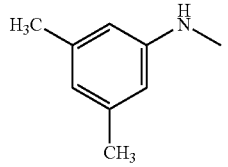 | 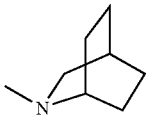 |
| 202 | 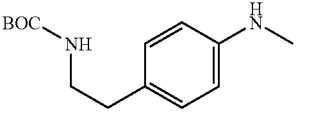 | 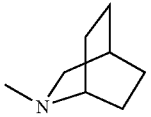 |
| 203 | 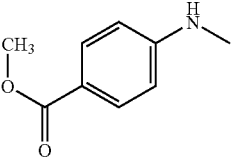 | 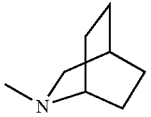 |

-continued

| Ex. # | R⁷ | R = NR¹R² |
|---|---|---|
| 204 | 4-(2-aminoethyl)-N-methylaniline | 1-methyl-1-azabicyclo[2.2.2] (quinuclidine-like) |
| 205 | 4-(methylamino)-N,N-dimethylbenzamide | same |
| 206 | N',N'-dimethyl-N-methyl-benzene-1,4-diamine ethyl | same |
| 207 | 6-ethyl-N-methylpyridin-3-amine | same |
| 208 | 4-(methylamino)benzonitrile | same |
| 209 | N',N'-dimethyl-N-methylbenzene-1,4-diamine | same |
| 210 | N,N,4-trimethyl-aniline with CH₃ | same |
| 211 | 4-cyclohexyl-N-methylaniline | same |
| 212 | N-methyl-5,6,7,8-tetrahydronaphthalen-1-amine | same |
| 213 | N-methyl-5,6,7,8-tetrahydronaphthalen-2-amine | same |

-continued
| Ex. # | R⁷ | R = NR¹R² |
|---|---|---|
| 214 | 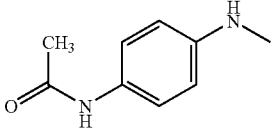 | 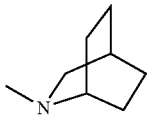 |
| 215 | 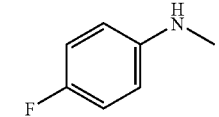 | 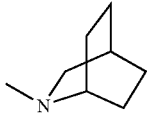 |
| 216 | 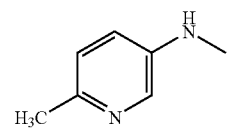 | 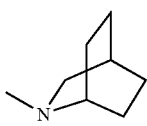 |
| 217 | 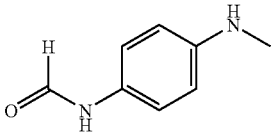 | 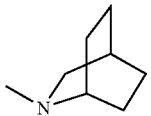 |
| 218 | 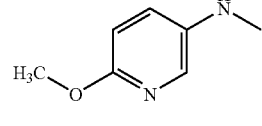 | 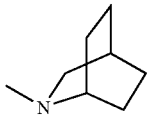 |
| 219 | 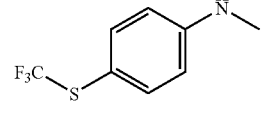 | 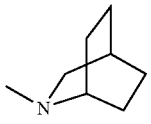 |
| 220 | 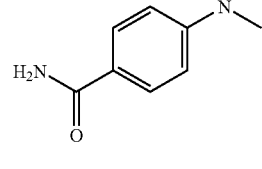 | 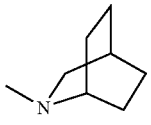 |
| 221 | 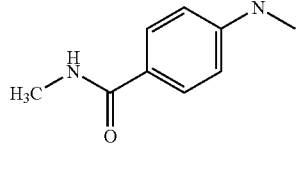 | 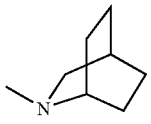 |
| 222 | 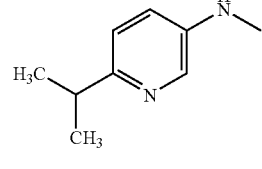 | 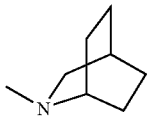 |
| 223 | 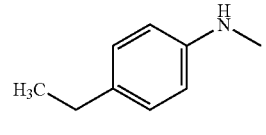 | 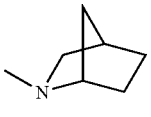 |

-continued

| Ex. # | R⁷ | R = NR¹R² |
|---|---|---|
| 224 | 4-(CH₃NH)-C₆H₃-S-CF₃ | 2-methyl-2-azabicyclo[2.2.1]heptane |
| 225 | 4-(CH₃NH)-C₆H₃-S-CH₃ | 2-methyl-2-azabicyclo[2.2.1]heptane |
| 226 | 4-(CH₃NH)-C₆H₃-O-CF₃ | 2-methyl-2-azabicyclo[2.2.1]heptane |
| 227 | 3-(CH₃NH)-5,6,7,8-tetrahydroquinoline | 2-methyl-2-azabicyclo[2.2.2]octane |
| 228 | 5-(CH₃NH)-2-isopropylpyridine | 2-methyl-2-azabicyclo[2.2.1]heptane |
| 229 | 4-(CH₃NH)-C₆H₃-O-CH₃ | 2-methyl-2-azabicyclo[2.2.1]heptane |
| 230 | 4-(CH₃NH)-C₆H₃-COOH | 2-methyl-2-azabicyclo[2.2.2]octane |
| 231 | 4-(CH₃NH)-C₆H₃-C(O)-pyrrolidinyl | 2-methyl-2-azabicyclo[2.2.2]octane |
| 232 | 4-(CH₃NH)-C₆H₃-C(O)-morpholinyl | 2-methyl-2-azabicyclo[2.2.2]octane |
| 233 | 5-(CH₃NH)-2-(CF₃)-pyrimidine | 2-methyl-2-azabicyclo[2.2.2]octane |

-continued

| Ex. # | R⁷ | R = NR¹R² |
|---|---|---|
| 234 | 5-(methylamino)-2-methoxypyridine | 2-methyl-2-azabicyclo[2.2.1]heptane |
| 235 | 5-(methylamino)-2-(trifluoromethyl)pyridine | 2-methyl-2-azabicyclo[2.2.1]heptane |
| 236 | 2-(3-methylureido)-5-(methylamino)pyridine | 2-methyl-2-azabicyclo[2.2.2]octane |
| 237 | 2-(3-methyl-2-oxoimidazolidin-1-yl)-5-(methylamino)pyridine | 2-methyl-2-azabicyclo[2.2.2]octane |
| 238 | 1-ethyl-5-(methylamino)pyrazole | 2-methyl-2-azabicyclo[2.2.2]octane |
| 239 | 1'-methylspiro[benzothiophene-3,4'-piperidine] | 2-methyl-2-azabicyclo[2.2.2]octane |
| 240 | 1-(1-methyl-4-phenylpiperidin-4-yl)ethanone | 2-methyl-2-azabicyclo[2.2.2]octane |
| 241 | 1-methyl-4-phenylpiperidine | 2-methyl-2-azabicyclo[2.2.2]octane |
| 242 | 4-(4-fluorophenyl)-1-methylpiperidine | 2-methyl-2-azabicyclo[2.2.2]octane |
| 243 | 1-methyl-4-(3-(trifluoromethyl)phenyl)piperidin-4-ol | 2-methyl-2-azabicyclo[2.2.2]octane |

-continued

| Ex. # | R[7] | R = NR[1]R[2] |
|---|---|---|
| 244 | 4-chloro-3-(trifluoromethyl)phenyl-4-hydroxy-1-methylpiperidin-4-yl | N-methyl-azabicyclo[2.2.2]octyl |
| 245 | 4-phenyl-1-methylpiperidin-4-yl | N,N-dimethylamino |
| 246 | 4-(4-fluorophenyl)-1-methylpiperidin-4-yl | N,N-dimethylamino |
| 247 | 4-acetyl-4-phenyl-1-methylpiperidin-4-yl | N,N-dimethylamino |
| 248 | spiro[1-benzothiophene-3,4'-(1'-methylpiperidine)]-yl | N,N-dimethylamino |
| 249 | 3-phenyl-1-methyl-2,5-dihydro-1H-pyrrol-3-yl | N-methyl-azabicyclo[2.2.2]octyl |
| 250 | 3-phenyl-1-methylpyrrolidin-3-yl | N-methyl-azabicyclo[2.2.2]octyl |
| 251 | 1-methylindolin-yl | N-methyl-azabicyclo[2.2.2]octyl |
| 252 | N-methyl-naphthalen-1-ylamino | N-methyl-azabicyclo[2.2.2]octyl |
| 253 | 2-methyl-1,2,3,4-tetrahydroisoquinolin-yl | N-methyl-azabicyclo[2.2.2]octyl |
| 254 | N-methyl-1H-indol-5-ylamino | N-methyl-azabicyclo[2.2.2]octyl |

-continued

| Ex. # | R⁷ | R = NR¹R² |
|---|---|---|
| 255 | 6-(methylamino)-benzo[d][1,3]dioxole | 1-methyl-1-azabicyclo[2.2.2]octane |
| 256 | 5-(methylamino)-1H-indazole | 1-methyl-1-azabicyclo[2.2.2]octane |
| 257 | 5-(methylamino)-1H-benzotriazole | 1-methyl-1-azabicyclo[2.2.2]octane |
| 258 | 6-(methylamino)-1H-indazole | 1-methyl-1-azabicyclo[2.2.2]octane |
| 259 | 2-methyl-6-(methylamino)-benzothiazole | 1-methyl-1-azabicyclo[2.2.2]octane |
| 260 | 2,2-difluoro-6-(methylamino)-benzo[d][1,3]dioxole | 1-methyl-1-azabicyclo[2.2.2]octane |
| 261 | 5-methoxy-2-methylpyridine | 1-methyl-1-azabicyclo[2.2.2]octane |
| 262 | 6-(methylamino)-benzothiazole | 1-methyl-1-azabicyclo[2.2.2]octane |
| 263 | 5-(methylamino)-1,3-dihydroisobenzofuran | 1-methyl-1-azabicyclo[2.2.2]octane |
| 264 | 1-acetyl-5-(methylamino)-2,3-dihydro-1H-indole | 1-methyl-1-azabicyclo[2.2.2]octane |

-continued

| Ex. # | R⁷ | R = NR¹R² |
|---|---|---|
| 265 | benzothiophene-1,1-dioxide-5-yl-NH- | N-methyl-azabicyclo[2.2.2]octane |
| 266 | 2,2-difluoro-benzo[1,3]dioxol-5-yl-NH- | N-methyl-azabicyclo[2.2.1]heptane |
| 267 | 2-methyl-benzothiazol-6-yl-NH- | N-methyl-azabicyclo[2.2.1]heptane |
| 268 | benzothiazol-5-yl-NH- | N-methyl-azabicyclo[2.2.1]heptane |
| 269 | 1H-benzimidazol-5-yl-NH- | N-methyl-azabicyclo[2.2.1]heptane |
| 270 | thieno[2,3-b]pyridin-5-yl-NH- | N-methyl-azabicyclo[2.2.1]heptane |
| 271 | benzothiazol-5-yl-NH- | N-methyl-azabicyclo[2.2.1]heptane |
| 272 | 2-acetamido-4-(methylamino)-1-ethoxybenzene | N-methyl-azabicyclo[2.2.2]octane |
| 273 | 2-methyl-2H-indazol-5-yl-NH- | N-methyl-azabicyclo[2.2.2]octane |
| 274 | 1-methyl-1H-indazol-5-yl-NH- | N-methyl-azabicyclo[2.2.2]octane |

-continued

| Ex. # | R⁷ | R = NR¹R² |
|---|---|---|
| 275 | 1-methyl-1H-indazol-6-yl(methyl)amino | N-methyl-azabicyclo[2.2.2]octane |
| 276 | 2-methyl-2H-indazol-6-yl(methyl)amino | N-methyl-azabicyclo[2.2.2]octane |
| 277 | 2-methylbenzothiazol-5-yl(methyl)amino | N-methyl-azabicyclo[2.2.1]heptane |
| 278 | 2-methylbenzothiazol-5-yl(methyl)amino | N-methyl-azabicyclo[2.2.2]octane |
| 279 | benzo[1,2,5]thiadiazol-5-yl(methyl)amino | N-methyl-azabicyclo[2.2.2]octane |
| 280 | 1,2,3-trimethyl-1H-indol-5-yl(methyl)amino | N-methyl-azabicyclo[2.2.2]octane |
| 281 | 3-oxo-2,3-dihydro-1H-isoindol-5-yl(methyl)amino | N-methyl-azabicyclo[2.2.2]octane |
| 282 | (E)-2-(4-chloropyridin-4-yl)propenyl | N-methyl-ethylamine |
| 321 | 3-(4-trifluoromethylphenyl)propyl | N-(1-methylpyrrolidin-3-yl)acetamide |
| 322 | 3-(4-trifluoromethylphenyl)propyl | 1-methyl-3-(1-methylpyrrolidin-3-yl)urea |
| 323 | 3-(4-trifluoromethylphenyl)propyl | (1-methylpyrrolidin-3-yl)urea |

-continued

| Ex. # | R⁷ | R = NR¹R² |
|---|---|---|
| 324 | 4-(CF₃)-C₆H₄-CH₂CH₂CH₂- | 1-methyl-3-(methanesulfonylamino)pyrrolidine |
| 325 | 4-(CF₃)-C₆H₄-CH₂CH₂CH₂- | 1-BOC-3-(methylamino)pyrrolidine |
| 326 | 4-(CF₃)-C₆H₄-CH₂CH₂CH₂- | 3-(methylamino)pyrrolidine |
| 327 | 4-(CF₃)-C₆H₄-CH₂CH₂CH₂- | 3-(methylamino)-1-(N-methylcarbamoyl)pyrrolidine |
| 328 | 4-(CF₃)-C₆H₄-CH₂CH₂CH₂- | 3-(methylamino)-1-(trifluoroacetyl)pyrrolidine |
| 329 | 4-(CF₃)-C₆H₄-CH₂CH₂CH₂- | 1-acetyl-3-(methylamino)pyrrolidine |
| 330 | 4-(CF₃)-C₆H₄-CH₂CH₂CH₂- | 1-BOC-3-(methylamino)azetidine |
| 331 | 4-(CF₃)-C₆H₄-CH₂CH₂CH₂- | 3-(methylamino)azetidine |
| 332 | 4-(CF₃)-C₆H₄-CH₂CH₂CH₂- | 1-methyl-3-(propionylamino)pyrrolidine |
| 333 | 4-(CF₃)-C₆H₄-CH₂CH₂CH₂- | 2-methyl-5-(methanesulfonyl)-2,5-diazabicyclo[2.2.1]heptane |
| 334 | 4-(CF₃)-C₆H₄-CH₂CH₂CH₂- | 1-methyl-3-(isobutyrylamino)pyrrolidine |
| 335 | 4-(CF₃)-C₆H₄-CH₂CH₂CH₂- | 1-methyl-3-(isobutyrylamino)pyrrolidine |

-continued
| Ex. # | R⁷ | R = NR¹R² |
|---|---|---|
| 336 | 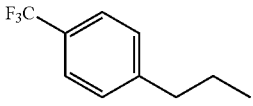 | 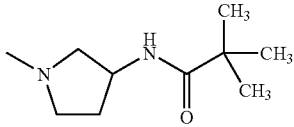 |
| 337 | 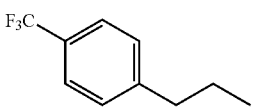 | 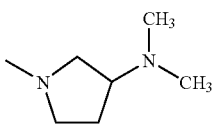 |
| 338 | 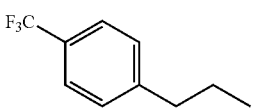 | 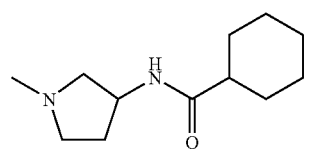 |
| 339 | 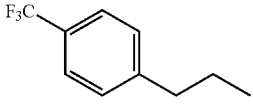 | 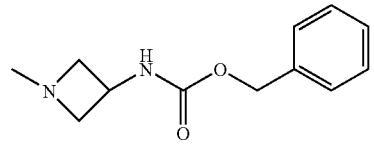 |
| 340 | 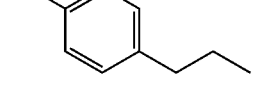 | 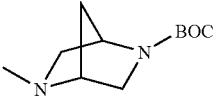 |
| 341 | 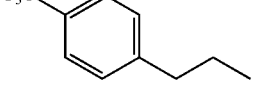 | 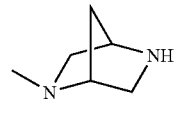 |
| 342 | 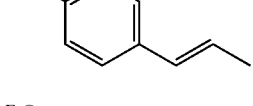 | 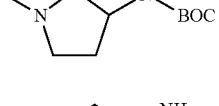 |
| 343 | 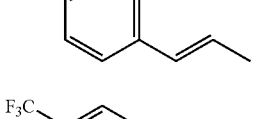 | 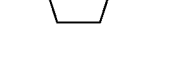 |
| 344 | 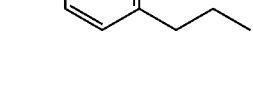 | 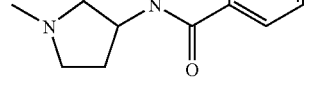 |
| 345 | 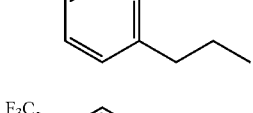 | 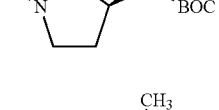 |
| 346 | 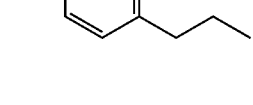 | 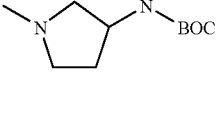 |

-continued
| Ex. # | R⁷ | R = NR¹R² |
|---|---|---|
| 347 | 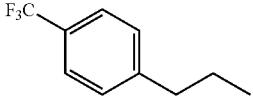 | 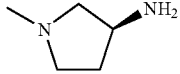 |
| 348 | 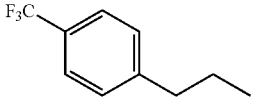 | 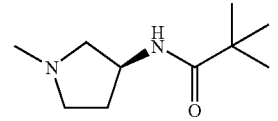 |
| 349 | 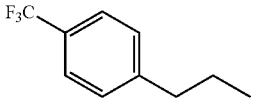 |  |
| 350 | 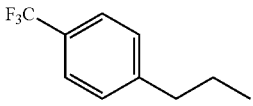 | 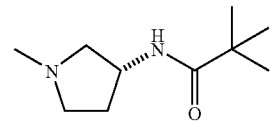 |
| 351 | 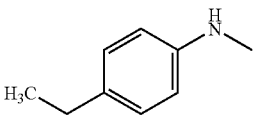 | 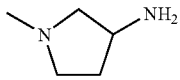 |
| 352 | 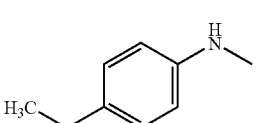 | 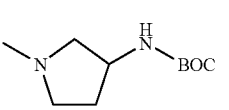 |
| 353 | 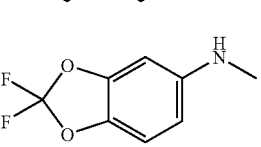 | 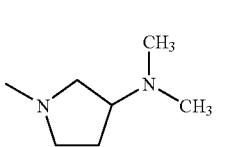 |
| 354 | 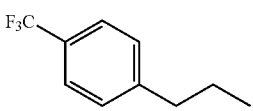 | 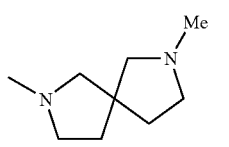 |
| 355 | 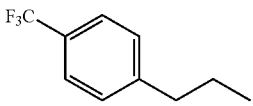 | 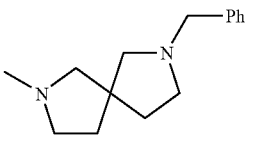 |
| 356 | 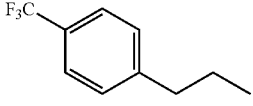 | 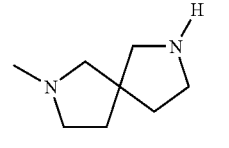 |
| 357 | 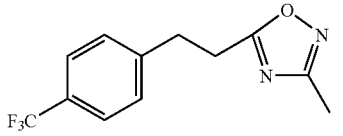 | 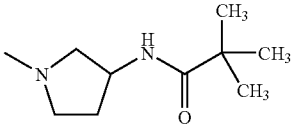 |

| Ex. # | R⁷ | R = NR¹R² |
|---|---|---|
| 358 | 4-(CF₃)C₆H₄-CH₂CH₂-(3-methyl-1,2,4-oxadiazol-5-yl) | 1-methylpyrrolidin-3-yl-NHC(O)Et |
| 359 | 4-(CF₃)C₆H₄-CH₂CH₂-(3-methyl-1,2,4-oxadiazol-5-yl) | 1-methylpyrrolidin-3-yl-NHC(O)CH(Me)₂ |
| 360 | 4-(CF₃)C₆H₄-CH₂CH₂-(3-methyl-1,2,4-oxadiazol-5-yl) | 1-methylpyrrolidin-3-yl-NHC(O)OC(Me)₃ |
| 361 | 4-(CF₃)C₆H₄-CH₂CH₂-(3-methyl-1,2,4-oxadiazol-5-yl) | 1-methyl-3-aminopyrrolidine |
| 362 | 4-(CF₃)C₆H₄-CH₂CH₂-(5-methyl-1,2,4-oxadiazol-3-yl) | 1-methylpyrrolidin-3-yl-NHC(O)Et | or a pharmaceutically acceptable salt thereof.

7. The compound according to claim 1 of structural formula:

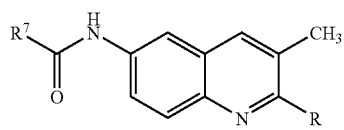

wherein: R⁷ and R are as illustrated in the table below:

| Ex. # | R⁷ | R = NR¹R² |
|---|---|---|
| 283 | 4-(CF₃)C₆H₄-CH=CH- | N(CH₃)₂ |
| 284 | 4-Cl-C₆H₄-CH=CH- | N(CH₃)₂ |
| 285 | 4-(CF₃)C₆H₄-CH₂CH₂CH₂- | N(CH₃)₂ |
| 286 | 4-(CF₃)C₆H₄-CH=CH- | 1-methyl-quinuclidinyl |
| 287 | 4-Cl-C₆H₄-CH=CH- | 1-methyl-quinuclidinyl |
| 288 | 4-(CF₃)C₆H₄-CH₂CH₂CH₂- | 1-methyl-quinuclidinyl |

-continued

| Ex. # | R⁷ | R = NR¹R² |
|---|---|---|
| 289 | 4-(F₃C)C₆H₄-CH=CH-CH₃ (trans-propenyl) | N-methylmorpholine |
| 290 | 4-(F₃C)C₆H₄-CH₂CH₂CH₃ | N-methylmorpholine |
| 291 | 4-(F₃C)C₆H₄-NH-CH₃ | N(CH₃)₂ (dimethylamino) |
| 292 | 4-(F₃C)C₆H₄-NH-CH₃ | N-methylmorpholine |
| 293 | 4-(F₃C)C₆H₄-CH₂CH₂CH₃ | 2-methyl-2-azabicyclo[2.2.1]heptane |
| 294 | 4-(F₃C)C₆H₄-CH=CH-CH₃ | 2-methyl-2-azabicyclo[2.2.1]heptane |
| 295 | 4-(F₃C)C₆H₄-CH₂CH₂CH₃ | N-methylpyrrolidine |
| 296 | 4-(F₃C)C₆H₄-CH₂CH₂CH₃ | N-methylazetidine |
| 297 | 4-(F₃C)C₆H₄-NH-CH₃ | N-methylazetidine |
| 298 | 6-(F₃C)pyridin-3-yl-CH₂CH₂CH₃ | N(CH₃)₂ |
| 299 | 6-(F₃C)pyridin-3-yl-CH₂CH₂CH₃ | N-methylazetidine |
| 300 | 4-(F₃C)C₆H₄-NH-CH₃ | 2-methyl-2-azabicyclo[2.2.1]heptane |
| 301 | 4-(F₃C)C₆H₄-NH-CH₃ | N-methylpyrrolidine |
| 302 | 4-(F₃CO)C₆H₄-NH-CH₃ | 2-methyl-2-azabicyclo[2.2.1]heptane |
| 303 | 4-(F₃C)C₆H₄-NH-CH₃ | N(CH₃)₂-CH(CH₃)₂ (N,N-dimethyl-isopropylamine type) |
| 304 | 4-(F₃C)C₆H₄-CH₂CH₂CH₃ | N(CH₃)₂-CH(CH₃)₂ |
| 305 | 6-(F₃C)pyridin-3-yl-CH₂CH₂CH₃ | N(CH₃)₂-CH(CH₃)₂ |
| 306 | 6-(F₃C)pyridin-3-yl-CH₂CH₂CH₃ | 2-methyl-2-azabicyclo[2.2.1]heptane |
| 307 | 6-(F₃C)pyridin-3-yl-CH₂CH₂CH₃ | N-methyl-azabicyclo[2.2.2]octane |
| 308 | 4'-(F₃C)-4-methylbiphenyl | N-methyl-azabicyclo[2.2.2]octane |
| 309 | 6-phenylpyridin-3-yl-CH₃ | N-methyl-azabicyclo[2.2.2]octane |
| 310 | 4-phenylbicyclo[2.2.2]octan-1-yl-CH₃ | N-methyl-azabicyclo[2.2.2]octane | or a pharmaceutically acceptable salt thereof.

8. The compound according to claim 1 of structural formula:

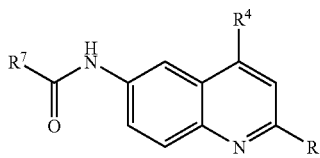

wherein: R⁷, R⁴ and R are as illustrated in the table below:

| Ex. # | R⁷ | R⁴ | R = NR¹R² |
|---|---|---|---|
| 311 | 4-(F₃C)-C₆H₄-CH=CH- | —CH₃ | —N(CH₃)₂ |
| 312 | 4-(F₃C)-C₆H₄-CH₂-CH₂- | —CH₃ | —N(CH₃)₂ |
| 313 | 4-(F₃C)-C₆H₄-CH=CH- | —CH₃ | quinuclidin-3-yl |
| 314 | 4-(F₃C)-C₆H₄-CH₂-CH₂- | —CH₃ | quinuclidin-3-yl |
| 315 | 4-(F₃C)-C₆H₄-CH₂-CH₂- | —CH₂CH₃ | —N(CH₃)₂ |
| 316 | 4-(F₃C)-C₆H₄-CH=CH- | —CH₂CH₃ | pyrrolidin-1-yl |
| 317 | 4-(F₃C)-C₆H₄-CH₂-CH₂- | —CH₂CH₃ | pyrrolidin-1-yl |
| 318 | 4-(F₃C)-C₆H₄-N(CH₃)- | —CH₂CH₃ | —N(CH₃)₂ |
| 319 | 4-(F₃C)-C₆H₄-CH₂-CH₂- | —CO₂CH₃ | 2-azabicyclo[2.2.1]hept-2-yl |
| 320 | 4-(F₃C)-C₆H₄-N(CH₃)- | —CO₂CH₃ | 2-azabicyclo[2.2.1]hept-2-yl | or a pharmaceutically acceptable salt thereof.

9. The compound according to claim 1, selected from:
(1) (2E)-3-(4-chlorophenyl)-N-[2-(dimethylamino)quinolin-6-yl]prop-2-enamide,
(2) (2E)-N-[2-(dimethylamino)quinolin-6-yl]-3-[4-(trifluoromethyl)phenyl]prop-2-enamide,
(3) (2E)-3-(4-chlorophenyl)-N-[2-(ethylamino)quinolin-6-yl]prop-2-enamide,
(4) (2E)-N-[2-(ethylamino)quinolin-6-yl]-3-[4-(trifluoromethyl)phenyl]prop-2-enamide,
(5) (2E)-3-(4-chlorophenyl)-N-[2-(propylamino)quinolin-6-yl]prop-2-enamide,
(6) (2E)-N-[2-(propylamino)quinolin-6-yl]-3-[4-(trifluoromethyl)phenyl]prop-2-enamide,
(7) (2E)-3-(4-chlorophenyl)-N-[2-(isopropylamino)quinolin-6-yl]prop-2-enamide,
(8) (2E)-N-[2-(isopropylamino)quinolin-6-yl]-3-[4-(trifluoromethyl)phenyl]prop-2-enamide,
(9) (2E)-N-[2-(2-azabicyclo[2.2.2]oct-2-yl)quinolin-6-yl]-3-(4-chlorophenyl)prop-2-enamide,
(10) (2E)-N-[2-(2-azabicyclo[2.2.2]oct-2-yl)quinolin-6-yl]-3-[4-(trifluoromethyl)phenyl]prop-2-enamide,
(11) (2E)-N-[2-(2-azabicyclo[2.2.2]oct-2-yl)-3-methylquinolin-6-yl]-3-(4-chlorophenyl)prop-2-enamide,
(12) (2E)-N-[2-(dimethylamino)-4-methylquinolin-6-yl]-3-[4-(trifluoromethyl)phenyl]prop-2-enamide,
(13) N-[2-(dimethylamino)-4-methylquinolin-6-yl]-3-[4-(trifluoromethyl)phenyl]propanamide,
(14) N-[2-(2-azabicyclo[2.2.2]oct-2-yl)quinolin-6-yl]—N'-[4-(methylthio)phenyl]urea,
(15) N-[2-(2-azabicyclo[2.2.2]oct-2-yl)quinolin-6-yl]-3-[6-(trifluoromethyl)pyridin-3-yl]propanamide,
(16) N-[2-(2-azabicyclo[2.2.2]oct-2-yl)quinolin-6-yl]-N'-[4-(trifluoromethoxy)phenyl]urea,
(17) (2E)-N-[2-(2-azabicyclo[2.2.2]oct-2-yl)quinolin-6-yl]-3-(4-ethylphenyl)prop-2-enamide,
(18) N-[2-(2-azabicyclo[2.2.2]oct-2-yl)quinolin-6-yl]-N'-(4-isopropylphenyl)urea,
(19) N-[2-(2-azabicyclo[2.2.2]oct-2-yl)quinolin-6-yl]-3-(4-ethylphenyl)propanamide,
(20) N-[2-(2-azabicyclo[2.2.2]oct-2-yl)quinolin-6-yl]-N'-[4-(trifluoromethyl)phenyl]urea,
(21) N-[2-(2-azabicyclo[2.2.2]oct-2-yl)quinolin-6-yl]-N'-(4-methoxyphenyl)urea,
(22) (2E)-N-[2-(2-azabicyclo[2.2.2]oct-2-yl)quinolin-6-yl]-3-(4-methoxyphenyl)prop-2-enamide,
(23) N-[2-(dimethylamino)quinolin-6-yl]-N'-[4-(methylthio)phenyl]urea,
(24) (2E)-N-[2-(2-azabicyclo[2.2.2]oct-2-yl)-4-methylquinolin-6-yl]-3-[4-(trifluoromethyl)phenyl]prop-2-enamide,
(25) N-[2-(2-azabicyclo[2.2.2]oct-2-yl)-4-methylquinolin-6-yl]-3-[4-(trifluoromethyl)phenyl]propanamide,
(26) N-[2-(2-azabicyclo[2.2.2]oct-2-yl)quinolin-6-yl]-N'-(4-ethylphenyl)urea,
(27) N-(2-pyrrolidin-1-ylquinolin-6-yl)-3-[4-(trifluoromethyl)phenyl]propanamide,
(28) (2E)-N-(2-pyrrolidin-1-ylquinolin-6-yl)-3-[4-(trifluoromethyl)phenyl]prop-2-enamide,
(29) (2E)-N-(2-azetidin-1-ylquinolin-6-yl)-3-[4-(trifluoromethyl)phenyl]prop-2-enamide,
(30) N-[2-(2-azabicyclo[2.2.1]hept-2-yl)quinolin-6-yl]-3-[4-(trifluoromethyl)phenyl]propanamide,
(31) N-(2-azetidin-1-ylquinolin-6-yl)-3-[4-(trifluoromethyl)phenyl]propanamide,
(32) (2E)-N-[2-(butylamino)quinolin-6-yl]-3-[4-(trifluoromethyl)phenyl]prop-2-enamide,

(33) (2E)-N-[2-(isobutylamino)quinolin-6-yl]-3-[4-(trifluoromethyl)phenyl]prop-2-enamide,
(34) N-[2-(isobutylamino)quinolin-6-yl]-3-[4-(trifluoromethyl)phenyl]propanamide,
(35) (2E)-N-[2-(2-azabicyclo[2.2.1]hept-2-yl)quinolin-6-yl]-3-[4-(trifluoromethyl)phenyl]prop-2-enamide,
(36) N-[2-(2-azabicyclo[2.2.2]oct-2-yl)quinolin-6-yl]-N'-(2,3-dihydro-1H-inden-5-yl)urea,
(37) (2E)-N-[2-(sec-butylamino)quinolin-6-yl]-3-[4-(trifluoromethyl)phenyl]prop-2-enamide,
(38) N-[2-(sec-butylamino)quinolin-6-yl]-3-[4-(trifluoromethyl)phenyl]propanamide,
(39) N-[2-(2-azabicyclo[2.2.2]oct-2-yl)quinolin-6-yl]-N'-(4-propylphenyl)urea,
(40) N-[2-(2-azabicyclo[2.2.1]hept-2-yl)-3-methylquinolin-6-yl]-3-[4-(trifluoromethyl)phenyl]propanamide,
(41) N-[2-(cyclopentylamino)quinolin-6-yl]-3-[4-(trifluoromethyl)phenyl]propanamide,
(42) N-(2-{[(1R)-1-methylpropyl]amino}quinolin-6-yl)-3-[4-(trifluoromethyl)phenyl]propanamide,
(43) (2E)-N-[2-(2-azabicyclo[2.2.1]hept-2-yl)-3-methylquinolin-6-yl]-3-[4-(trifluoromethyl)phenyl]prop-2-enamide,
(44) N-{2-[isopropyl(methyl)amino]quinolin-6-yl}-3-[4-(trifluoromethyl)phenyl]propanamide
(45) N-(2-{[(1S)-1-methylpropyl]amino}quinolin-6-yl)-3-[4-(trifluoromethyl)phenyl]propanamide,
(46) N-(3-methyl-2-pyrrolidin-1-ylquinolin-6-yl)-3-[4-(trifluoromethyl)phenyl]propanamide,
(47) (2E)-N-(4-ethyl-2-pyrrolidin-1-ylquinolin-6-yl)-3-[4-(trifluoromethyl)phenyl]propanamide,
(48) N-[2-(3-methylpyrrolidin-1-yl)quinolin-6-yl]-3-[4-(trifluoromethyl)phenyl]propanamide,
(49) N-[2-(2-methylpyrrolidin-1-yl)quinolin-6-yl]-3-[4-(trifluoromethyl)phenyl]propanamide,
(50) N-{2-[(1,2-dimethylpropyl)amino]quinolin-6-yl}-3-[4-(trifluoromethyl)phenyl]propanamide,
(51) N-{2-[ethyl(methyl)amino]quinolin-6-yl}-3-[4-(trifluoromethyl)phenyl]propanamide,
(52) N-{2-[methyl(propyl)amino]quinolin-6-yl}-3-[4-(trifluoromethyl)phenyl]propanamide,
(53) N-(2-azetidin-1-yl-3-methylquinolin-6-yl)-3-[4-(trifluoromethyl)phenyl]propanamide,
(54) N-[2-(2-azabicyclo[2.2.2]oct-2-yl)quinolin-6-yl]-N'-(2,2-difluoro-1,3-benzodioxol-5-yl)urea,
(55) N-[2-(isopropylamino)quinolin-6-yl]-3-[4-(trifluoromethyl)phenyl]propanamide,
(56) N-{2-[isopropyl(methyl)amino]quinolin-6-yl}-3-[6-(trifluoromethyl)pyridin-3-yl]propanamide,
(57) N-(2-azetidin-1-yl-3-methylquinolin-6-yl)-N'-[4-(trifluoromethyl)phenyl]urea,
(58) N-[2-(2-azabicyclo[2.2.1]hept-2-yl)-3-methylquinolin-6-yl]-N'-[4-(trifluoromethyl)phenyl]urea,
(59) N-(3-methyl-2-pyrrolidin-1-ylquinolin-6-yl)-N'-[4-(trifluoromethyl)phenyl]urea,
(60) N-{2-[(1-methylbutyl)amino]quinolin-6-yl}-3-[4-(trifluoromethyl)phenyl]propanamide,
(61) N-[2-(2-azabicyclo[2.2.1]hept-2-yl)quinolin-6-yl]-N'-(2,2-difluoro-1,3-benzodioxol-5-yl)urea,
(62) N-[2-(2-azabicyclo[2.2.2]hept-2-yl)quinolin-6-yl]-N'-(2-methyl-1,3-benzothiazol-6-yl)urea,
(63) N-{2-[cyclopentyl(methyl)amino]quinolin-6-yl}-3-[4-(trifluoromethyl)phenyl]propanamide,
(64) N-[2-(2-azabicyclo[2.2.1]hept-2-yl)-3-methylquinolin-6-yl]-N'-[4-(trifluoromethyl)phenyl]propanamide,
(65) N-[2-(2-azabicyclo[2.2.2]oct-2-yl)quinolin-6-yl]-N'-{4-[(trifluoromethyl)thio]phenyl}urea,
(66) N-[2-(2-azabicyclo[2.2.1]hept-2-yl)-3-methylquinolin-6-yl]-3-[6-(trifluoromethyl)pyridin-3-yl]propanamide,
(67) N-{2-[cyclobutyl(methyl)amino]quinolin-6-yl}-3-[4-(trifluoromethyl)phenyl]propanamide,
(68) N-[2-(2-azabicyclo[2.2.2]oct-2-yl)quinolin-6-yl]-3-(1,3-benzothiazol-2-yl)propanamide,
(69) N-{2-[(1R,4S)-2-azabicyclo[2.2.1]hept-2-yl]quinolin-6-yl}-3-[6-(trifluoromethyl)pyridin-3-yl]propanamide,
(70) N-{2-[(1S,4R)-2-azabicyclo[2.2.1]hept-2-yl]quinolin-6-yl}-3-[6yl]propanamide,
(71) (2E)-N-{2-[isopropyl(methyl)amino]quinolin-6-yl}-3-[4-(trifluoromethyl)phenyl]prop-2-enamide,
(72) (2E)-3-(4-chlorophenyl)-N-{2-[isopropyl(methyl)amino]quinolin-yl}prop-2-enamide,
(73) N-[2-(pyrrolidin-3-ylamino)quinolin-6-yl]-3-[4-(trifluoromethyl)phenyl]propanamide,
(74) N-{2-[3-(acetylamino)pyrrolidin-1-yl]quinolin-6-yl}-3-[4-(trifluoromethyl)phenyl]propanamide,
(75) N-[2-(3-{[(methylamino)carbonyl]amino}pyrrolidin-1-yl)quinolin-6-yl]-3-[4-(trifluoromethyl)phenyl]propanamide,
(76) N-[2-(2-azabicyclo[2.2.1]hept-2-yl)quinolin-6-yl]-N'-(4-ethylphenyl)urea,
(77) (2E)-N-[2-(2-azabicyclo[2.2.2]oct-2-yl)quinolin-6-yl]-3-[4-(methylthio)phenyl]prop-2-enamide,
(78) N-[2-(2-azabicyclo[2.2.1]hept-2-yl)quinolin-6-yl]-N'-{4-[(trifluoromethyl)thio]phenyl}urea,
(79) N-[2-(2-azabicyclo[2.2.1]hept-2-yl)quinolin-6-yl]-N'-[4-(methylthio)phenyl]urea,
(80) N-[2-(2-azabicyclo[2.2.1]hept-2-yl)quinolin-6-yl]-N'-[4-(trifluoromethoxy)phenyl]urea,
(81) N-{2-[methyl(tetrahydrofuran-3-yl)amino]quinolin-6-yl}-3-[4-(trifluoromethyl)phenyl]propanamide,
(82) N-(2-{3-[(methylsulfonyl)amino]pyrrolidin-1-yl}quinolin-6-yl)-3-[4-(trifluoromethyl)phenyl]propanamide,
(83) N-[2-(2-azabicyclo[2.2.1]hept-2-yl)quinolin-6-yl]-3-(1,3-benzothiazol-2-yl)propanamide,
(84) N-{2-[sec-butyl(methyl)amino]quinolin-6-yl}-3-[4-(trifluoromethyl)phenyl]propanamide,
(85) N-{2-[3-(propionylamino)pyrrolidin-1-yl]quinolin-6-yl}-3-[4-(trifluoromethyl)phenyl]propanamide,
(86) 2-{methyl[6-({3-[4-(trifluoromethyl)phenyl]propanoyl}amino)quinolin-2-yl]amino}propylacetate,
(87) N-{2-[methyl(1-tetrahydrofuran-2-ylethyl)amino]quinolin-6-yl}-3-[4-(trifluoromethyl)phenyl]propanamide,
(88) N-[2-(3-{[(dimethylamino)carbonyl]amino}pyrrolidin-1-yl)quinolin-6-yl]-3-[4-(trifluoromethyl)phenyl]propanamide,
(89) 2-methyl-N-{1-[6-({3-[4-(trifluoromethyl)phenyl]propanoyl}amino)quinolin-2-yl]pyrrolidin-3-yl}propanamide,
(90) N-{2-[3-(dimethylamino)pyrrolidin-1-yl]quinolin-6-yl}-3-[4-(trifluoromethyl)phenyl]propanamide,
(91) N-{1-[6-({3-[4-(trifluoromethyl)phenyl]propanoyl}amino)quinolin-2-yl]pyrrolidin-3-yl}cyclohexanecarboxamide,
(92) N-(4-ethylphenyl)-N'-{2-[isopropyl(methyl)amino]quinolin-6-yl}urea,
(93) 2,2-dimethyl-N-{1-[6-({3-[4-(trifluoromethyl)phenyl]propanoyl}amino)quinolin-2-yl]pyrrolidin-3-yl}propanamide,
(94) (2E)-N-[2-(3-aminopyrrolidin-1-yl)quinolin-6-yl]-3-[4-(trifluoromethyl)phenyl]prop-2-enamide

(95) N-{2-[isopropyl(methyl)amino]quinolin-6-yl}-N'-[4-(methylthio)phenyl]urea,
(96) N-{2-[isopropyl(methyl)amino]quinolin-6-yl}-N'-[4-(trifluoromethyl)phenyl]urea,
(97) N-{1-[6-({[(4-ethylphenyl)amino]carbonyl}amino)quinolin-2-yl]pyrrolidin-3-yl}-2,2-dimethylpropanamide,
(98) N-{2-[3-(dimethylamino)pyrrolidin-1-yl]quinolin-6-yl}-N'-(4-ethylphenyl)urea,
(99) tert-butyl methyl{1-[6-({3-[4-(trifluoromethyl)phenyl]propanoyl}amino)quinolin-2-yl]pyrrolidin-3-yl}carbamate,
(100) N-(2,2-difluoro-1,3-benzodioxol-5-yl)-N'-{2-[3-(dimethylamino)pyrrolidin-1-yl]quinolin-6-yl}urea,
(101) N-{2-[(3S)-3-aminopyrrolidin-1-yl]quinolin-6-yl}-3-[4-(trifluoromethyl)phenyl]propanamide,
(102) N-{2-[3-(methylamino)pyrrolidin-1-yl]quinolin-6-yl}-3-[4-(trifluoromethyl)phenyl]propanamide,
(103) 2,2-dimethyl-N-{(3S)-1-[6-({3-[4-(trifluoromethyl)phenyl]propanoyl}amino)quinolin-2-yl]pyrrolidin-3-yl}propanamide,
(104) 2,2-dimethyl-N-{(3R)-1-[6-({3-[4-(trifluoromethyl)phenyl]propanoyl}amino)quinolin-2-yl]pyrrolidin-3-yl}propanamide,
(105) N,2,2-trimethyl-N-{1-[6-({3-[4-(trifluoromethyl)phenyl]propanoyl}amino)quinolin-2-yl]pyrrolidin-3-yl}propanamide,
(106) N-{2-[(3S)-3-(propionylamino)pyrrolidin-1-yl]quinolin-6-yl}-3-[4-(trifluoromethyl)phenyl]propanamide,
(107) (2E)-N-(2-{3-[(methylsulfonyl)amino]pyrrolidin-1-yl}quinolin-6-yl)-3-[4-(trifluoromethyl)phenyl]prop-2-enamide,
(108) (2E)-N-[2-(2-azabicyclo[2.2.2]oct-2-yl)quinolin-6-yl]-3-[4-(ethylthio)phenyl]prop-2-enamide,
(109) tert-butyl 1-(6-{[(2E)-3-(4-chlorophenyl)prop-2-enoyl]amino}quinolin-2-yl)pyrrolidin-3-ylcarbamate,
(110) (2E)-N-[2-(3-aminopyrrolidin-1-yl)quinolin-6-yl]-3-(4-chlorophenyl)prop-2-enamide,
(111) N-{1-[6-({[(4-ethylphenyl)amino]carbonyl}amino)quinolin-2-yl]pyrrolidin-3-yl}methanesulfonamide,
(112) N-{2-[3-(dimethylamino)pyrrolidin-1-yl]quinolin-6-yl}-N'-[4-(trifluoromethyl)phenyl]urea,
(113) N-{2-[3-(dimethylamino)pyrrolidin-1-yl]quinolin-6-yl}-N'-[4-(trifluoromethoxy)phenyl]urea,
(114) N-{2-[(3R)-3-(propionylamino)pyrrolidin-1-yl]quinolin-6-yl}-3-[4-(trifluoromethyl)phenyl]propanamide,
(115) N-[2-(7-methyl-2,7-diazaspiro[4.4]non-2-yl)quinolin-6-yl]-3-[4-(trifluoromethyl)phenyl]propanamide,
(116) N-[2-(2-azabicyclo[2.2.2]oct-2-yl)quinolin-6-yl]-N²-(4-ethylphenyl)ethane-1,2-diamine,
(117) N-[2-(7-benzyl-2,7-diazaspiro[4.4]non-2-yl)quinolin-6-yl]-3-[4-(trifluoromethyl)phenyl]propanamide,
(118) N-[2-(2-azabicyclo[2.2.1]hept-2-yl)-4-(dimethylamino)quinolin-6-yl]-4'-(trifluoromethyl)-1,1'-biphenyl-4-carboxamide,
(119) N-[2-(2,7-diazaspiro[4.4]non-2-yl)quinolin-6-yl]-3-[4-(trifluoromethyl)phenyl]propanamide,
(120) N-{2-[isopropyl(methyl)amino]quinolin-6-yl}-N'-[4-(trifluoromethoxy)phenyl]urea,
(121) N-[2-(2-azabicyclo[2.2.2]oct-2-yl)quinolin-6-yl]-N'-[6-(trifluoromethyl)pyridin-3-yl]urea,
(122) N-[2-(2-azabicyclo[2.2.2]oct-2-yl)quinolin-6-yl]-N'-(6-ethylpyridin-3-yl)urea,
(123) N-[2-(2-azabicyclo[2.2.2]oct-2-yl)quinolin-6-yl]-3-[4-(methylsulfonyl)phenyl]propanamide,
(124) 2,2-dimethyl-N-{1-[6-(5-{2-[4-(trifluoromethyl)phenyl]ethyl}-1,2,4-oxadiazol-3-yl)quinolin-2-yl]pyrrolidin-3-yl}propanamide,
(125) 1-[6-(5-{2-[4-(trifluoromethyl)phenyl]ethyl}-1,2,4-oxadiazol-3-yl)quinolin-2-yl]pyrrolidin-3-amine,
(126) N-{1-[6-(5-{2-[4-(trifluoromethyl)phenyl]ethyl}-1,2,4-oxadiazol-3-yl)quinolin-2-yl]pyrrolidin-3-yl}propanamide,
(127) 2-methyl-N-{1-[6-(5-{2-[4-(trifluoromethyl)phenyl]ethyl}-1,2,4-oxadiazol-3-yl)quinolin-2-yl]pyrrolidin-3-yl}propanamide,
(128) N-{1-[6-(3-{2-[4-(trifluoromethyl)phenyl]ethyl}-1,2,4-oxadiazol-5-yl)quinolin-2-yl]pyrrolidin-3-yl}propanamide,
and pharmaceutically accepted salts thereof.
10. The compound according to claim 9, selected from:
(1) (2E)-3-(4-chlorophenyl)-N-[2-(dimethylamino)quinolin-6-yl]prop-2-enamide,
(2) (2E)-N-[2-(dimethylamino)quinolin-6-yl]-3-[4-(trifluoromethyl)phenyl]prop-2-enamide,
(3) (2E)-N-[2-(ethylamino)quinolin-6-yl]-3-[4-(trifluoromethlyl)phenyl]prop-2-enamide,
(4) (2E)-N-[2-(2-azabicyclo[2.2.2]oct-2-yl)quinolin-6-yl]-3-(4-chlorophenyl)prop-2-enamide,
(5) (2E)-N-[2-(2-azabicyclo[2.2.2]oct-2-yl)quinolin-6-yl]-3-[4-(trifluoromethyl)phenyl]prop-2-enamide,
(6) (2E)-N-[2-(dimethylamino)-4-methylquinolin-6-yl]-3-[4-(trifluoromethyl)phenyl]prop-2-enamide,
(7) N-[2-(dimethylamino)4-methylquinolin-6-yl]-3-[4-(trifluoromethyl)phenyl]propanamide,
(8) N-[2-(2-azabicyclo[2.2.2]oct-2-yl)quinolin-6-yl]-N'-[4-(methylthio)phenyl]urea,
(9) N-[2-(2-azabicyclo[2.2.2]oct-2-yl)quinolin-6-yl]-3-[6-(trifluoromethyl)pyridin-3-yl]propanamide,
(10) N-[2-(2-azabicyclo[2.2.2]oct-2-yl)quinolin-6-yl]-N'-[4-(trifluoromethoxy)phenyl]urea,
(11) N-[2-(2-azabicyclo[2.2.2]oct-2-yl)quinolin-6-yl]-N'-(4-isopropylphenyl)urea,
(12) N-[2-(2-azabicyclo[2.2.2]oct-2-yl)quinolin-6-yl]-3-(4-ethylphenyl)propanamide,
(13) N-[2-(2-azabicyclo[2.2.2]oct-2-yl)quinolin-6-yl]-N'-[4-(trifluoromethyl)phenyl]urea,
(14) N-[2-(2-azabicyclo[2.2.2]oct-2-yl)quinolin-6-yl]-N'-(4-methoxyphenyl)urea,
(15) (2E)-N-[2-(2-azabicyclo[2.2.2]oct-2-yl)quinolin-6-yl]-3-(4-methoxyphenyl)prop-2-enamide,
(16) N-[2-(dimethylamino)quinolin-6-yl]-N'-[4-(methylthio)phenyl]urea,
(17) N-[2-(2-azabicyclo[2.2.2]oct-2-yl)quinolin-6-yl]-N'-(4-ethylphenyl)urea,
(18) N-(2-pyrrolidin-1-ylquinolin-6-yl)-3-[4-(trifluoromethyl)phenyl]propanamide,
(19) N-[2-(2-azabicyclo[2.2.1]hept-2-yl)quinolin-6-yl]-3-[4-(trifluoromethyl)phenyl]propanamide,
(20) N-(2-azetidin-1-ylquinolin-6-yl)-3-[4-(trifluoromethyl)phenyl]propanamide,
(21) N-[2-(isobutylamino)quinolin-6-yl]-3-[4-(trifluoromethyl)phenyl]propanamide,
(22) (2E)-N-[2-(2-azabicyclo[2.2.1]hept-2-yl)quinolin-6-yl]-3-[4-(trifluoromethyl)phenyl]prop-2-enamide,
(23) N-[2-(2-azabicyclo[2.2.2]oct-2-yl)quinolin-6-yl]-N'-(2,3-dihydro-1H-inden-5-yl)urea,
(24) N-[2-(sec-butylamino)quinolin-6-yl]-3-[4-(trifluoromethyl)phenyl]propanamide,
(25) N-[2-(2-azabicyclo[2.2.2]oct-2-yl)quinolin-6-yl]-N'-(4-propylphenyl)urea,

(26) N-[2-(2-azabicyclo[2.2.1]hept-2-yl)-3-methylquinolin-6-yl]-3-[4-(trifluoromethyl)phenyl]propanamide,
(27) N-[2-(cyclopentylamino)quinolin-6-yl]-3-[4-(trifluoromethyl)phenyl]propanamide,
(28) N-(2-{[(1R)-1-methylpropyl]amino}quinolin-6-yl)-3-[4-(trifluoromethyl)phenyl]propanamide,
(29) (2E)-N-[2-(2-azabicyclo[2.2.1]hept-2-yl)-3-methylquinolin-6-yl]-3-[4-(trifluoromethyl)phenyl]prop-2-enamide,
(30) N-{2-[isopropyl(methyl)amino]quinolin-6-yl}-3-[4-(trifluoromethyl)phenyl]propanamide,
(31) N-[2-(3-methylpyrrolidin-1-yl)quinolin-6-yl]-3-[4-(trifluoromethyl)phenyl]propanamide,
(32) N-[2-(2-methylpyrrolidin-1-yl)quinolin-6-yl]-3-[4-(trifluoromethyl)phenyl]propanamide,
(33) N-(2-azetidin-1-yl-3-methylquinolin-6-yl)-3-[4-(trifluoromethyl)phenyl]propanamide,
(34) N-[2-(isopropylamino)quinolin-6-yl]-3-[4-(trifluoromethyl)phenyl]propanamide,
(35) N-{2-[isopropyl(methyl)amino]quinolin-6-yl }-3-[6-(trifluoromethyl)pyridin-3-yl]propanamide,
(36) N-(2-azetidin-1-yl-3-methylquinolin-6-yl)-N'-[4-(trifluoromethyl)phenyl]urea,
(37) N-[2-(2-azabicyclo[2.2.1]hept-2-yl)-3-methylquinolin-6-yl]-N'-[4-(trifluoromethmethyl)phenyl]urea,
(38) N-(3-methyl-2-pyrrolidin-1-ylquinolin-6-yl)-N'-[4-(trifluoromethyl)phenyl]urea,
(39) N-{2-[cyclopentyl(methyl)amino]quinolin-6-yl )-3-[4-(trifluoromethyl)phenyl]propanamide,
(40) N-[2-(2-azabicyclo[2.2.1]hept-2-yl)-3-methylquinolin-6-yl]-N'-[4-(trifluoromethoxy)phenyl]urea,
(41) N-[2-(2-azabicyclo[2.2.2]oct-2-yl)quinolin-6-yl]-N'-{4-[(trifluoromethyl)thio]phenyl}urea,
(42) N-[2-(2-azabicyclo[2.2.1]hept-2-yl)-3-methylquinolin-6-yl]-3-[6-(trifluoromethylpyridin-3-yl]propanamide,
(43) N-{2-[(1R,4S)-2-azabicyclo[2.2.1]hept-2-yl]quinolin-6-yl}-3-[6-(trifluoromethyl)pyridin-3-yl]propanamide,
(44) N-{2-[(1S,4R)-2-azabicyclo[2.2.1]hept-2-yl]quinolin-6-yl}-3-[6-trifluoromethyl)pyridin-3-yl]propanamide,
(45) (2E)-N-{2-[isopropyl(methyl)amino]quinolin-6-yl}-3-[4-(trifluoromethyl)phenyl]prop-2-enamide,
(46) (2E)-3-(4-chlorophenyl)-N-{2-[isopropyl(methyl)amino]quinolin-6-yl}prop-2-enamide
(47) N-[2-(pyrrolidin-3-ylamino)quinolin-6-yl]-3-[4-(trifluoromethyl)phenyl]propanamide,
(48) N-{2-[3-(acetylamino)pyrrolidin-1-yl]quinolin-6-yl}-3-[4-(trifluoromethyl)phenyl]propanamide,
(49) N-[2-(3-{[(methylamino)carbonyl]amino}pyrrolidin-1-yl)quinolin-6-yl]-3-[4-(trifluoromethyl)phenyl]propanamide,
(50) N-[2-(2-azabicyclo[2.2.1]hept-2-yl)quinolin-6-yl]-N'-(4-ethylphenyl)urea,
(51) (2E)-N-[2-(2-azabicyclo[2.2.2]oct-2-yl)quinolin-6-yl]-3-[4-(methylthio)phenyl]prop-2-enamide,
(52) N-[2-(2-azabicyclo[2.2.1]hept-2-yl)quinolin-6-yl]-N'-{4-[(trifluoromethyl)thio]phenyl}urea,
(53) N-[2-(2-azabicyclo[2.2.1]hept-2-yl)quinolin-6-yl]-N'-[4-(methylthio)phenyl]urea,
(54) N-[2-(2-azabicyclo[2.2.1]hept-2-yl)quinolin-6-yl]-N'-[4-(trifluoromethoxy)phenyl]urea,
(55) N-{2-[methyl(tetrahydrofuran-3-yl)amino]quinolin-6-yl}-3-[4-(trifluoromethyl)phenyl]propanamide,
(56) N-(2-{3-[(methylsulfonyl)amino]pyrrolidin-1-yl}quinolin-6-yl)-3-[4-(trifluoromethyl)phenyl]propanamide,
(57) N-[2-(2-azabicyclo[2.2.1]hept-2-yl)quinolin-6-yl]-3-(1,3-benzothiazol-2-yl)propanamide,
(58) N-{2-[3-(propionylamino)pyrrolidin-1-yl]quinolin-6-yl}-3-[4-(trifluoromethyl)phenyl]propanamide,
(59) N-[2-(3-{[(dimethylamino)carbonyl]amino}pyrrolidin-1-yl)quinolin-6-yl]-3-[4-(trifluoromethyl)phenyl]propanamide,
(60) 2-methyl-N-{1-[6-({3-[4-(trifluoromethyl)phenyl]propanoyl}amino)quinolin-2-yl]pyrrolidin-3-yl}propanamide,
(61) N-{2-[3-(dimethylamino)pyrrolidin-1-yl]quinolin-6-yl}-3-[4-(trifluoromethyl)phenyl]propanamide,
(62) N-{1-[6-({3-[4-(trifluoromethyl)phenyl]propanoyl}amino)quinolin-2-yl]pyrrolidin-3-yl}cyclohexanecarboxamide,
(63) 2,2-dimethyl-N-{1-[6-({3-[4-(trifluoromethyl)phenyl]propanoyl}amino)quinolin-2-yl]pyrrolidin-3-yl}propanamide,
(64) (2E)-N-[2-(3-aminopyrrolidin-1-yl)quinolin-6-yl]-3-[4-(trifluoromethyl)phenyl]prop-2-enamide,
(65) N-{2-[isopropyl(methyl)amino]quinolin-6-yl}-N'-[4-(methylthio)phenyl]urea,
(66) N-{2-[isopropyl(methyl)amino]quinolin-6-yl}-N'-[4-(trifluoromethyl)phenyl]urea,
(67) N-{1-[6-({[(4-ethylphenyl)amino]carbonyl}amino)quinolin-2-yl]pyrrolidin-3-}-2,2-dimethylpropanamide,
(68) N-{2-[3-(dimethylamino)pyrrolidin-1-yl]quinolin-6-yl}-N'-(4-ethylphenyl)urea,
(69) N-{2-[(3S)-3-aminopyrrolidin-1-yl]quinolin-6-yl}-3-[4-(trifluoromethyl)phenyl]propanamide,
(70) N-{2-[3-(methylamino)pyrrolidin-1-yl]quinolin-6-yl}-3-[4-(trifluoromethylphenyl)propanamide,
(71) 2,2-dimethyl-N-{(3S)-1-[6-({3-[4-(trifluoromethyl)phenyl]propanoyl}amino)quinolin-2-yl]pyrrolidin-3-yl}propanamide,
(72) 2,2-dimethyl-N-{(3R)-1-[6-(3-[4-(trifluoromethyl)phenyl]propanoyl}amino)quinolin-2-yl]pyrrolidin-3-yl}propanamide,
(73) N,2,2-trimethyl-N-{1-[6-({3-[4-(trifluoromethyl)phenyl]propanoyl}amino)quinolin-2-yl]pyrrolidin-3-yl}propanamide,
(74) N-{2-[(3S)-3-(propionylamino)pyrrolidin-1-yl]quinolin-6-yl}-3-[4-(trifluoromethyl)phenyl]propanamide,
(75) (2E)-N-(2-{3-[(methylsulfonyl)amino]pyrrolidin-1-yl}quinolin-6-yl)-3-[4-(trifluoromethyl)phenyl]prop-2-enamide,
(76) (2E)-N-[2-(2-azabicyclo[2.2.2]oct-2-yl)quinolin-6-yl]-3-[4-(ethylthio)phenyl]prop-2-enamide,
(77) tert-butyl 1-(6-{[(2E)-3-(4-chlorophenyl)prop-2-enoyl]amino}quinolin-2-yl)pyrrolidin-3-ylcarbamate,
(78) (2E)-N-[2-(3-aminopyrrolidin-1-yl)quinolin-6-yl]-3-(4-chlorophenyl)prop-2-enamide,
(79) N-{1-[6-({[(4-ethylphenyl)amino]carbonyl}amino)quinolin-2-yl]pyrrolidin-3-yl}methanesulfonamide,
(80) N-{2-[3-(dimethylamino)pyrrolidin-1-yl]quinolin-6-yl}-N'-[4-(trifluoromethyl)phenyl]urea,
(81) N-{2-[3-(dimethylamino)pyrrolidin-1-yl]quinolin-6-yl}-N'-[4-(trifluoromethoxy)phenyl]urea,
(82) N-{2-[(3R)-3-(propionylamino)pyrrolidin-1-yl]quinolin-6-yl}-3-[4-(trifluoromethyl)phenyl]propanamide,

(83) N-[2-(7-methyl-2,7-diazaspiro[4.4]non-2-yl)quinolin-6-yl]-3-[4-(trifluoromethyl)phenyl]propanamide,
(84) N'-[2-(2-azabicyclo[2.2.2]oct-2-yl)quinolin-6-yl]-N²-(4-ethylphenyl)ethane-1,2-diamine,
(85) N-[2-(7-benzyl-2,7-diazaspiro[4.4]non-2-yl)quinolin-6-yl]-3-[4-(trifluoromethyl)phenyl]propanamide,
(86) N-[2-(2-azabicyclo[2.2.1]hept-2-yl)4-(dimethylamino)quinolin-6-yl]-4'-trifluoromethyl)-1,1'-biphenyl-4-carboxamide,
(87) N-[2-(2,7-diazaspiro[4.4]non-2-yl)quinolin-6-yl]-3-[4-(trifluoromethyl)phenyl]propanamide,
(88) N-{2-[isopropyl(methyl)amino]quinolin-6-yl}-N'-[4-(trifluoromethoxy)phenyl]urea,
(89) N-[2-(2-azabicyclo[2.2.2]oct-2-yl)quinolin-6-yl]-N'-[6-(trifluoromethyl)pyridin-3-yl]urea,
(90) N-[2-(2-azabicyclo[2.2.2]oct-2-yl)quinolin-6-yl]-N'-(6-ethylpyridin-3-yl)urea,
(91) N-[2-(2-azabicyclo[2.2.2]oct-2-yl)quinolin-6-yl]-3-[4-(methylsulfonyl)phenyl]propanamide,
(92) 2,2-dimethyl-N-{1-[6-(5-{2-[4-(trifluoromethyl)phenyl]ethyl}-1,2,4-oxadiazol-3-yl)quinolin-2-yl]pyrrolidin-3-yl}propanamide,
(93) 1-[6-(5-{2-[4-(trifluoromethyl)phenyl]ethyl}-1,2,4-oxadiazol-3-yl)quinolin-2-yl]pyrrolidin-3-amine,
(94) N-{1-[6-(5-{2-[4-(trifluoromethyl)phenyl]ethyl}-1,2,4-oxadiazol-3-yl)quinolin-2-yl]pyrrolidin-3-yl}propanamide,
(95) 2-methyl-N-{1-[6-(5-{2-[4-(trifluoromethyl)phenyl]ethyl}-1,2,4-oxadiazol-3-yl)quinolin-2-yl]pyrrolidin-3-yl}propanamide,
(96) N-{1-[6-(3-{2-[4-(trifluoromethyl)phenyl]ethyl}-1,2,4-oxadiazol-5-yl)quinolin-2-yl]pyrrolidin-3-yl}propanamide,
and pharmaceutically acceptable salts thereof.

11. A method of treating or suppressing a disease mediated by the MCH receptor by reducing food intake in a subject in need thereof comprising administration of a therapeutically effective amount of a compound according to claim 1.

12. The method according to claim 11 wherein the disease is mediated by the $MCH_1R$ receptor.

13. A method of treating obesity in a subject in need thereof comprising administration of a therapeutically effective amount of a compound according to claim 1.

14. The method according to claim 13, additionally comprising administration of a therapeutically effective amount of an anorectic agent or a selective serotonin reuptake inhibitor.

15. The method according to claim 14 wherein the anorectic agent is selected from: aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and the selective serotonin reuptake inhibitor is selected from: fluoxetine, fluvoxamine, paroxetine and sertraline.

16. A method of preventing obesity in a person at risk for obesity comprising administration to said person of about 0.01 mg to about 100 mg per kg of a compound according to claim 1.

17. A composition comprising a compound according to claim 1 and a pharmaceutically acceptable carrier.

18. A method of treating depression in a subject in need thereof comprising administering an effective amount of an MCH-1R receptor antagonist compound according to claim 1 to the subject.

* * * * *